(12) United States Patent
Hulin et al.

(10) Patent No.: US 6,297,269 B1
(45) Date of Patent: Oct. 2, 2001

(54) SUBSTITUTED N-(INDOLE-2-CARBONYL-) AMIDES AND DERIVATIVES AS GLYCOGEN PHOSPHORYLASE INHIBITORS

(75) Inventors: Bernard Hulin, Essex; Dennis J. Hoover, Stonington; Judith L. Treadway, Gales Ferry; William H. Martin, Essex, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 08/952,668

(22) PCT Filed: Jun. 6, 1995

(86) PCT No.: PCT/IB95/00443

§ 371 Date: Dec. 2, 1997

§ 102(e) Date: Dec. 2, 1997

(87) PCT Pub. No.: WO96/39385

PCT Pub. Date: Dec. 12, 1996

(51) Int. Cl.$^7$ ................. A01N 43/38; C07D 209/10; C07D 209/42
(52) U.S. Cl. ................. 514/414; 548/491; 548/492
(58) Field of Search ................. 548/492, 491, 548/414

(56) References Cited

U.S. PATENT DOCUMENTS

| | | | |
|---|---|---|---|
| 4,764,610 | 8/1988 | Zimmerman | 71/92 |
| 4,836,846 | 6/1989 | Zimmerman | 71/93 |
| 4,902,708 | 2/1990 | Kim | 514/19 |
| 4,904,846 | 2/1990 | Oscadal | 219/341 |
| 4,933,325 | 6/1990 | Hansen, Jr. et al. | 514/19 |
| 4,997,950 | 3/1991 | Murphy et al. | 548/303 |
| 5,034,376 | 7/1991 | Hoover et al. | 514/18 |
| 5,064,853 | 11/1991 | Gasc et al. | 514/19 |
| 5,089,638 | 2/1992 | Freidinger | 549/468 |
| 5,128,346 | 7/1992 | Nadzan et al. | 513/307 |
| 5,219,859 | 6/1993 | Festal et al. | 514/269 |
| 5,250,517 | 10/1993 | Branca et al. | 514/18 |
| 5,346,907 | 9/1994 | Kerwin, Jr. et al. | 514/312 |
| 5,610,144 | 3/1997 | Capet et al. | |

FOREIGN PATENT DOCUMENTS

| | | |
|---|---|---|
| 0080283 | 6/1983 | (EP) . |
| 0288965 | 11/1988 | (EP) . |
| 0336356 | 10/1989 | (EP) . |
| 0405506 | 1/1991 | (EP) . |
| 0431520 | 6/1991 | (EP) . |
| 0288965 | 11/1998 | (EP) . |
| WO8803022 | 5/1988 | (WO) . |
| WO9100725 | 1/1991 | (WO) . |
| WO9102719 | 3/1991 | (WO) . |
| WO9112264 | 8/1991 | (WO) . |
| WO9113874 | 9/1991 | (WO) . |
| WO9320099 | 10/1993 | (WO) . |
| 93/2009 * | 10/1993 | (WO) . |
| WO9406755 | 3/1994 | (WO) . |
| WO9407815 | 4/1994 | (WO) . |

OTHER PUBLICATIONS

Martin, J.L. et al. "Biochemistry" 1991, 30, 10101.
Kasvinsky, P. J. et al. "J. Biol. Chem." 1978, 253, 3343–3351 and 9102–9106.
Blundell, T. B. et al. "Diabetologia" 1992, 35, Suppl. 2, S69–S76.
Chemical abstr., vol. 90, No. 19, May 7, 1979 (Columbus, Ohio, USA p. 587, col. 2, the abstract No. 151917p, Pigulla, J. et al., "Preparation of indole–2—carboxamides and esters of (indole–2–ylcarbonylamino)carboxylic acids by the imidazolide method," Arch. Pharm. (Weinhem, Ger.) 1979, 312(1), 12–18 (Ger.).
Chemical Abstr., vol. 90, No. 3, Jan. 15, 1979 (Columbus, OH, USA), p. 636, col. 1, the abstract No. 22858w, Pigulla, J. et al., "Azepinoindoles, III. Cyclization of N–(2–indolylcarbonyl)–β–amino acids to azepinol[3,4-b]indolediones", Justus Liegbigs Ann. Chem. 1978, (9), 1390–8.
Allard, M. F. et al. "Am. J. Physiol." 1994, 267, H66–H74.
Farris P. L. et al. ,Science 1984, vol. 226, pp. 1215–1217, "Morphine Analgesia Potentiated but Tolerance Not Affected by Active Immunization Against Sholecystokinin".
Bock, Mark G. et al. "J. Med. Chem." 1989, 32, pp. 13–16, "Benzodiazepine Gastrin and Brain Cholecystokinin Receptor Ligands: L–365,260".
Schroff, James R. et al. "J. Med. Chem." 1982, 25, pp. 359–362, "Chemistry and Hypoglycemic Activity of N–[[(Dialkylamino)alkoxy]pheny]benzamidines".
Burn, Peter et al., "J. Med. Chem." 1982, 25, pp. 363–368, "Synthesis and Dopaminergic Properties of Some exo-and endo–2–Aminobenzonorbornenes Designed as Rigid Analogues of Dopamine".
Wolfe, Christopher L., et al., Circulation, vol. 87, No. 3, "Loss of Myocardial Protection After Preconditioning Correlates with the Time Course of Glycogen Recovery within the Preconditioned Segment," Mar. 1993.

* cited by examiner

Primary Examiner—Robert W. Ramsuer
Assistant Examiner—Domenik Keating
(74) Attorney, Agent, or Firm—Peter C. Richardson; Gregg C. Benson; A. Dean Olson

(57) ABSTRACT

Compounds of the formula I:

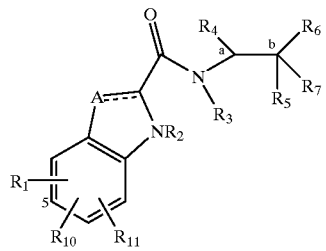

Formula I and their compositions are useful as glycogen phosphorylase inhibitors.

77 Claims, No Drawings

SUBSTITUTED N-(INDOLE-2-CARBONYL-) AMIDES AND DERIVATIVES AS GLYCOGEN PHOSPHORYLASE INHIBITORS

This application was filed under 35 U.S.C. §371 based on PCT/IB95/00443, which was filed on Jun. 6, 1995.

BACKGROUND OF THE INVENTION

This invention relates to glycogen phosphorylase inhibitors, pharmaceutical compositions containing such inhibitors and the use of such inhibitors to treat diabetes, hyperglycemia, hypercholesterolemia, hypertension, hyperinsulinemias, hyperlipidemia, atherosclerosis and myocardial ischemia in mammals.

In spite of the early discovery of insulin and its subsequent widespread use in the treatment of diabetes, and the later discovery of and use of sulfonylureas (e.g. Chlorpropamide™ (Pfizer), Tolbutamide™ (Upjohn), Acetohexamide™ (E. I. Lilly), Tolazamide™ (Upjohn)) and biguanides (e.g. Phenformin™ (Ciba Geigy), Metformin™ (G. D. Searle)) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily doses, usually by self injection. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral agents, e.g. sulfonylureas, and in more severe cases, insulin. However, the clinically available hypoglycemics can have other side effects which limit their use. In any event, where one of these agents may fail in an individual case, another may succeed. A continuing need for hypoglycemic agents, which may have fewer side effects or succeed where others fail, is clearly evident.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle cells laden with lipid and surrounded by extra-cellular lipid, collagen, elastin and proteoglycans. The cells plus matrix form a fibrous cap that covers a deeper deposit of cell debris and more extra cellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition which occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure and stroke (brain hemorrhaging). These conditions are capable of causing short-term death in a patient. Hypertension can also contribute to the development of atherosclerosis and coronary disease. These conditions gradually weaken a patient and can led to long-term death.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure and brain hemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries; while sodium retention increases blood volume. Thus, the lowering of insulin levels in hyperinsulinemics can prevent abnormal vascular growth and renal sodium retention caused by high insulin levels and thereby alleviate hypertension.

Cardiac hypertrophy is a significant risk factor in the development of sudden death, myocardial infarction, and congestive heart failure. These cardiac events are due, at least in part, to increased susceptibility to myocardial injury after ischemia and reperfusion which can occur in outpatient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20–25% in some series. In addition, of the 400,000 patients undergoing coronary by-pass surgery annually, perioperative myocardial infarction is estimated to occur in 5% and death in 1–2%. There is currently no drug therapy in this area which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients.

Hepatic glucose production is an important target for NIDDM therapy. The liver is the major regulator of plasma glucose levels in the post absorptive (fasted) state, and the rate of hepatic glucose production in NIDDM patients is significantly elevated relative to normal individuals. Likewise, in the postprandial (fed) state, where the liver has a proportionately smaller role in the total plasma glucose supply, hepatic glucose production is abnormally high in NIDDM patients.

Glycogenolysis is an important target for interruption of hepatic glucose production. The liver produces glucose by glycogenolysis (breakdown of the glucose polymer glycogen) and gluconeogenesis (synthesis of glucose from 2- and 3-carbon precursors). Several lines of evidence indicate that glycogenolysis may make an important contribution to hepatic glucose output in NIDDM. First, in normal post absorptive man, up to 75% of hepatic glucose production is estimated to result from glycogenolysis. Second, patients having liver glycogen storage diseases, including Hers' disease (glycogen phosphorylase deficiency), display episodic hypoglycemia. These observations suggest that glycogenolysis may be a significant process for hepatic glucose production.

Glycogenolysis is catalyzed in liver, muscle, and brain by tissue-specific isoforms of the enzyme glycogen phosphorylase. This enzyme cleaves the glycogen macromolecule to release glucose-1-phosphate and a new shortened glycogen macromolecule. Two types of glycogen phosphorylase inhibitors have been reported to date: glucose and glucose analogs [Martin, J. L. et al. *Biochemistry* 1991, 30, 10101] and caffeine and other purine analogs [Kasvinsky, P. J. et al. *J. Biol. Chem.* 1978, 253, 3343–3351 and 9102–9106]. These compounds, and glycogen phosphorylase inhibitors in general, have been postulated to be of potential use for the treatment of NIDDM by decreasing hepatic glucose production and lowering glycemia. [Blundell, T. B. et al. *Diabetologia* 1992, 35, Suppl. 2, 569–576 and Martin et al. *Biochemistry* 1991, 30, 10101].

The mechanism(s) responsible for the myocardial injury observed after ischemia and reperfusion is not fully understood. It has been reported (M. F. Allard, et al. *Am. J. Physiol.* 267, H66–H74, 1994) that "pre ischemic glycogen reduction . . . is associated with improved post ischemic left ventricular functional recovery in hypertrophied rat hearts".

Thus, although there are a variety of hyperglycemia, hypercholesterolemia, hypertension, hyperlipidemia, atherosclerosis and myocardial ischemia therapies there is a continuing need and a continuing search in this field of art for alternative therapies.

SUMMARY OF THE INVENTION

This invention is directed to glycogen phosphorylase inhibitor compounds of Formula I useful for the treatment of diabetes, hyperglycemia, hypercholesterolemia, hypertension, hyperinsulinemia, hyperlipidemia, atherosclerosis and myocardial ischemia.

The compounds of this invention have the Formula I

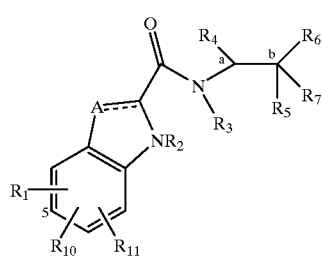

Formula I and the pharmaceutically acceptable salts and prodrugs thereof wherein the dotted line (---) is an optional bond;

A is —C(H)=, —C(($C_1$–$C_4$)alkyl)= or —C(halo)= when the dotted line (---) is a bond, or A is methylene or —CH(($C_1$–$C_4$)alkyl)-when the dotted line (---) is not a bond;

$R_1$, $R_{10}$ or $R_{11}$ are each independently H, halo, 4-, 6- or 7-nitro, cyano, ($C_1$–$C_4$)alkyl, ($C_1$–$C_4$)alkoxy, fluoromethyl, difluoromethyl or trifluoromethyl;

$R_2$ is H;

$R_3$ is H or ($C_1$–$C_5$)alkyl;

$R_4$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, phenyl($C_1$–$C_4$)alkoxy ($C_1$–$C_4$)alkyl, thien-2- or -3-yl($C_1$–$C_4$)alkyl or fur-2- or -3-yl($C_1$–$C_4$)alkyl wherein said $R_4$ rings are mono-, di- or tri-substituted independently on carbon with H, halo, ($C_1$–$C_4$)alkyl, ($C_1$–$C_4$)alkoxy, trifluoromethyl, hydroxy, amino or cyano; or $R_4$ is pyrid-2-, -3- or -4-yl($C_{1-C4}$)alkyl, thiazol-2-, -4- or -5-yl($C_1$–$C_4$)alkyl, imidazol-1-, -2-, 4- or -5-yl($C_1$–$C_4$) alkyl, pyrrol-2- or -3-yl($C_1$–$C_4$)alkyl, oxazol-2-, -4- or -5-yl-($C_1$–$C_4$)alkyl, pyrazol-3-, -4- or -5-yl($C_1$–$C_4$) alkyl, isoxazol-3-, -4- or -5-yl($C_1$–$C_4$)alkyl, isothiazol-3-, -4- or -5-yl($C_1$–$C_4$)alkyl, pyridazin-3- or -4-yl-($C_1$–$C_4$)alkyl, pyrimidin-2-, 4-, -5- or -6-yl($C_1$–$C_4$) alkyl, pyrazin-2- or -3-yl($C_1$–$C_4$)alkyl or 1,3,5-triazin-2-yl($C_1$–$C_4$)alkyl, wherein said preceding $R_4$ heterocycles are optionally mono- or di-substituted independently with halo, trifluoromethyl, ($C_1$–$C_4$) alkyl, ($C_1$–$C_4$)alkoxy, amino or hydroxy and said mono- or di-substituents are bonded to carbon;

$R_5$ is H, hydroxy, fluoro, ($C_1$–$C_5$)alkyl, ($C_1$–$C_5$)alkoxy, ($C_1$–$C_6$)alkanoyl, amino($C_1$–$C_4$)alkoxy, mono-N- or di-N,N-($C_1$–$C_4$)alkylamino($C_1$–$C_4$)alkoxy, carboxy ($C_1$–$C_4$)alkoxy, ($C_1$–$C_5$)alkoxy-carbonyl($C_1$–$C_4$) alkoxy, benzyloxycarbonyl($C_1$–$C_4$)alkoxy, or carbonyloxy wherein said carbonyloxy is carbon-carbon linked with phenyl, thiazolyl, imidazolyl, 1H-indolyl, furyl, pyrrolyl, oxazolyl, pyrazolyl, isoxazolyl, isothiazolyl, pyridazinyl, pyrimidinyl, pyrazinyl or 1,3,5-triazinyl and wherein said preceding $R_5$ rings are optionally mono-substituted with halo, $(C_1-C_4)$alkyl, $(C_1-C_4)$ alkoxy, hydroxy, amino or trifluoromethyl and said mono-substituents are bonded to carbon;

$R_7$ is H, fluoro or $(C_1-C_5)$alkyl; or $R_5$ and $R_7$ can be taken together to be oxo;

$R_6$ is carboxy, $(C_1-C_8)$alkoxycarbonyl, $C(O)NR_8R_9$ or $C(O)R_{12}$, wherein $R_8$ is H, $(C_1-C_3)$alkyl, hydroxy or $(C_1-C_3)$alkoxy; and $R_9$ is H, $(C_1-C_8)$alkyl, hydroxy, $(C_1-C_8)$alkoxy, methylene-perfluorinated$(C_1-C_8)$alkyl, phenyl, pyridyl, thienyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, pyridazinyl, pyrimidinyl, pyrazinyl, piperazinyl or 1,3,5-triazinyl wherein said preceding $R_9$ rings are carbon-nitrogen linked; or $R_9$ is mono-, di- or tri-substituted $(C_1-C_5)$alkyl, wherein said substituents are independently H, hydroxy, amino, mono-N- or di-N,N-$(C_1-C_5)$alkylamino; or $R_9$ is mono- or di-substituted $(C_1-C_5)$alkyl, wherein said substituents are independently phenyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl or 1,3,5-triazinyl wherein the nonaromatic nitrogen-containing $R_9$ rings are optionally mono-substituted on nitrogen with $(C_1-C_6)$ alkyl, benzyl, benzoyl or $(C_1-C_6)$alkoxycarbonyl and wherein the $R_9$ rings are optionally mono-substituted on carbon with halo, $(C_1-C_4)$alkyl, $(C_1-C_4)$alkoxy, hydroxy, amino, or mono-N- and di-N,N $(C_1-C_5)$ alkylamino provided that no quaternized nitrogen is included and there are no nitrogen-oxygen, nitrogen-nitrogen or nitrogen-halo bonds;

$R_{12}$ is piperazin-1-yl, 4-$(C_1-C_4)$alkylpiperazin-1-yl, 4-formylpiperazin-1-yl, morpholino, thiomorpholino, 1-oxothiomorpholino, 1,1-dioxo-thiomorpholino, thiazolidin-3-yl, 1-oxo-thiazolidin-3-yl, 1,1-dioxo-thiazolidin-3-yl, 2-$(C_1-C_6)$alkoxycarbonylpyrrolidin-1-yl, oxazolidin-3-yl or 2(R)-hydroxymethylpyrrolidin-1-yl; or $R_{12}$ is 3- and/or 4-mono-or di-substituted oxazetidin-2-yl, 2-, 4-, and/or 5-mono- or di-substituted oxazolidin-3-yl, 2-, 4-, and/or 5- mono- or di-substituted thiazolidin-3-yl, 2-, 4-, and/or 5- mono- or di-substituted 1-oxothiazolidin-3-yl, 2-, 4-, and/or 5- mono- or di-substituted 1,1-dioxothiazolidin-3-yl, 3- and/or 4-, mono- or di-substituted pyrrolidin-1-yl, 3-, 4- and/or 5-, mono-, di- or tri-substituted piperidin-1-yl, 3-, 4-, and/or 5- mono-, di-, or tri-substituted piperazin-1-yl, 3-substituted azetidin-1-yl, 4- and/or 5-, mono- or di-substituted 1,2-oxazinan-2-yl, 3- and/or 4-mono- or di-substituted pyrazolidin-1-yl, 4- and/or 5-, mono- or di-substituted isoxazolidin-2-yl, 4- and/or 5-, mono- and/or di-substituted isothiazolidin-2-yl wherein said $R_{12}$ substituents are independently H, halo, $(C_1-C_5)$-alkyl, hydroxy, amino, mono-N- or di-N,N-$(C_1-C_5)$ alkylamino, formyl, oxo, hydroxyimino, $(C_1-C_5)$ alkoxy, carboxy, carbamoyl, mono-N-or di-N,N-$(C_1-C_4)$alkylcarbamoyl, $(C_1-C_4)$alkoxyimino, $(C_1-C_4)$alkoxymethoxy, $(C_1-C_6)$alkoxycarbonyl, carboxy$(C_1-C_5)$alkyl or hydroxy$(C_1-C_5)$alkyl;

with the proviso that if $R_4$ is H, methyl, ethyl or n-propyl $R_5$ is OH;

with the proviso that if $R_5$ and $R_7$ are H, then $R_4$ is not H, methyl, ethyl, n-propyl, hydroxy$(C_1-C_3)$alkyl or $(C_1-C_3)$alkoxy$(C_1-C_3)$alkyl and $R_6$ is $C(O)NR_8R_9$, $C(O)R_{12}$ or $(C_1-C_4)$alkoxycarbonyl.

A first group of preferred compounds of Formula I consists of those compounds wherein $R_1$ is 5-H, 5-halo, 5-methyl or 5-cyano;

$R_{10}$ and $R_{11}$ are each independently H or halo;

A is —C(H)=;

$R_2$ and $R_3$ are H;

$R_4$ is phenyl$(C_1-C_2)$alkyl wherein said phenyl groups are mono-, di- or tri-substituted independently with H or halo or mono- or di-substituted independently with H, halo, $(C_1-C_4)$alkyl, $(C_1-C_4)$alkoxy, trifluoromethyl, hydroxy, amino or cyano; or $R_4$ is thien-2- or -3-yl$(C_1-C_2)$alkyl, pyrid-2-, -3- or -4-yl $(C_1-C_2)$ alkyl, thiazol-2-, -4- or -5-yl$(C_1-C_2)$alkyl, imidazol -1-, -2-, -4- or -5-yl$(C_1-C_2)$alkyl, fur-2- or -3-yl$(C_1-C_2)$alkyl, pyrrol-2- or -3-yl$(C_1-C_2)$alkyl, oxazol-2-, -4- or -5-yl-$(C_1-C_2)$alkyl, pyrazol-3-, -4- or -5-yl$(C_1-C_2)$alkyl, isoxazol-3-, -4- or -5-yl$(C_1-C_2)$ alkyl wherein said preceding $R_4$ heterocycles are optionally mono- or di-substituted independently with halo, trifluoromethyl, $(C_1-C_4)$alkyl, $(C_1-C_4)$alkoxy, amino or hydroxy and said mono- or di-substituents are bonded to carbon;

$R_5$ is hydroxy;

$R_6$ is $C(O)NR_8R_9$ or $C(O)R_{12}$; and $R_7$ is H.

Within the above first group of preferred compounds of Formula I is a first group of especially preferred compounds wherein the carbon atom a has (S) stereochemistry;

the carbon atom b has (R) stereochemistry;

$R_4$ is phenyl$(C_1-C_2)$alkyl, thien-2-yl-$(C_1-C_2)$alkyl, thien-3-yl-$(C_1-C_2)$alkyl, fur-2-yl-$(C_1-C_2)$alkyl or fur-3-yl-$(C_1-C_2)$alkyl wherein said rings are mono- or di-substituted independently with H or fluoro;

$R_6$ is $C(O)NR_8R_9$;

$R_8$ is $(C_1-C_3)$alkyl, hydroxy or $(C_1-C_3)$alkoxy; and $R_9$ is H, $(C_1-C_8)$alkyl, hydroxy, hydroxy$(C_1-C_6)$alkyl, $(C_1-C_8)$alkoxy, pyridyl, morpholinyl, piperazinyl, pyrrolidinyl, piperidinyl, imidazolyl or thiazolyl or $(C_1-C_4)$alkyl mono-substituted with pyridyl, morpholinyl, piperazinyl, pyrrolidinyl, piperidinyl, imidazolyl or thiazolyl.

Within the above first group of especially preferred compounds are the particularly preferred compounds 5-Chloro-1H-indole-2-carboxylic acid [(1S)-((R)-hydroxy-dimethylcarbamoyl-methyl)-2-phenyl-ethyl]-amide, 5,6-Dichloro-1H-indole-2-carboxylic acid {(1S)-[(R)-hydroxy-(methoxy-methyl-carbamoyl)-methyl]-2-phenyl-ethyl}-amide, 5-Chloro-1H-indole-2-carboxylic acid {(1S)-[(R)-hydroxy-(methoxy-methyl-carbamoyl)-methyl]-2-phenyl-ethyl}-amide, 5-Chloro-1H-indole-2-carboxylic acid ((1S)-{(R)-hydroxy-[(2-hydroxy-ethyl)-methyl-carbamoyl]-methyl}-2-phenyl-ethyl)-amide, 5-Chloro-1H-indole-2-carboxylic acid {(1S)-[(R)-hydroxy-(methyl-pyridin-2-yl-carbamoyl)-methyl]-2-phenyl-ethyl}-amide or 5-Chloro-1H-indole-2-carboxylic acid ((1S)-{(R)-hydroxy-[methyl-(2-pyridin-2-yl-ethyl)-carbamoyl]-methyl}-2-phenyl-ethyl)-amide.

Within the above first group of especially preferred compounds are the compounds wherein a.
$R_1$ is 5-chloro;
$R_{10}$ and $R_{11}$ are H;
$R_4$ is benzyl;
$R_8$ is methyl; and
$R_9$ is methyl;

b.
$R_1$ is 5-chloro;
$R_{11}$ is H;
$R_{10}$ is 6-chloro;
$R_4$ is benzyl;
$R_8$ is methyl; and
$R_9$ is methoxy;

c.
$R_1$ is 5-chloro;
$R_{10}$ and $R_{11}$ are H;
$R_4$ is benzyl;
$R_8$ is methyl; and
$R_9$ is methoxy;

d.
$R_1$ is 5-chloro;
$R_{10}$ and $R_{11}$ are H;
$R_4$ is benzyl;
$R_8$ is methyl; and
$R_9$ is 2-(hydroxy)ethyl;

e.
$R_1$ is 5-chloro;
$R_{10}$ and $R_{11}$ are H;
$R_4$ is benzyl;
$R_8$ is methyl; and
$R_9$ is pyridin-2-yl; and f.
$R_1$ is 5-chloro;
$R_{10}$ and $R_{11}$ are H;
$R_4$ is benzyl;
$R_8$ is methyl; and
$R_9$ is 2-(pyridin-2-yl)ethyl.

Within the above first group of preferred compounds of Formula I is a second group of especially preferred compounds wherein
the carbon atom a is (S) stereochemistry;
the carbon atom b is (R) stereochemistry;
$R_4$ is phenyl($C_1$–$C_2$)alkyl, thien-2-yl-($C_1$–$C_2$)alkyl, thien-3-yl-($C_1$–$C_2$)alkyl, fur-2-yl-($C_1$–$C_2$)alkyl or fur-3-yl-($C_1$–$C_2$)alkyl wherein said rings are mono- or di-substituted independently with H or fluoro;
$R_6$ is C(O)$R_{12}$; and
$R_{12}$ is morpholino, 4-($C_1$–$C_4$)alkylpiperazin-1-yl, 3-substituted azetidin-1-yl, 3- and/or 4-, mono- or di-substituted pyrrolidin-1-yl, 4- and/or 5- mono- or di-substituted isoxazolidin-2-yl, 4- and/or 5-, mono- or di-substituted 1,2-oxazinan-2-yl wherein said substituents are each independently H, halo, hydroxy, amino, mono-N- or di-N,N-($C_1$–$C_6$)alkylamino, oxo, hydroxy-imino or alkoxy.

Within the above second group of especially preferred compounds are the articularly preferred compounds 5-Chloro-1H-indole-2-carboxylic acid [(1S)-benzyl-(2R)-hydroxy-3-(4-methylpiperazin-1-yl)-3-oxo-propyl]-amide hydrochloride, 5-Chloro-1H-indole-2-carboxylic acid [(1S)-benzyl-(2R)-hydroxy-3-(3-hydroxyazetidin-1-yl)-3-oxo-propyl]-amide, 5-Chloro-1H-indole-2-carboxylic acid ((1S)-benzyl-(2R)-hydroxy-3-isoxazolidin-2-yl-3-oxo-propyl)-amide, 5-Chloro-1H-indole-2-carboxylic acid ((1S)-benzyl-(2R)-hydroxy-3-[1,2]oxazinan-2-yl-3-oxo-propyl)-amide, 5-Chloro-1H-indole-2-carboxylic acid [(1S)-benzyl-(2R)-hydroxy-3-((3S)-hydroxy-pyrrolidin-1-yl)-3-oxo-propyl]-amide, 5-Chloro-1H-indole-2-carboxylic acid [(1S)-benzyl-3-((3S,4S)-dihydroxypyrrolidin-1-yl)-(2R)-hydroxy-3-oxo-propyl]-amide, 5-Chloro-1H-indole-2-carboxylic acid [(1S)-benzyl-3-((3R,4S)-dihydroxypyrrolidin-1-yl)-(2R)-hydroxy-3-oxo-propyl]-amide or 5-Chloro-1H-indole-2-carboxylic acid ((1S)-benzyl-(2R)-hydroxy-3-morpholin-4-yl-3-oxo-propyl)-amide.

Within the above second group of especially preferred compounds are the compounds wherein a.
$R_1$ is 5-chloro;
$R_{10}$ and $R_{11}$ are H;
$R_4$ is benzyl; and
$R_{12}$ is 4-methylpiperazin-1-yl;

b.
$R_1$ is 5-chloro;
$R_{10}$ and $R_{11}$ are H;
$R_4$ is benzyl; and
$R_{12}$ is 3-hydroxyazetidin-1-yl;

c.
$R_1$ is 5-chloro;
$R_{10}$ and $R_{11}$ are H;
$R_4$ is benzyl; and
$R_{12}$ is isoxazolidin-2-yl;

d.
$R_1$ is 5-chloro;
$R_{10}$ and $R_{11}$ are H;
$R_4$ is benzyl; and
$R_{12}$ is (1,2)-oxazinan-2-yl;

e.
$R_1$ is 5-chloro;
$R_{10}$ and $R_{11}$ are H;
$R_4$ is benzyl; and
$R_{12}$ is 3(S)-hydroxypyrrolidin-1-yl;

f.
$R_1$ is 5-chloro;
$R_{10}$ and $R_{11}$ are H;
$R_4$ is benzyl; and
$R_{12}$ is (3S,4S)-dihydroxypyrrolidin-1-yl;

g.
$R_1$ is 5-chloro;
$R_{10}$ and $R_{11}$ are H;
$R_4$ is benzyl; and
$R_{12}$ is (3R,4S)-dihydroxypyrrolidin-1-yl; and h.
$R_1$ is 5-chloro;
$R_{10}$ and $R_{11}$ are H;
$R_4$ is benzyl; and
$R_{12}$ is morpholino.

A second group of preferred compounds of Formula I consists of those compounds wherein $R_1$ is H, halo, methyl or cyano;

$R_{10}$ and $R_{11}$ are each independently H or halo;

A is —C(H)=;

$R_2$ and $R_3$ are H;

$R_4$ is phenyl($C_1$–$C_2$)alkyl wherein said phenyl groups are mono-, di- or tri-substituted independently with H or halo or mono- or di-substituted independently with H, halo, ($C_1$–$C_4$)alkyl, ($C_1$–$C_4$)alkoxy, trifluoromethyl, hydroxy, amino or cyano; or $R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol-1-, -2-, -4- or -5-yl($C_1$–$C_2$)alkyl, fur-2- or -3-yl($C_1$–$C_2$)alkyl, pyrrol-2- or -3-yl($C_1$–$C_2$)alkyl, oxazol-2-, 4- or -5-yl-($C_1$–$C_2$)alkyl, pyrazo-3-, -4- or -5-yl($C_1$–$C_2$)alkyl, isoxazol-3-, -4- or -5-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is hydroxy;

$R_6$ is carboxy or ($C_1$–$C_8$)alkoxycarbonyl; and $R_7$ is H, fluoro or ($C_1$–$C_6$)alkyl.

Within the second group of preferred compounds of Formula I is a group of especially preferred compounds wherein the carbon atom a is (S) stereochemistry;

the carbon atom b is (R) stereochemistry;

$R_4$ is phenyl($C_1$–$C_2$)alkyl, thien-2-yl-($C_1$–$C_2$)alkyl, thien-3-yl-($C_1$–$C_2$)alkyl, fur-2-yl-($C_1$–$C_2$)alkyl or fur-3-yl-($C_1$–$C_2$)alkyl wherein said rings are mono- or di-substituted independently with H or fluoro;

$R_{10}$ and $R_{11}$ are H;

$R_6$ is carboxy; and $R_7$ is H.

Preferred within the immediately preceding group is a compound wherein $R_1$ is 5-chloro;

$R_{10}$ and $R_{11}$ are H; and $R_4$ is benzyl.

A third group of preferred compounds of Formula I consists of those compounds wherein $R_1$ is H, halo, methyl or cyano;

$R_{10}$ and $R_{11}$ are each independently H or halo;

A is —C(H)=;

$R_2$ and $R_3$ are H;

$R_4$ is phenyl($C_1$–$C_2$)alkyl wherein said phenyl groups are mono-, di- or tri-substituted independently with H or halo or mono- or di-substituted independently with H, halo, ($C_1$–$C_4$)alkyl, ($C_1$–$C_4$)alkoxy, trifluoromethyl, hydroxy, amino or cyano; or $R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol-1-, -2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, 4- or -5-yl-($C_1$–$C_2$)alkyl, pyrazol-3-, -4- or -5-yl ($C_1$–$C_2$)alkyl, isoxazol-3-, -4- or -5-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is fluoro, ($C_1$–$C_4$)alkyl, ($C_1$–$C_5$)alkoxy, amino($C_1$–$C_4$) alkoxy, mono-N- or di-N,N-($C_1$–$C_4$)alkylamino ($C_1$–$C_4$)alkoxy, carboxy($C_1$–$C_4$)alkoxy, ($C_1$–$C_5$) alkoxy-carbonyl($C_1$–$C_4$)alkoxy, benzyloxycarbonyl ($C_1$–$C_4$)alkoxy;

$R_6$ is carboxy or ($C_1$–$C_8$)alkoxycarbonyl; and $R_7$ is H, fluoro or ($C_1$–$C_6$)alkyl.

A fourth group of preferred compounds of Formula I consists of those compounds wherein $R_1$ is H, halo, methyl or cyano;

$R_{10}$ and $R_{11}$ are each independently H or halo;

A is —C(H)=;

$R_2$ and $R_3$ are H;

$R_4$ is phenyl($C_1$–$C_2$)alkyl wherein said phenyl groups are mono-, di- or tri-substituted independently with H or halo or mono- or di-substituted independently with H, halo, ($C_1$–$C_4$)alkyl, ($C_1$–$C_4$)alkoxy, trifluoromethyl, hydroxy, amino or cyano; or $R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol-1-, -2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, -4- or -5-yl-($C_1$–$C_2$)alkyl, pyrazol-3-, -4- or -5-yl ($C_1$–$C_2$)alkyl, isoxazol-3-, -4- or -5-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is fluoro, ($C_1$–$C_4$)alkyl, ($C_1$–$C_5$)alkoxy, amino($C_1$–$C_4$) alkoxy, mono-N- or di-N,N-($C_1$–$C_4$)alkylamino ($C_1$–$C_4$)alkoxy, carboxy($C_1$–$C_4$)alkoxy, ($C_1$–$C_5$) alkoxy-carbonyl($C_1$–$C_4$)alkoxy, benzyloxycarbonyl ($C_1$–$C_4$)alkoxy;

$R_6$ is C(O)$NR_8R_9$ or C(O)$R_{12}$ ; and $R_7$ is H, fluoro or ($C_1$–$C_6$)alkyl.

Yet another aspect of this invention is directed to a method for treating a glycogen phosphorylase dependent disease or condition in a mammal by administering to a mammal suffering from a glycogen phosphorylase dependent disease or condition a glycogen phosphorylase dependent disease or condition treating amount of a Formula I compound.

Yet another aspect of this invention is directed to a method for treating hyperglycemia in a mammal by administering to a mammal suffering from hyperglycemia a hyperglycemia treating amount of a Formula I compound.

Yet another aspect of this invention is directed to a method for treating diabetes in a mammal by administering to a mammal suffering from diabetes a diabetes treating amount of a Formula I compound.

Yet another aspect of this invention is directed to a method for treating hypercholesterolemia in a mammal by administering to a mammal suffering from hypercholesterolemia a hypercholesterolemia treating amount of a Formula I compound. Included in the treatment of diabetes is the prevention or attenuation of long term complications such as neuropathy, nephropathy, retinopathy or cataracts.

Yet another aspect of this invention is directed to a method for treating atherosclerosis in a mammal by administering to a mammal suffering from atherosclerosis an atherosclerosis treating amount of a Formula I compound.

Yet another aspect of this invention is directed to a method for treating hyperinsulinemia in a mammal by administering to a mammal suffering from hyperinsulinemia a hyperinsulinemia treating amount of a Formula I compound.

Yet another aspect of this invention is directed to a method for treating hypertension in a mammal by administering to a mammal suffering from hypertension a hypertension treating amount of a Formula I compound.

Yet another aspect of this invention is directed to a method for treating hyperlipidemia in a mammal by administering to a mammal suffering from hyperlipidemia a hyperlipidemia treating amount of a Formula I compound.

Yet another aspect of this invention is directed to a method for preventing a myocardial ischemic injury in a mammal by administering to a mammal at risk for perioperative myocardial ischemic injury a perioperative myocardial ischemic injury preventing amount of a Formula I compound.

Yet another aspect of this invention is directed to a method for preventing a myocardial ischemic injury in a mammal by administering to a mammal at risk for perioperative myocardial ischemic injury a perioperative myocardial ischemic injury preventing amount of a glycogen phosphorylase inhibitor.

This invention is also directed to pharmaceutical compositions which comprise a therapeutically effective amount of a compound of Formula I and a pharmaceutically acceptable carrier.

Preferred compositions include pharmaceutical compositions for the treatment of glycogen phosphorylase dependent diseases or conditions in mammals which comprise a glycogen phosphorylase dependent disease or condition treating amount of a compound of Formula I and a pharmaceutically acceptable carrier.

Another aspect of this invention is directed to pharmaceutical compositions for the treatment of diabetes which comprise a therapeutically effective amount of a glycogen phosphorylase inhibitor;

one or more antidiabetic agents such as insulin and insulin analogs (e.g. LysPro insulin); GLP-1 (7-37) (insulinotropin) and GLP-1 (7-36)-$NH_2$; Sulfonylureas and Analogs: chlorpropamide, glibenclamide, tolbutamide, tolazamide, acetohexamide, glypizide®, glimepiride, repaglinide, meglitinide; Biguanides: metformin, phenformin, buformin; $\alpha$2-Antagonists and Imidazolines: midaglizole, isaglidole, deriglidole, idazoxan, efaroxan, fluparoxan; Other insulin secretagogues: linogliride, A-4166; Glitazones: ciglitazone, pioglitazone, englitazone, troglitazone, darglitazone, BRL49653; Fatty Acid Oxidation Inhibitors: clomoxir, etomoxir; $\alpha$-Glucosidase inhibitors: acarbose, miglitol, emiglitate, voglibose, MDL-25,637, camiglibose, MDL-73,945; $\beta$-Agonists: BRL 35135, BRL 37344, Ro 16-8714, ICI D7114, CL 316,243; Phosphodiesterase Inhibitors: L-386,398; Lipid-lowering Agents: benfluorex; Antiobesity Agents: fenfluramine; Vanadate and vanadium complexes (e.g. naglivan®) and peroxovanadium complexes; Amylin Antagonists; Glucagon Antagonists; Gluconeogenesis Inhibitors; Somatostatin Analogs; Antilipolytic Agents: nicotinic acid, acipimox, WAG 994; and optionally a pharmaceutically acceptable carrier.

Preferred pharmaceutical compositions within the immediately preceding group are those compositions wherein the glycogen phosphorylase inhibitor is a compound of Formula I.

Another aspect of this invention is a method of treating diabetes in a mammal with the above described combination compositions.

Glycogen phosphorylase dependent diseases or conditions refers to disorders which are mediated, initiated or maintained, in whole or in part, by the cleavage of the glycogen macromolecule by glycogen phosphorylase enzymes to release glucose-1-phosphate and a new shortened glycogen molecule. These disorders are ameliorated by reduction of or characterized by an elevation of glycogen phosphorylase activity. Examples include diabetes, hyperglycemia, hypercholesterolemia, hypertension, hyperinsulinemia, hyperlipidemia, atherosclerosis and myocardial ischemia.

The term glycogen phosphorylase inhibitor refers to any substance or agent or any combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis).

The term "treating" as used herein includes preventative (e.g., prophylactic) and palliative treatment.

By halo is meant chloro, bromo, iodo, or fluoro.

By alkyl is meant straight chain or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, hexyl and isohexyl.

By alkoxy is meant straight chain or branched saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, hexoxy and isohexoxy.

The expression "pharmaceutically-acceptable anionic salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate.

The expression "pharmaceutically-acceptable cationic salt" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

The expression "prodrug" refers to compounds that are drug precursors, which following administration, release the drug In vivo via some chemical or physiological process (e.g., a prodrug on being brought to the physiological pH is converted to the desired drug form). Exemplary prodrugs upon cleavage release the corresponding free acid, and such hydrolyzable ester-forming residues of the compounds of this invention include but are not limited to carboxylic acid substituents (e.g., $R_6$ is carboxy, or $R_8$, $R_9$ or $R_{12}$ contains carboxy) wherein the free hydrogen is replaced by ($C_1$–$C_4$) alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as $\beta$-dimethylaminoethyl), carbamoyl-($C_1$–$C_2$)alkyl, N,N-di ($C_1$–$C_2$)alkylcarbamoyl-($C_1$–$C_2$)alkyl and piperidino-, pyrrolidino- or morpholino($C_2$-$C_3$)alkyl.

Other exemplary prodrugs release an alcohol of Formula I wherein the free hydrogen of the hydroxy substituent (e.g., $R_5$ is hydroxy) is replaced by $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1-C_6)$alkyl$)_2$ or glycosyl (the radical resulting from detachment of the hydroxyl of the hemiacetal of a carbohydrate).

Other exemplary prodrugs include but are not limited to derivatives of Formula I wherein $R_2$ is a free hydrogen which is replaced by R-carbonyl, RO-carbonyl, NRR'-carbonyl where R and R' are each independently ($(C_1-C_{10})$alkyl, $(C_3-C_7)$cycloalkyl, benzyl, or R-carbonyl is a natural α-aminoacyl or natural α-aminoacyl-natural α-aminoacyl, —C(OH)C(O)OY wherein (Y is H, $(C_1-C_6)$alkyl or benzyl), —C(OY$_0$)Y$_1$ wherein Y$_0$ is $(C_1-C_4)$ alkyl and Y$_1$ is $((C_1-C_6)$alkyl, carboxy$(C_1-C_6)$alkyl, amino$(C_1-C_4)$alkyl or mono-N- or di-N,N-$(C_1-C_6)$alkylaminoalkyl, —C(Y$_2$)Y$_3$ wherein Y2 is H or methyl and Y$_3$ is mono-N- or di-N,N-$(C_1-C_6)$alkylamino, morpholino, piperidin-1-yl or pyrrolidin-1-yl.

Other exemplary prodrugs include but are not limited to derivatives of formula I bearing a hydrolyzable moiety at $R_3$, which release a compound of formula I wherein $R_3$ is a free hydrogen on hydrolysis. Such hydrolyzable moieties at $R_3$ are/include 1-hydroxy$(C_1-C_6)$alkyl or 1-hydroxy-1-phenylmethyl.

Other exemplary prodrugs include cyclic structures such as compounds of Formula I wherein $R_2$ and $R_3$ are a common carbon, thus forming a five-membered ring. The linking carbon may be mono- or di-substituted independently with H, $(C_1-C_6)$alkyl, $(C_3-C_6)$cycloalkyl or phenyl. Alternatively, $R_3$ and $R_5$ may be taken together to form an oxazolidine ring and the number 2 carbon of the oxazolidine ring may be mono- or di-substituted independently with H, $(C_1-C_6)$alkyl, $(C_3-C_6)$cycloalkyl or phenyl. Alternatively, a prodrug of a Formula I compound includes compounds wherein $R_5$ is taken together with $R_8$ or $R_9$ to form an oxazolidin- 4-one ring and the number 2 carbon of said ring may be mono- or di-substituted independently with H, $(C_1-C_6)$alkyl, $(C_3-C_6)$cycloalkyl, phenyl or oxo.

As used herein, the expressions "reaction-inert solvent" and "inert solvent" refers to a solvent which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates of the compounds of this invention are also included.

The chemist of ordinary skill will recognize that certain combinations of heteroatom-containing substituents listed in this invention define compounds which will be less stable under physiological conditions (e.g. those containing acetal or aminal linkages). Accordingly, such compounds are less preferred.

The term "$R_x$ ring" wherein x is an integer, for example "$R_9$ ring", "$R_{12}$ ring" or "$R_4$ring" as used herein in reference to substitution on the ring refers to moieties wherein the ring is $R_x$ and also wherein the ring is contained within $R_x$.

As used herein the term mono-N- or di-N,N-$(C_1-C_x)$ alkyl . . . refers to the $(C_1-C_x)$ alkyl moiety taken independently when it is di-N,N-$(C_1-C_x)$ alkyl . . . ; (x refers to an integer).

Other features and advantages will be apparent from the specification and claims which describe the invention.

DETAILED DESCRIPTION OF THE INVENTION

In general the compounds of Formula I can be made by processes which include processes known in the chemical arts, particularly in light of the description contained herein. Certain processes for the manufacture of Formula I compounds are provided as further features of the invention and are illustrated by the following reaction schemes.

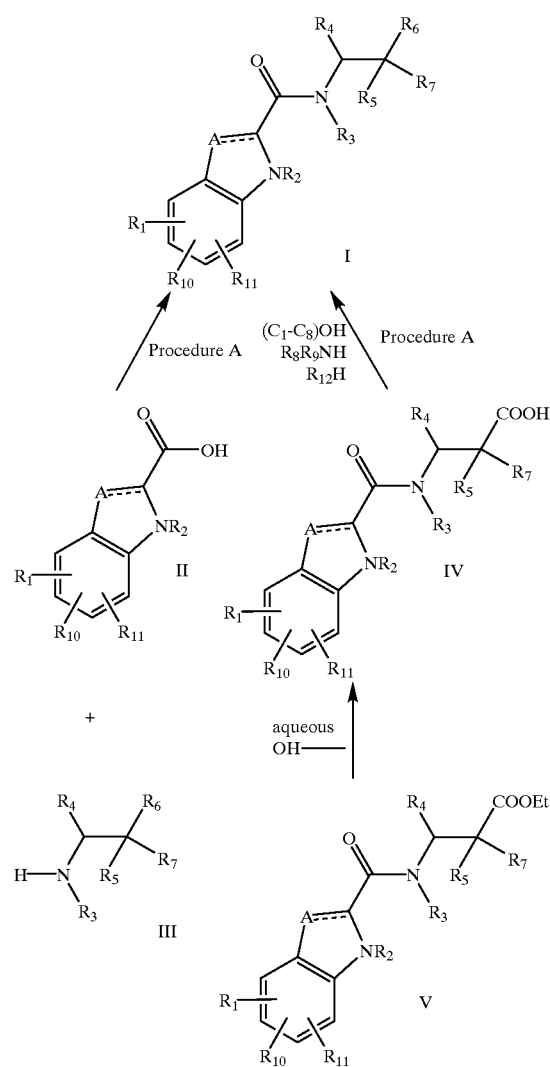

REACTION SCHEME I

REACTION SCHEME II
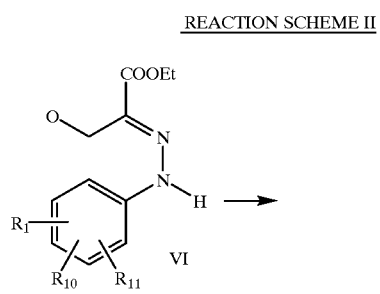
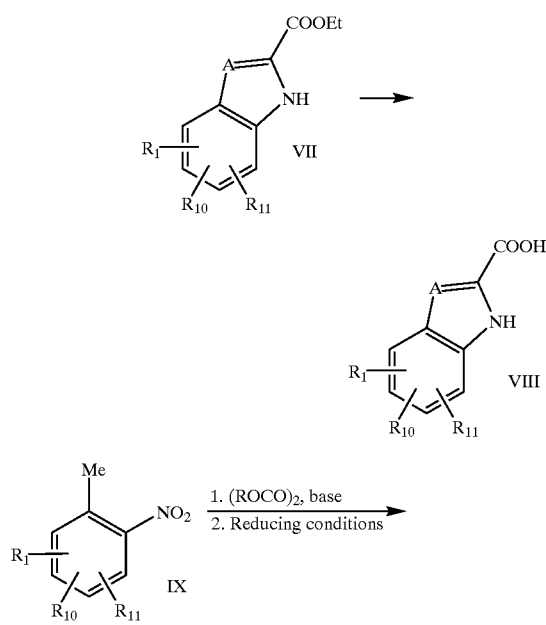
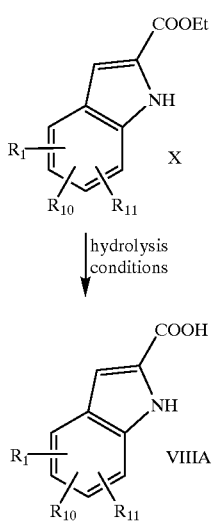
REACTION SCHEME III
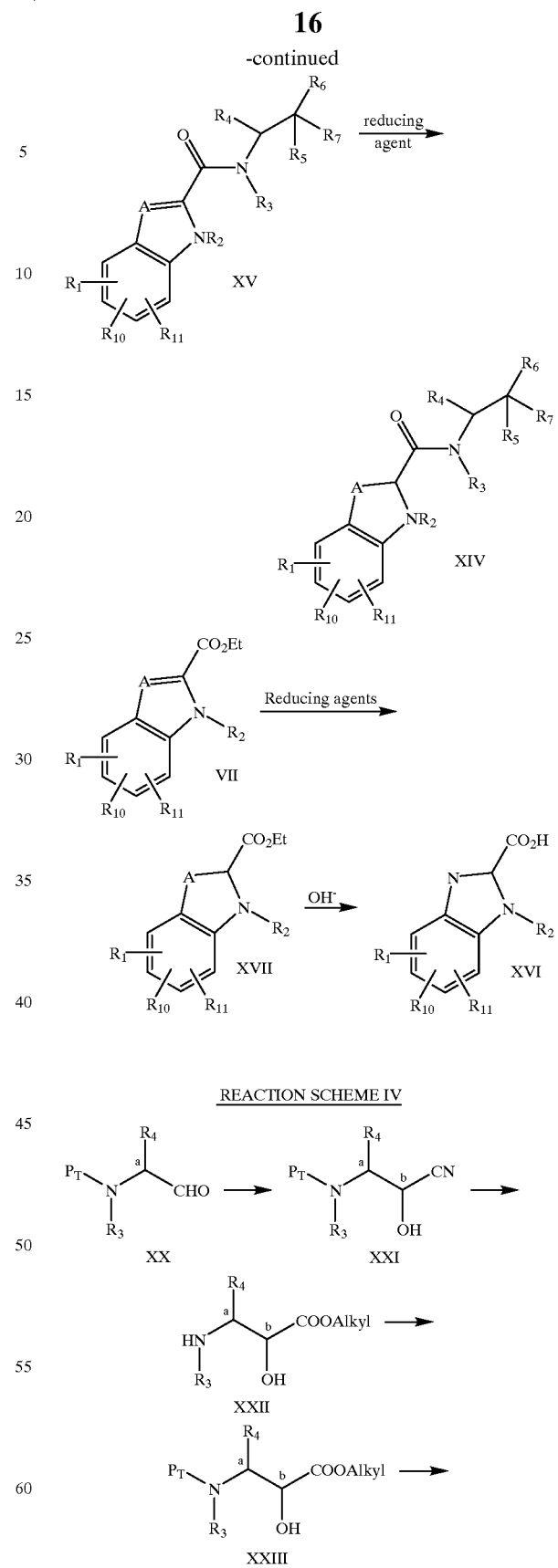
REACTION SCHEME IV

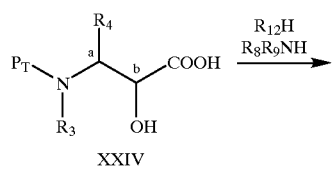
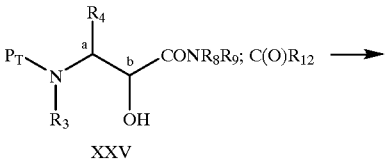
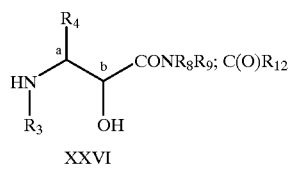
REACTION SCHEME V
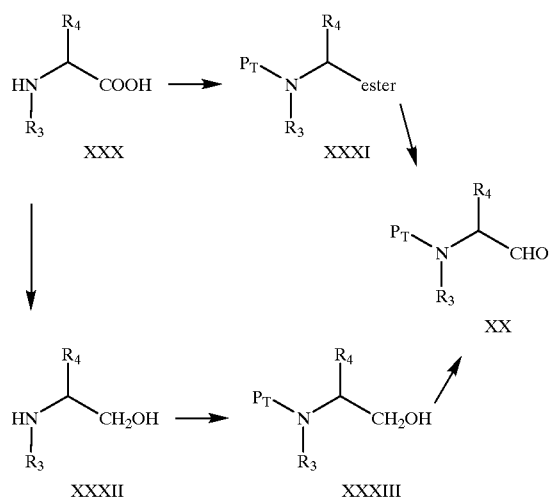
REACTION SCHEME VI
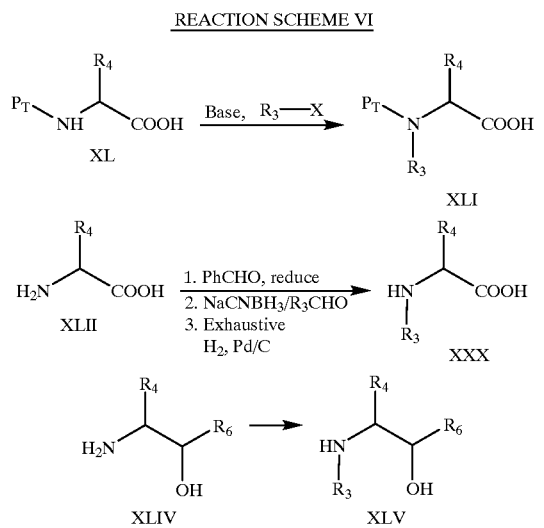
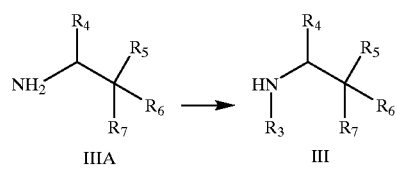
REACTION SCHEME VII
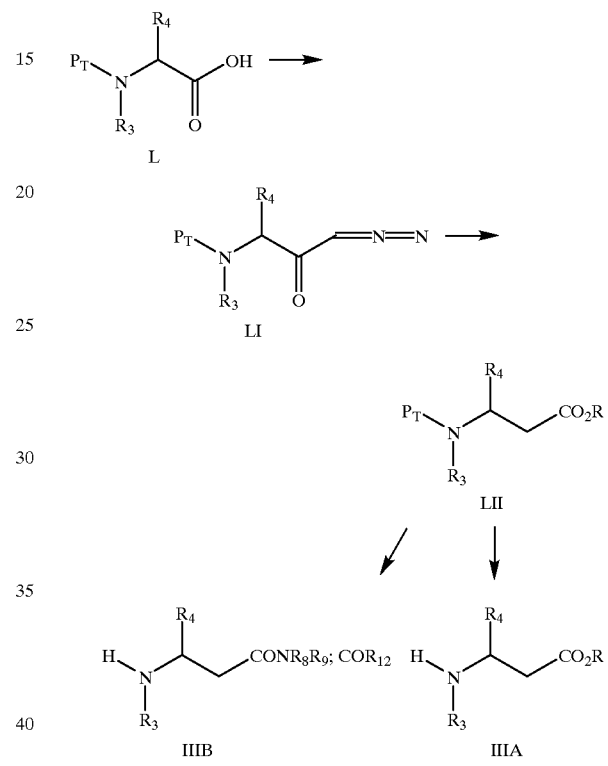
REACTION SCHEME VIII
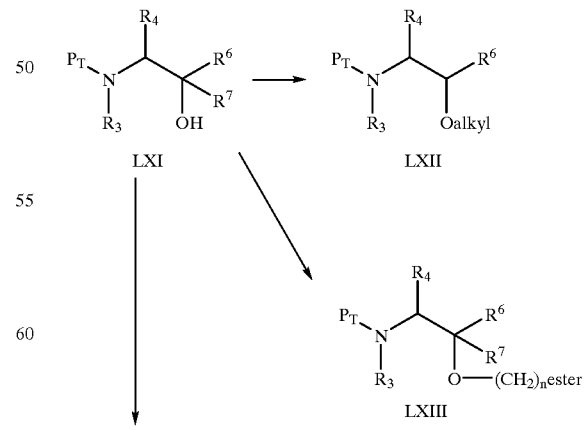

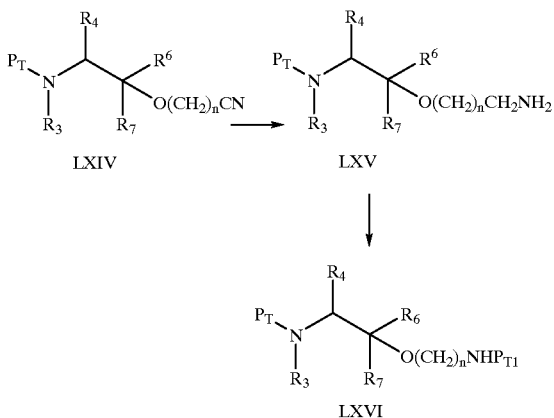

REACTION SCHEME IX

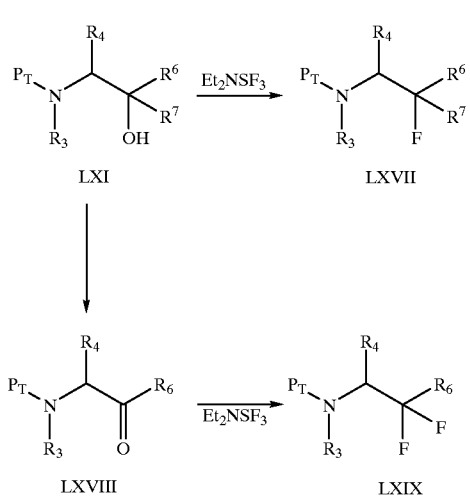

general processes. In the first process the desired Formula I compound may be prepared by coupling the appropriate Formula I indole-2-carboxylic acid or indoline-2-carboxylic acid with the appropriate Formula III amine (i.e., acylating the amine). In the second process the desired Formula I compound may be prepared by coupling the appropriate Formula IV compound (i.e., a Formula I compound wherein $R_6$ is carboxy) with the appropriate alcohol or formula $R_8R_9NH$ or $R_{12}H$ amine or alcohol, wherein $R_8$, $R_9$ and $R_{12}$ are as defined above (i.e., acylating the amine or alcohol).

Typically, the Formula II compound is combined with the Formula III compound (or Formula IV compound is combined with the appropriate amine (e.g., $R_{12}H$ or $R_8R_9NH$)) or alcohol in the presence of a suitable coupling agent. A suitable coupling agent is one which transforms a carboxylic acid into a reactive species which forms an amide or ester linkage on reaction with an amine or alcohol, respectively.

The coupling agent may be a reagent which effects this condensation in a one pot process when mixed together with the carboxylic acid and amine or alcohol. If the acid is to be condensed with an alcohol it is preferable to employ a large excess of the alcohol as the reaction solvent, with or without 1.0 to 1.5 equivalent added dimethylaminopyridine. Exemplary coupling reagents are 1-(3-dimethylaminopropyl)-3-ethylcarbodiimide hydrochloride-hydroxybenzotriazole (DEC/HBT), carbonyldiimidazole, dicyclohexylcarbodiimide/hydroxybenzotriazole (HBT), 2-ethoxy-1-ethoxycarbonyl-1,2-dihydroquinoline (EEDQ), carbonyldiimidazole/HBT, and diethylphosphorylcyanide. The coupling is performed in an inert solvent, preferably an aprotic solvent at a temperature of about −20° C. to about 50° C. for about 1 to about 48 hours. Exemplary solvents include acetonitrile, dichloromethane, dimethylformamide and chloroform. An example of a suitable coupling procedure is Procedure A, contained herein Oust prior to the EXAMPLES).

The coupling agent may also be that agent which converts the carboxylic acid to an activated intermediate which is isolated and/or formed in a first step and allowed to react with the amine or alcohol in a second step. Examples of such coupling agents and activated intermediates are thionyl

REACTION SCHEME X

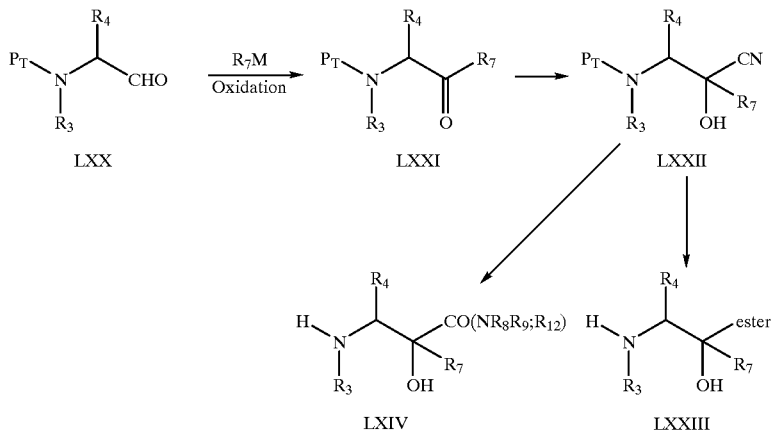

According to Reaction Scheme I the Formula I compounds, wherein $R_1$, $R_{10}$, $R_{11}$, A, $R_2$, $R_3$, $R_4$, $R_5$, $R_6$ and $R_7$ are as defined above may be prepared by either of two chloride or oxalyl chloride to form the acid chloride, cyanuric fluoride to form an acid fluoride or an alkyl chloroformate such as isobutyl or isopropenyl chloroformate (with a tertiary amine base) to form a mixed anhydride of the carboxylic acid. If the coupling agent is oxalyl chloride it is advantageous to employ a small amount of dimethylformamide as cosolvent with another solvent (such as dichloromethane) to catalyze the formation of the acid chloride. Use of these coupling agents and appropriate selection of solvents and temperatures are known to those skilled in the art or can be readily determined from the literature. These and other exemplary conditions useful for coupling carboxylic acids are described in Houben-Weyl, Vol XV, part II, E. Wunsch, Ed., G. Theime Verlag, 1974, Stuttgart, and M. Bodansky, Principles of Peptide Synthesis, Springer-Verlag Berlin 1984, and The Peptides. Analysis, Synthesis and Biology (ed. E. Gross and J. Meienhofer), vols 1–5 (Academic Press NY 1979–1983). The Formula IV compounds wherein $R_1$, $R_{10}$, $R_{11}$, A, $R_2$, $R_3$, $R_4$, $R_5$, and $R_7$ are as defined above may be prepared from the corresponding Formula V ester (i.e., Formula I compounds wherein $R_6$ is $(C_1-C_5)$alkoxycarbonyl or benzyloxycarbonyl) by hydrolysis with aqueous alkali at a temperature of about −20° C. to about 100° C., typically at about 20° C., for about 30 minutes to about 24 hours.

Alternatively, Formula IV compounds are prepared by activation of a Formula II indole carboxylic acid with a coupling agent (as described above) which gives an activated intermediate (such as an acid chloride, acid fluoride, or mixed anhydride) which is then allowed to react with a compound of Formula III wherein $R_3$, $R_4$, $R_5$, and $R_7$ are as described above and $R_6$ is carboxy, in a suitable solvent in the presence of a suitable base. Suitable solvents include wateror methanol or a mixture thereof, together with a cosolvent such as dichloromethane, tetrahydrofuran, or dioxane. Suitable bases include sodium, potassium or lithium hydroxides, sodium or potassium bicarbonate, sodium or potassium carbonate, or potassium carbonate together with tetrabutyl ammonium bromide (1 equivalent) in sufficient quantity to consume the acid liberated in the reaction (generally that quantity sufficient to maintain the pH of the reaction at greater than 8). The base may be added incrementally together with the activated intermediate to effect proper pH control of the reaction. The reaction is conducted generally between −20° C. and 50° C. Isolation procedures are tailored by one skilled in the art to remove impurities, but typically consist of removal of water-miscible cosolvents by evaporation, extraction of impurities at high pH with an organic solvent, acidification to low pH (1–2) and filtration or extraction of the desired product with a suitable solvent such as ethyl acetate or dichloromethane.

The Formula V compound may be prepared by coupling the appropriate Formula IIII compound wherein $R_6$ is alkoxycarbonyl and the appropriate Formula II compound in an analogous procedure to that described above (e.g., Procedure A).

Alternatively, Formula I compounds which contain sulfur atoms in the sulfoxide or sulfone oxidation state may be prepared from the corresponding Formula I compounds having the sulfur atom in the unoxidized form, by treatment with a suitable oxidizing agent, such as with m-chloroperoxybenzoic acid in dichloromethane at a temperature of about 0° C. to about 25° C. for about 1 to about 48 hours using about 1 to about 1.3 equivalent for conversion to the sulfoxide oxidation state and greater than about 2 equivalents for conversion to the sulfone oxidation state.

Alternatively, the Formula I compounds that are mono- or di-alkylated on $R_5$ aminoalkoxy may be prepared from the corresponding Formula I compound wherein $R_5$ is aminoalkoxy by monoalkylation or dialkylation on the $R_5$ amine to prepare the desired Formula I compound. Such a mono- or di-alkylation may be conducted by treatment of the $R_5$ aminoalkoxy compound with 1 equivalent of the appropriate carbonyl compound (for monoalkylation) or greater than 2 equivalents of the appropriate carbonyl compound (for dialkylation) and a suitable reducing agent in a suitable solvent. Suitable reducing conditions include sodium cyanoborohydride or sodium borohydride in methanol or ethanol, or hydrogen/hydrogenation catalyst (such as palladium on carbon) in a polar solvent such as water, methanol, or ethanol at about 0° C. to 60° C. for 1 to 48 hours.

Alternatively, the Formula I compounds, wherein $R_5$ is alkanoyloxy (RCOO—), are prepared by O-acylation of the appropriate Formula I compound with an appropriate acid chloride or other activated acid derivative in the presence, if necessary, of a suitable base, (e.g., tertiary amine base such as trialkylamine or pyridine), preferably in an aprotic solvent such as tetrahydrofuran or dichloromethane, at a temperature of about 0° C. to about 50° C., for about 0.5 to about 48 hours.

Alternatively, the Formula I compounds wherein $R_5$ and $R_7$ are taken together to be oxo are prepared by oxidizing a corresponding Formula I compound, for example, wherein $R_5$ is hydroxy and R7 is H, with a suitable oxidizing agent. Exemplary oxidizing agents include the Dess-Martin reagent in dichloromethane, a carbodiimide and dimethylsulfoxide and acid catalyst (Pfitzner-Moffatt conditions or modifications thereof, such as employing a water-soluble carbodiimide) or Swern-type reactions (e.g., oxalyl chloride/DMSO/triethylamine). The Formula I compounds having other oxidation sensitive functionality may benefit from appropriate protection and deprotection of such functionality.

Some of the preparation methods described herein may require protection of remote functionality (i.e., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis,* John Wiley & Sons, New York, 1991.

For example, in Reaction Scheme I certain Formula I compounds contain primary amine, secondary amine or carboxylic acid functionality in the part of the molecule defined by $R_5$ or $R_6$ which may interfere with the intended coupling reaction of Reaction Scheme I if the Formula III intermediate, or $R_{12}H$ or $R_8R_9NH$ amine is left unprotected. Accordingly, the primary or secondary amine functionality may be protected, where it is present in the $R_5$ or $R_6$ moieties of the Formula III intermediate or amine ($R_8R_9NH$ or $R_{12}H$) by an appropriate protecting group during the coupling reaction of Reaction Scheme I. The product of such coupling reaction is a Formula I compound containing the protecting group. This protecting group is removed in a subsequent step to provide the Formula I compound. Suitable protecting groups for amine and carboxylic acid protection include those protecting groups commonly used in peptide synthesis (such as N-t-butoxycarbonyl, N-carbobenzyloxy, and 9-fluorenylmethylenoxycarbonyl for amines and lower alkyl or benzyl esters for carboxylic acids) which are not chemically reactive under the coupling conditions described above (and immediately preceding the Examples herein as Procedure A) and can be removed without chemically altering other functionality in the Formula I compound.

The starting indole-2-carboxylic acids and indoline-2-carboxylic acids used in Reaction Scheme I, when not commercially available or known in the prior art (such art is extensively published), are available by conventional synthetic methods. For example, according to Reaction Scheme II the Formula VII indole ester may be prepared from the Formula VI compound (wherein Q is selected to achieve the desired A as defined above) via a Fischer Indole synthesis (see *The Fischer Indole Synthesis* Robinson, B. (Wiley, New York, 1982)) followed by saponification of the resulting Formula VII indole ester to yield the corresponding Formula VII acid. The starting aryl hydrazone may be prepared by condensation of a readily available hydrazine with the appropriate carbonyl derivative or via the Japp-Klingeman reaction (see *Organic Reactions,* Phillips, R. R., 1959, 10, 143).

Alternatively, the Formula VIIIA indole 2-carboxylic acid may be prepared by condensation of a Formula IX ortho methyl nitro compound with an oxalate ester to yield the Formula X indole ester followed by reduction of the nitro group and subsequent hydrolysis.

This three step process is known as the Reissert indole synthesis (Reissert, Chemische Berichte 1897, 30, 1030). Conditions for accomplishing this sequence, and references thereto, are described in the literature (Kermack, et al., J. Chem. Soc. 1921, 119, 1602; Cannon et al., J. Med. Chem. 1981, 24, 238; Julian, et al in Heterocyclic Compounds, vol 3 (Wiley, New York, N.Y., 1962, R. C. Elderfield, ed.) p 18). An example of the specific implementation of this sequence is Examples 10A–10C herein.

3-Halo-5-chloro-1H-indole-2-carboxylic acids may also be prepared by halogenation of 5-chloro-1H-indole-2-carboxylic acids.

Alternatively, (to Reaction Scheme II) the Formula XIV substituted indolines may be prepared by reduction of the corresponding Formula XV indoles with a reducing agent such as magnesium in methanol at a temperature of about 25° C. to about 65° C. for about 1 to about 48 hours (Reaction Scheme III).

Formula XVI indoline carboxylic acids are prepared by saponification of the corresponding Formula XVII ester (Reaction Scheme III). The Formula XVII compound is prepared by reduction of the corresponding Formula VII indole ester with a reducing agent such as magnesium in methanol as described for the conversion of the Formula XV compound to the Formula XIV compound above.

The following paragraphs describe how to prepare the various amines which are used in the above Reaction Schemes.

According to Reaction Scheme IV the Formula XXII compounds (the Formula III amines of Reaction Scheme I wherein $R_5$ is OH, $R_7$ is H and $R_6$ is an ester) or Formula XXVI compounds ($R_6$ is $C(O)NR_8R_9$ or $C(O)R_{12}$) are prepared starting from a Formula XX N-protected (denoted by $P_T$) aldehyde. The Formula XX aldehyde or the sodium bisulfite adduct of a Formula XX aldehyde is treated with potassium or sodium cyanide in aqueous solution with a cosolvent such as dioxane or ethyl acetate at a temperature of about 0° C. to about 50° C. to provide a Formula XXI cyanohydrin. The Formula XXI cyanohydrin is treated with an alcohol (e.g., ($C_1$–$C_6$)alkanol such as methanol) and a strong acid catalyst such as hydrogen chloride at a temperature of about 0° C. to about 50° C., followed by addition of water, if necessary. The protecting group ($P_T$) is then removed, if still present, by an appropriate deprotection method yielding a Formula XXII compound. For example, if the Formula XX N-protecting group $P_T$ is tert-butoxycarbonyl (t-Boc), the Formula XXIII compound is directly formed from the Formula XXI compound, and addition of water is not necessary. The Formula XXII compound may be protected on nitrogen with an appropriate protecting group to form a Formula XXIII compound followed by hydrolysis of the ester with aqueous alkali at a temperature of about 0° C. to about 50° C. in a reaction-inert solvent resulting in the corresponding Formula XXIV hydroxy acid. The Formula XXIV compound is coupled (in an analogous procedure to the coupling process described in Reaction Scheme I) with an appropriate $R_8R_9NH$ or $HR_{12}$ amine to form a Formula XXV compound, which is then deprotected resulting in the Formula XXVI compound (i.e., Formula III compound wherein $R_5$ is OH, $R_7$ is H and $R_6$ is $C(O)R_{12}$ or $C(O)NR_8R_9$. An example of the conversion of a Formula XXI cyanohydrin to the corresponding Formula XXII methyl ester with removal of the t-boc protecting group is provided in PCT publication WO/9325574, Example 1a. Other examples wherein a cyanohydrin is converted to Formula XXIII lower alkyl esters may be found in U.S. Pat. No. 4,814,342, and EPO publication O438233.

Certain Formula I compounds are stereoisomeric by virtue of the stereochemical configuration at the carbons labeled a and b. One skilled in the art may prepare Formula XXII and XXVI intermediates with the desired stereochemistry according to Reaction Scheme IV. For example, the Formula XX aldehyde is available in either enantiomeric form (stereochemistry at a) by literature procedures outlined below (see Reaction Scheme V). The Formula XXI cyanohydrin may be prepared from the Formula XX compound by treatment with sodium or potassium cyanide as described above while maintaining the stereochemistry at carbon a resulting in a mixture of stereoisomers at carbon b.

The skilled chemist may employ crystallization at this stage to separate isomers or purify one isomer.

For example, the preparation of the Formula XXI compound wherein $P_T$ is Boc, $R_3$ is H, $R_4$ is benzyl and the stereochemistry of carbons a and b is (S) and (R) respectively, employing this route together with purification by recrystallization is described in *Biochemistry* 1992, 31, 8125–8141.

Alternatively, isomer separation may be effected by chromatography or recrystallization techniques after conversion of a compound of formula XXI (mixture of isomers) to a compound of formula XXII, XXIII, XXIV, XXV, XXVI, V, IV, or I by the procedures and/or sequences described herein. Formula XXI intermediates of a specific stereochemistry at carbons a and b are converted to Formula XXII intermediates with retention of this stereochemistry by treatment with an alcohol and a strong acid catalyst, followed by addition of water, if necessary, as described above.

Alternatively, the desired isomer of the Formula XXI compound may also be obtained by derivatization of the Formula XXI intermediate and chromatographic separation of the diastereomeric derivatives (for example with trimethylsilyl chloride (TMS) or t-butyldimethylsilyl chloride (TBDMS) to give O-TMS or O-TBDMS derivatives). For example, Example 24D (contained herein) describes the separation of Formula XXI diastereomeric derivatives. A silyl derivative of a Formula XXI intermediate having a single stereoisomeric form at carbons a and b is converted with retention of stereochemistry to a Formula XXII intermediate (if the silyl group is not removed in this step it is removed subsequently by an appropriate method, such as treatment with tetrabutylammonium fluoride in tetrahydrofuran), by the method described above for the conversion of the Formula XXI compound to the Formula XXII compound (see Example 24C contained herein for conversion of a silyl derivative of Formula XXI compound to a single isomer of Formula XXII with loss of the silyl group).

According to Reaction Scheme V the Formula XX aldehydes (starting materials for Reaction Scheme IV) are prepared from the corresponding Formula XXX amino acids. The Formula XXX amino acid is protected on nitrogen with a protecting group ($P_T$) (such as Boc). The protected compound is esterified with an alcohol and converted to an ester, preferably the methyl or ethyl ester of the Formula XXXI compound. This may be accomplished by treating the Formula XXX compound with methyl or ethyl iodide in the presence of a suitable base (e.g., $K_2CO_3$) in a polar solvent such as dimethylformamide. The Formula XXXI compound is reduced, for example, with diisobutylaluminum hydride in hexane or toluene, or a mixture thereof, at a temperature of about −78° C. to about −50° C. followed by quenching with methanol at −78° C. as described in J. Med. Chem., 1985, 28, 1779–1790 to form the Formula XX aldehyde. Alternatively (not depicted in Reaction Scheme V), analogous N-methoxymethylamides corresponding to the Formula XXXI compound, wherein the alcohol substituent of the ester is replaced by N(OMe)Me, are formed from a Formula XXX compound, N,O-dimethylhydroxylamine and a suitable coupling agent (e.g., 1-(3-dimethylaminopropyl)3-ethylcarbodiimide hydrochloride (DEC) as in Procedure A. The resulting compound is reduced, for example, with lithium aluminum hydride in a reaction-inert solvent such as ether or tetrahydrofuran at a temperature of about 0° C. to about 25° C. to form the Formula XX aldehyde. This two-step method is general for the conversion of N-protected α-amino acids to Formula XX aldehydes (Fehrentz and Castro, Synthesis 1983, 676–678).

Alternatively Formula XX aldehydes may be prepared by oxidation of Formula XXXIII protected aminoalcohols, for example, with pyridine-$SO_3$ at a temperature of about −10° C. to about 40° C. in a reaction-inert solvent, preferably dimethylsulfoxide. Formula XXXIII protected aminoalcohols, if not commercially available, may be prepared by protection of Formula XXXII aminoalcohols. The Formula XXXII aminoalcohols are prepared by reduction of Formula XXX amino acids. This reduction is accomplished by treatment of Formula XXX compounds with lithium aluminum hydride according to the procedure described by Dickman et al., Organic Syntheses; Wiley: New York, 1990; Collect. Vol. VII, p 530, or with sulfuric acid-sodium borohydride by the procedure of Abiko and Masamune, Tetrahedron Lett. 1992 333, 5517–5518, or with sodium borohydride-iodine according to the procedure of McKennon and Meyers, J. Org. Chem. 1993, 58, 3568–3571, who also reviewed other suitable procedures for converting Formula XXX amino acids to Formula XXXII amino alcohols.

According to Reaction Scheme VI the Formula XXX compounds utilized in Reaction Scheme V may be prepared as follows. The Formula XLI amino acids may be prepared by N-alkylation of the Formula XL protected ($P_T$) amino acids by treatment with an appropriate base and alkylating agent. Specific procedures for this alkylation are described by Benoiton, Can. J. Chem 1977, 55, 906–910, and Hansen, J. Org. Chem. 1985, 50 945–950. For example, when $R_3$ is methyl, sodium hydride and methyl iodide in tetrahydrofuran are utilized. Deprotection of the Formula XLI compound yields the desired Formula XXX compound.

Alternatively, a Formula XLII amino acid may be N-alkylated by a three-step sequence involving reductive benzylation (such as with benzaldehyde, Pd/C-catalyzed hydrogenation) to give the mono-N-benzyl derivative and reductive amination with the appropriate acyl compound (for example with formaldehyde and sodium cyanoborohydride to introduce $R_3$ as methyl) to give the N-Benzyl, N-$R_3$-substituted amino acid. The N-benzyl protecting group is conveniently removed (for example by hydrogenation with an appropriate catalyst) to yield the Formula XXX compound. Specific conditions for this three step alkylation procedure are described by Reinhold et al., J. Med. Chem., 1968, 11, 258–260.

The immediately preceding preparation may also be used to introduce an $R_3$ moiety into the Formula XLIV intermediate to form the Formula XLV intermediate (which is a Formula III intermediate wherein $R_7$ is OH). The immediately preceding preparation may also be used to introduce an $R_3$ moiety into a Formula IIIa intermediate (which is a Formula III intermediate wherein $R_3$ is H).

The amino acids used in the schemes herein (e.g., XL, XLII), if not commercially available, or reported in the literature, may be prepared by a variety of methods known to those skilled in the art. For example, the Strecker synthesis or variations thereof may be used. Accordingly, an aldehyde ($R_4$CHO), sodium or potassium cyanide and ammonium chloride react to form the corresponding aminonitrile. The aminonitrile is hydrolyzed with mineral acid to form the desired Formula XLII $R_4C(NH_2)COOH$ amino acid. Alternatively, the Bucherer-Berg method may be used wherein a hydantoin is formed by heating an aldehyde ($R_4$CHO) with ammonium carbonate and potassium cyanide followed by hydrolysis (for example, with barium hydroxide in refluxing dioxane) with acid or base to form the desired Formula XLII $R_4C(NH_2)COOH$ amino acid.

Other methods for synthesis of α-amino acids are also reported in the literature which would permit one skilled in the art to prepare the desired Formula XLII $R_4C(NH_2)COOH$ intermediate necessary for the synthesis of Formula I compounds.

Suitable methods for the synthesis or resolution of Formula XLII compounds are found in reviews by Duthaler (Tetrahedron 1994, 50, 1539–1650), or by Williams (R. M. Williams, Synthesis of optically active amino acids. Pergamon: Oxford, U.K., 1989).

A specific method for the synthesis of a Formula XLII intermediate in either enantiomeric form from the corresponding $R_4X$ (X=Cl, Br, or I) intermediate is the procedure of Pirrung and Krishnamurthy (J. Org. Chem. 1993, 58, 957–958), or by the procedure of O'Donnell, et al. (J. Am. Chem. Soc. 1989, 111, 2353–2355). The required $R_4X$ intermediates are readily prepared by many methods familiar to the chemist skilled in the art. For example, those compounds when $R_4X$ is $ArCH_2X$ may be prepared by radical halogenation of the compound $ArCH_3$ or by formylation of the arene Ar—H and conversion of the alcohol to the bromide.

Another specific method for the synthesis of Formula XLII intermediates in either enantiomeric form is that of Corey and Link (J. Am. Chem. Soc. 1992, 114, 1906–1908). Thus, an intermediate of formula $R_4COCCl_3$ is reduced enantiospecifically to intermediate $R_4CH(OH)CCl_3$, which is converted on treatment with azide and base to an intermediate $R_4CH(N_3)COOH$, which is reduced by catalytic hydrogenation to the desired Formula XLII compound. The requisite trichloromethyl ketone $R_4COCCl_3$ is obtained by reaction of the aldehyde $R_4$CHO with trichloromethide anion followed by oxidation (Gallina and Giordano, Synthesis 1989, 466–468).

Formula III intermediate amines (used in Reaction Scheme I), wherein $R_5$ and $R_7$ are H may be prepared according to Reaction Scheme VII. A Formula L amino acid (suitably protected ($P_T$) is activated by conversion to the acid chloride, fluoride or mixed anhydride (e.g., with isobutyl chloroformate and triethylamine in an inert solvent such as tetrahydrofuran or dioxane at about −0° C. to about −40° C.) and the activated intermediate treated with diazomethane to give the Formula LI diazoketone. The Formula LI diazoketone is treated with an alcohol (ROH) (e.g., ($C_1$–$C_6$)alkanol such as methanol), and a suitable catalyst such as heat, silver oxide or silver benzoate to prepare the Formula LII ester. The Formula LII ester is deprotected to form the Formula IIIA compound (via Wolff rearrangement). Alternatively the Formula LII ester is hydrolyzed, with for example alkali, and coupled with the appropriate $R_{12}H$ or $HNR_8R_9$ amine to prepare the Formula IIIB compound as described previously.

According to Reaction Scheme VIII the Formula III intermediate amines wherein $R_5$ is an oxygen linked substituent (e.g., alkoxy) (used in Reaction Scheme I) may be prepared as follows. The Formula LXI compound is alkylated on oxygen by treatment with an appropriate alkylating agent (e.g., alkyliodide, alkylbromide, alkylchloride or alkyltosylate) and sufficient base to form the alkoxide (sodium or potassium hydride) in a suitable polar aprotic solvent (e.g., dimethylformamide or tetrahydrofuran) at a temperature of about 0° C. to about 150° C. resulting in a Formula LXII compound. The Formula LXII compound is deprotected to afford the desired amine intermediate.

The Formula III intermediate amines wherein $R_5$ is ($C_1$–$C_6$) alkoxycarbonylalkoxy (used in Reaction Scheme I) may be prepared as follows. The Formula LXI compound is alkylated with a halo-alkanoate ester to form a Formula LXIII compound which is then deprotected to form the desired amine. The corresponding acid may be prepared by hydrolysis of the ester using aqueous alkali in an appropriate solvent. Those Formula III amines wherein $R_6$ contains an ester and $R_5$ contains a carboxy may be prepared from the Formula LXIII amine (as prepared above in this paragraph), wherein $R_5$ contains the carboxylic acid functionality protected as the t-butyl ester by treatment with anhydrous acid to provide the corresponding acid at $R_5$ without hydrolyzing the ester at the $R_6$ position.

The Formula LXVI compounds (Formula III intermediate amines wherein $R_5$ is protected aminoalkoxy) may be prepared from the Formula LXI compound. The Formula LXI compound is alkylated with a halo-alkane-nitrile to form the Formula LXIV compound. The Formula LXIV compound is reduced to the primary amine by treatment with hydrogen and an appropriate catalyst (e.g., rhodium-on-carbon) in the pressence of ammonia in preferably a polar, protic solvent such as water, methanol or ethanol to give the Formula LXV primary amine. The Formula LXV compound is protected on nitrogen with a protecting group ($P_{T1}$), which is orthogonal to the other protecting group ($P_T$), followed by deprotection of the $P_T$ protecting group to yield the desired Formula III compound. The protected Formula III compound is coupled with the appropriate Formula II compound and the resulting protected Formula I compound is deprotected.

The Formula LXIII and LXIV compounds wherein n is two are preferably prepared by treatment of the Formula LXI compound with an excess of acrylate ester or acrylonitrile, respectively, in the presence of a suitable base, such as potassium or sodium hydroxide, in a suitable solvent, preferably a polar protic solvent.

According to Reaction Scheme IX the Formula LXVII and Formula LXIX compounds (Formula III compounds wherein $R_5$ is F or $R_5$ and $R_7$ are both F) may be prepared from the Formula LXI compound. The Formula LXI compound is treated with a suitable fluorinating agent such as diethylaminosulfur trifluoride in a reaction-inert solvent such as an aprotic solvent, preferably dichloromethane, to form the Formula LXVII compound. The Formula LXVII compound is conveniently deprotected.

The Formula LXI compound is oxidized to the Formula LXVIII compound utilizing the conditions described above for the preparation of the Formula I compounds wherein $R_5$ and $R_7$ together form oxo. The Formula LXVIII compound is difluorinated under suitable conditions (e.g., diethylaminosulfur trifluoride in dichloromethane).

According to Reaction Scheme X the Formula LXXIII compound or Formula LXIV compound wherein $R_7$ is alkyl (i.e., Formula III compound wherein $R_7$ is alkyl) are prepared from the Formula LXX compound (also see Reaction Scheme V for analogous amine preparation). The Formula LXX compound is treated with an organometallic reagent $R_7M$ and the resulting secondary alcohol oxidized as in the directly preceding paragraph to form the Formula LXXI compound. The Formula LXXI compound is converted via the Formula LXXII cyanohydrin to the Formula LXXIII compound using the same conditions that are used to convert the Formula XXI compound to the Formula XXII compound in Reaction Scheme IV.

Alternatively, the Formula LXXII compound is converted to the Formula LXIV compound as described for the conversion of the cyano intermediate to the amide in Reaction Scheme V.

A compound of the formula $R_8NH_2$ or $R_9NH_2$ is monoalkylated with a carbonyl compound corresponding to $R_8$ or $R_9$, respectively, under appropriate reductive amination conditions, to give a formula $R_8R_9NH$ amine. To avoid dialkylation, it may be preferable to protect the amines ($R_8NH_2$ or $R_9NH_2$) with a suitable protecting group $P_T$ to give $R_8(P_T)NH$ or $R_9(P_T)NH$, for example by reaction with benzaldehyde and a reducing agent. The protected amines are monoalkylated with a carbonyl compound corresponding to $R_9$ or $R_8$ respectively, under suitable reductive amination conditions, to give $R_8R_9N(P_T)$. The protecting group ($P_T$) is removed (e.g. by exhaustive catalytic hydrogenation when $P_T$ is benzyl) to give a compound of formula $R_8R_9NH$. Appropriate reductive amination conditions are available from the literature to one skilled in the art. These conditions include those reported by Borch et al. (J. Am. Chem. Soc. 1971, 2897–2904) and those reviewed by Emerson (Organic Reactions, Wiley: New York, 1948 (14), 174), Hutchins et al. (Org. Prep. Proced. Int 1979 (11), 20, and Lane et al. (Synthesis 1975, 135). Reductive amination conditions favoring N-monoalkylation include those reported by Morales, et al. (Synthetic Communications 1984, 1213–1220) and Verardo et al. (Synthesis 1992 121–125). The $R_8NH_2$ or $R_9NH_2$ amines may also be monoalkylated with $R_9X$ or $R_8X$, respectively, where X is chloride, bromide, tosylate or mesylate. Alternatively, an intermediate of formula $R_8(P_T)NH$ or $R_9(P_T)NH$ may be alkylated with $R_9X$ or $R_8X$, and the protecting group removed to give a compound of formula $R_8R_9NH$.

Additional methods may be used to prepare formula $R_8R_9NH$ amines wherein $R_8$—NH or $R_9$—NH are oxygen-nitrogen linked. Thus a readily available compound of formula ($C_1$–$C_4$)alkoxycarbonyl-NHOH or $NH_2CONHOH$ is dialkylated on nitrogen and oxygen by treatment with base and excess suitable alkylating agent (R—X) to give the corresponding ($C_1$–$C_4$)alkoxycarbonyl-N(R)OR which is then hydrolyzed to give a compound of formula $R_8R_9NH$ (wherein $R_8=R_9=R$). Suitable conditions, base, and alkylating agent include those described by Goel and Krolls (Org. Prep. Proced. Int. 1987, 19, 75–78) and Major and Fleck (J. Am. Chem. Soc. 1928, 50, 1479). Alternatively, a formula $NH_2CONH(OH)$ amine may be sequentially alkylated, first on oxygen to give $NH_2CONH(OR')$, then on nitrogen to give $NH_2CON(R'')(OR')$, by successive treatment with the alkylating agents R'X and R''X, respectively, in the presence of a suitable base. Suitable base and alkylating agents include those described by Kreutzkamp and Messinger (Chem. Ber. 100, 3463–3465 (1967) and Danen et al (J. Am. Chem. Soc. 1973, 95, 5716–5724). Hydrolysis of these alkylated hydroxyurea derivatives yields the amines $R'ONH_2$ and R'ONHR'', which correspond to certain formula $R_8R_9NH$ amines. The chemist skilled in the art can adapt the procedures described in this paragraph to other alkylating agents R, R' and R''—X to prepare other amines of formula $R_8R_9NH$ wherein $R_8$—N or $R_9N$ are oxygen-nitrogen linked. Uno et al (SynLett 1991, 559–560) describe the $BF_3$-catalyzed addition of an organometallic reagent R—Li to an O-alkyl oxime of formula R'CH=N—OR'', to give compounds of formula R'RCH—NH(OR''). This route may also be used to give compounds of formula $R_8R_9NH$ wherein one of $R_9$—NH or $R_9$—NH are oxygen-nitrogen linked.

Prodrugs of this invention where a carboxyl group in a carboxylic acid of Formula I is replaced by an ester may be prepared by combining the carboxylic acid with the appropriate alkyl halide in the presence of a base such as potassium carbonate in an inert solvent such as dimethylformamide at a temperature of about 0° C. to 100° C. for about 1 to about 24 hours. Alternatively the acid is combined with appropriate alcohol as solvent in the presence of a catalytic amount of acid such as concentrated sulfuric acid at a temperature of about 20° C. to 120° C., preferably at reflux, for about 1 hour to about 24 hours. Another method is the reaction of the acid with a stoichiometric amount of the alcohol in the presence of a catalytic amout of acid in an inert solvent such as tetrahydrofuran, with concomitant removal of the water being produced by physical (e.g. Dean-Stark trap) or chemical (e.g. molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as dimethylformamide at a temperature of about 0° C. to 100° C. for about 1 to about 24 hours. Alkanoylaminomethyl ethers may be obtained by reaction of the alcohol with a bis-(alkanoylamino)methane in the presence of a catalytic amount of acid in an inert solvent such as tetrahydrofuran, according to a method described in U.S. Pat. No. 4,997,984. Alternatively, these compounds may be prepared by the methods described by Hoffman et al. in J. Org. Chem. 1994, 59, 3530.

The dialkylphosphate esters may be prepared by reaction of the alcohol with a dialkyl chlorophosphate in the presence of a base in an inert solvent such as tetrahydrofuran. The dihydrogen phosphates may be prepared by reaction of the alcohol with a diaryl or dibenzyl chlorophosphate as described above, followed by hydrolysis or hydrogenation in the presence of a noble metal catalyst, respectively.

Glycosides are prepared by reaction of the alcohol and a carbohydrate in an inert solvent such as toluene in the presence of acid. Typically the water formed in the reaction is removed as it is being formed as described above. An alternate procedure is the reaction of the alcohol with a suitably protected glycosyl halide in the presence of base followed by deprotection.

N-(1-hydroxyalkyl) amides, N-(1-hydroxy-1-(alkoxycarbonyl)methyl) amides or compounds where $R_2$ has been replaced by C(OH)C(O)OY may be prepared by the reaction of the parent amide or indole with the appropriate aldehyde under neutral or basic conditions (e.g. sodium ethoxide in ethanol) at temperatures between 25 and 70° C. N-alkoxymethyl indoles or N-1-(alkoxy)alkyl indoles can be obtained by reaction of the N-unsubstituted indole with the necessary alkyl halide in the presence of a base in an inert solvent. 1-(N,N-dialkylaminomethyl) indole, 1-(1-(N,N-dialkylamino)ethyl) indole and N,N-dialkylaminomethyl amides (e.g. $R_3=CH_2N(CH_3)_2$) may be prepared by the reaction of the parent N—H compound with the appropriate aldehyde and amine in an alcoholic solvent at 25 to 70° C.

The aforementioned cyclic prodrugs (e.g., the prodrugs of this invention where $R_2$ and $R_3$ are a common carbon) may be prepared by reaction of the parent compound (drug) with an aldehyde or ketone or its dimethyl acetal in an inert solvent in the presence of a catalytic amount of acid with concomitant water or methanol removal. Alternatively, these compounds may be prepared by reaction of the amino alcohol or hydroxy amide with a gem-dibromo alkane in the presence of base (e.g. potassium carbonate) in an inert solvent (e.g. dimethylformamide).

The starting materials and reagents for the above described reaction schemes (e.g., amines, substituted indole carboxylic acids, substituted indoline carboxylic acids, amino acids), although the preparation of most of which are described above, are also readily available or can be easily synthesized by those skilled in the art using conventional methods of organic synthesis. For example, many of the intermediates used herein to prepare compounds of Formula I are, are related to, or are derived from amino acids found in nature, in which there is a large scientific interest and commercial need, and accordingly many such intermediates are commercially available or are reported in the literature or are easily prepared from other commonly available substances by methods which are reported in the literature. Such intermediates include, for example, Formula XX, Formula XXX, Formula XXXI, and Formula XXXII compounds.

The compounds of Formula I have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers (e.g., of Formula III, VIII or IX) can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention.

Although many compounds of this invention are not ionizable at physiological conditions, some of the compounds of this invention are ionizable at physiological conditions. Thus, for example some of the compounds of this invention are acidic and they form a salt with a pharmaceutically acceptable cation. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, some of the compounds of this invention are basic, and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. In addition, when the compounds of this invention form hydrates or solvates they are also within the scope of the invention.

The utility of the compounds of the present invention as medical agents in the treatment of metabolic diseases (such as are detailed herein) in mammals (e.g. humans) is demonstrated by the activity of the compounds of this invention in conventional assays and the in vitro and in vivo assays described below. Such assays also provide a means whereby the activities of the compounds of this invention can be compared with the activities of other known compounds. The results of these comparisons are useful for determining dosage levels in mammals, including humans, for the treatment of such diseases.

The purified human liver glycogen phosphorylase a (HLGPa) is obtained by the following procedure.

Expression and fermentation:

The HLGP cDNA is expressed from plasmid pKK233-2 (Pharmacia Biotech. Inc., Piscataway, N.J.) in *E. coli* strain XL-1 Blue (Stratagene Cloning Systems, LaJolla, Calif.). The strain is inoculated into LB medium (consisting of 10 g tryptone, 5 g yeast extract, 5 g NaCl, and 1 ml 1N NaOH per liter) plus 100 mg/L ampicillin, 100 mg/L pyridoxine and 600 mg/L $MnCl_2$ and grown at 37° C. to a cell density of $OD_{550}$=1.0. At this point, the cells are induced with 1 mM isopropyl-1-thio-β-D-galactoside (IPTG). Three hours after induction the cells are harvested by centrifugation and cell pellets are frozen at −70° C. until needed for purification.

Purification of Glycogen Phosphorylase:

The cells in pellets described above are resuspended in 25 mM β-glycerophosphate (pH 7.0) with 0.2 mM DTT, 1 mM $MgCl_2$, plus the following protease inhibitors:

| 0.7 μg/mL | Pepstatin A |
| 0.5 μg/mL | Leupeptin |
| 0.2 mM | phenylmethylsulfonyl fluoride (PMSF), and |
| 0.5 mM | EDTA, | lysed by pretreatment with 200 μg/mL lysozyme and 3 μg/mL DNAase followed by sonication in 250 mL batches for 5×1.5 minutes on ice using a Branson Model 450 ultrasonic cell disrupter (Branson Sonic Power Co., Danbury Conn.). The lysates are cleared by centrifugation at 35,000×g for one hour followed by filtration through 0.45 micron filters. HLGP in the soluble fraction of the lysates (estimated to be less than 1% of the total protein) is purified by monitoring the enzyme activity (as described in HLGPa Activity Assay section, below) from a series of chromatographic steps detailed below.

Immobilized Metal Affinity Chromatography (IMAC):

This step is based on the method of Luong et al (Luong et al. Journal of Chromatography (1992) 584, 77–84.). 500 mL of the filtered soluble fraction of cell lysates (prepared from approximately 160 g of original cell pellet) are loaded onto a 130 mL column of IMAC Chelating-Sepharose (Pharmacia LKB Biotechnology, Piscataway, N.J.) which has been charged with 50 mM $CuCl_2$ and 25 mM β-glycerophosphate, 250 mM NaCl and 1 mM imidazole at pH 7 equilibration buffer. The column is washed with equilibration buffer until the $A_{280}$ returns to baseline. The sample is then eluted from the column with the same buffer containing 100 mM imidazole to remove the bound HLGP and other bound proteins. Fractions containing the HLGP activity are pooled (approximately 600 mL), and ethylenediaminetetraacetic acid (EDTA), DL-dithiothreitol (DTT), phenylmethylsulfonyl fluoride (PMSF), leupeptin and pepstatin A are added to obtain 0.3 mM, 0.2 mM, 0.2 mM, 0.5 μg/mL and 0.7 μg/mL concentrations respectively. The pooled HLGP is desalted over a Sephadex G-25 column (Sigma Chemical Co., St. Louis, Mo.) equilibrated with 25 mM Tris-HCl (pH 7.3), 3 mM DTT buffer (Buffer A) to remove imidazole and is stored on ice until the second chromatographic step.

5'-AMP-Sepharose Chromatography:

The desalted pooled HLGP sample (approximately 600 mL) is next mixed with 70 mL of 5'-AMP Sepharose (Pharmacia LKB Biotechnology, Piscataway, N.J.) which has been equilibrated with Buffer A (see above). The mixture is gently agitated for one hour at 22° C. then packed into a column and washed with Buffer A until the A280 returns to baseline. HLGP and other proteins are eluted from the column with 25 mM Tris-HCl, 0.2 mM DTT and 10 mM adenosine 5'-monophosphate (AMP) at pH 7.3 (Buffer B). HLGP-containing fractions are pooled following identification by determining enzyme (described below) activity and visualizing the M, approximately 97 kdal HLGP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled HLGP is dialyzed into 25 mM β-glycerophosphate, 0.2 mM DTT, 0.3 mM EDTA, 200 mM NaCl, pH 7.0 buffer (Buffer C) and stored on ice until use.

Determination of HLGP Enzyme Activity

A) Activation of HLGP: Conversion of HLGPb to HLGPa

Prior to the determination of HLGP enzyme activity, the enzyme is converted from the inactive form as expressed in *E. coli* strain XL-1 Blue (designated HLGPb) (Stragene Cloning Systems, La Jolla, Calif.) to the active form (designated HLGPa) by phosphorylation of HLGP using phosphorylase kinase as follows:

HLGPb reaction with Immobilized Phosphorylase Kinase

Phosphorylase kinase (Sigma Chemical Company, St. Louis, Mo.) is immobilized on Affi-Gel 10 (BioRad Corp., Melvile, N.Y.) as per the manufacturer's instructions. In brief, the phosphorylase kinase enzyme (10 mg) is incubated with washed Affi-Gel beads (1 mL) in 2.5 mL of 100 mM HEPES and 80 mM $CaCl_2$ at pH 7.4 for 4 hours at 4° C. The Affi-Gel beads are then washed once with the same buffer prior to blocking with 50 mM HEPES and 1 M glycine methyl ester at pH 8.0 for one hour at room temperature. Blocking buffer is removed and replaced with 50 mM HEPES (pH 7.4), 1 mM β-mercaptoethanol and 0.2% $NaN_3$ for storage. Prior to use to convert HLGPb to HLGPa, the Affi-Gel immobilized phosphorylase kinase beads are equilibrated by washing in the buffer used to perform the kinase reaction, consisting of 25 mM β-glycerophosphate, 0.3 mM DTT, and 0.3 mM EDTA at pH 7.8 (kinase assay buffer).

The partially purified, inactive HLGPb obtained from 5'-AMP-Sepharose chromatography above is diluted 1:10 with the kinase assay buffer then mixed with the aforementioned phosphorylase kinase enzyme immobilized on the Affi-Gel beads. NaATP is added to 5 mM and $MgCl_2$ to 6 mM. The resulting mixture is mixed gently at 25° C. for 30 to 60 minutes. The sample is removed from the beads and the percent activation of HLGPb by conversion to HLGPa is estimated by determining HLGP enzyme activity in the presence and absence of 3.3 mM AMP. The percentage of total HLGP enzyme activity due to HLGPa enzyme activity (AMP-independent) is then calculated as follows:

$$\% \text{ of total } HLGP \text{ as } HLGP_a = \frac{HLGP \text{ activity} - AMP}{HLGP \text{ activity} + AMP}$$

HLGPa Activity Assay:

The hypoglycemic activity (also the other disease/condition treating/preventing activities described herein) of the compounds of this invention can be indirectly determined by assessing the effect of the compounds of this invention on the activity of the activated form of glycogen phosphorylase (GPa) by one of two methods; glycogen phosphorylase a activity is measured in the forward direction by monitoring the production of glucose-1-phosphate from glycogen or by following the reverse reaction, measuring glycogen synthesis from glucose-1-phosphate by the release of inorganic phosphate. All reactions are run in triplicate in 96-well microtiter plates and the change in absorbance due to formation of the reaction product is measured at the wavelength specified below in a MCC/340 MKII Elisa Reader (Lab Systems, Finland), connected to a Titertech Microplate Stacker (ICN Biomedical Co, Huntsville, Ala.).

To measure the HLGPa enzyme activity in the forward direction, the production of glucose-1-phosphate from glycogen is monitored by the multienzyme coupled general method of Pesce et al. [Pesce, M. A., Bodourian, S. H., Harris, R. C. and Nicholson, J. F. (1977) Clinical Chemistry 23, 1711–1717] modified as follows: 1 to 100 μg phosphorylase a, 10 units phosphoglucomutase and 15 units glucose-6-phosphate dehydrogenase (Boehringer Mannheim Biochemicals, Indianapolis, Ind.) are diluted to 1 mL in Buffer A (described hereinafter). Buffer A is at pH 7.2 and contains 50 mM HEPES, 100 mM KCl, 2.5 mM ethyleneglycoltetraacetic acid (EGTA), 2.5 mM $MgCl_2$, 3.5 mM $KH_2PO_4$ and 0.5 mM dithiothreitol. 20 μl of this stock is added to 80 μl of Buffer A containing 0.47 mg/mL glycogen, 9.4 mM glucose, 0.63 mM of the oxidized form of nicotinamide adenine dinucleotide phosphate ($NADP^+$). The compounds to be tested are added as 5 μL of solution in 14% dimethylsulfoxide (DMSO) prior to the addition of the enzymes. The basal rate of HLGPa enzyme activity in the absence of inhibitors is determined by adding 5 μL of 14% DMSO and a fully-inhibited rate of HLGPa enzyme activity is obtained by adding 20 μL of 50 mM of the positive control test substance, caffeine. The reaction is followed at room temperature by measuring the conversion of oxidized $NADP^+$ to reduced NADPH at 340 nm.

To measure HLGPa enzyme activity in the reverse direction, the conversion of glucose-1-phosphate into glycogen plus inorganic phosphate is measured by the general method described by Engers et al. [Engers, H. D., Shechosky, S. and Madsen, N. B. (1970) Can. J. Biochem. 48, 746–754] modified as follows: 1 to 100 ug HLGPa is diluted to 1 mL in Buffer B (described hereinafter). Buffer B is at pH 7.2 and contains 50 mM HEPES, 100 mM KCl, 2.5 mM EGTA, 2.5 mM $MgCl_2$ and 0.5 mM dithiothreitol. 20 μL of this stock is added to 80 μL of Buffer B with 1.25 mg/mL glycogen, 9.4 mM glucose, and 0.63 mM glucose-1-phosphate. The compounds to be tested are added as 5 μL of solution in 14% DMSO prior to the addition of the enzyme. The basal rate of HLGPa enzyme activity in the absence of added inhibitors is determined by adding 5 μL of 14% DMSO and a fully-inhibited rate of HLGPa enzyme activity is obtained by adding 20 μL of 50 mM caffeine. This mixture is incubated at room temperature for 1 hour and the inorganic phosphate released from the glucose-1-phosphate is measured by the general method of Lanzetta et al. [Lanzetta, P. A., Alvarez, L. J., Reinach, P. S. and Candia, O. A. (1979) Anal. Biochem. 100, 95–97] modified as follows: 150 μL of 10 mg/mL ammonium molybdate, 0.38 mg/mL malachite green in 1 N HCl is added to 100 μL of the enzyme mix. After a 20 minute incubation at room temperature, the absorbance is measured at 620 nm.

The compounds of this invention are readily adapted to clinical use as hypoglycemic agents. The hypoglycemic activity of the compounds of this invention can be determined by the amount of test compound that reduces glucose levels relative to a vehicle without test compound in male ob/ob mice. The test also allows the determination of an approximate minimal effective dose (MED) value for the in vivo reduction of plasma glucose concentration in such mice for such test compounds.

Since the concentration of glucose in blood is closely related to the development of diabetic disorders, these compounds by virtue of their hypoglycemic action, prevent, arrest and/or regress diabetic disorders.

Five to eight week old male C57BL/6J-ob/ob mice (obtained from Jackson Laboratory, Bar Harbor, Me.) are housed five per cage under standard animal care practices. After a one week acclimation period, the animals are weighed and 25 microliters of blood are collected from the retro-orbital sinus prior to any treatment. The blood sample is immediately diluted 1:5 with saline containing 0.025% sodium heparin, and held on ice for metabolite analysis. Animals are assigned to treatment groups so that each group has a similar mean for plasma glucose concentration. After group assignment, animals are dosed orally each day for four days with the vehicle consisting of either: 1) 0.25% w/v methyl cellulose in water without pH adjustment; or 2) 0.1% Pluronic® P105 Block Copolymer Surfactant (BASF Corporation, Parsippany, N.J.) in 0.1% saline without pH adjustment. On day 5, the animals are weighed again and then dosed orally with the test compound or the vehicle alone. All drugs are administered in vehicle consisting of either: 1) 0.25% w/v methyl cellulose in water without pH adjustment; or 2) 10% DMSO/0.1% Pluronic® P105 (BASF Corporation, Parsippany, N.J.) in 0.1% saline without pH adjustment. The animals are then bled from the retro-orbital sinus three hours later for determination of blood metabolite levels. The freshly collected samples are centrifuged for two minutes at 10,000×g at room temperature. The supernatant is analyzed for glucose, for example, by the Abbott VP™ (Abbott Laboratories, Diagnostics Division, Irving, Tex.) and VP Super System® Autoanalyzer (Abbott Laboratories, Irving, Tex.), using the A-Gent™ Glucose-UV Test reagent system (Abbott Laboratories, Irving, Tex.) (a modification of the method of Richterich and Dauwalder, Schweizerische Medizinische Wochenschrift, 101, 860 (1971)) (hexokinase method) using a 100 mg/dL standard. Plasma glucose is then calculated by the equation:

Plasma glucose (mg/dL)=Sample value×5×1.784=8.92×Sample value where 5 is the dilution factor and 1.784 is the plasma hematocrit adjustment (assuming the hematocrit is 44%).

The animals dosed with vehicle maintain substantially unchanged hyperglycemic glucose levels (e.g., greater than or equal to 250 mg/dL), animals treated with test compounds at suitable doses have significantly depressed glucose levels. Hypoglycemic activity of the test compounds is determined by statistical analysis (unpaired t-test) of the mean plasma glucose concentration between the test compound group and vehicle-treated group on day 5. The above assay carried out with a range of doses of test compounds allows the determination of an approximate minimal effective dose (MED) value for the in vivo reduction of plasma glucose concentration.

The compounds of this invention are readily adapted to clinical use as hyperinsulinemia reversing agents, triglyceride lowering agents and hypocholesterolemic agents. Such activity can be determined by the amount of test compound that reduces insulin, triglycerides or cholesterol levels relative to a control vehicle without test compound in male ob/ob mice.

Since the concentration of cholesterol in blood is closely related to the development of cardiovascular, cerebral vascular or peripheral vascular disorders, the compounds of this invention by virtue of their hypocholesterolemic action, prevent, arrest and/or regress atherosclerosis.

Since the concentration of insulin in blood is related to the promotion of vascular cell growth and increased renal sodium retention, (in addition to the other actions e.g., promotion of glucose utilization) and these functions are known causes of hypertension, the compounds of this invention by virtue of their hypoinsulinemic action, prevent, arrest and/or regress hypertension.

Since the concentration of triglycerides in blood contributes to the overall levels of blood lipids, the compounds of this invention by virtue of their triglyceride lowering activity prevent, arrest and/or regress hyperlipidemia.

Five to eight week old male C57BL/6J-ob/ob mice (obtained from Jackson Laboratory, Bar Harbor, Me.) are housed five per cage under standard animal care practices and fed standard rodent diet ad libitum. After a one week acclimation period, the animals are weighed and 25 microliters of blood are collected from the retro-orbital sinus prior to any treatment. The blood sample is immediately diluted 1:5 with saline containing 0.025% sodium heparin, and held on ice for plasma glucose analysis. Animals are assigned to treatment groups so that each group has a similar mean for plasma glucose concentration. The compound to be tested is administered by oral gavage as an about 0.02% to 2.0% solution (weight/volume (w/v)) in either 1) 10% DMSO/ 0.1% Pluronic® P105 Block Copolymer Surfactant (BASF Corporation, Parsippany, N.J.) in 0.1 % saline without pH adjustment or 2) 0.25% w/v methylcellulose in water without pH adjustment. Single daily dosing (s.i.d.) or twice daily dosing (b.i.d.) is maintained for 1 to 15 days. Control mice receive the 1 0% DMSO/0.1% Pluronic® P105 in 0.1% saline without pH adjustment or the 0.25% w/v methylcellulose in water without pH adjustment only.

Three hours after the last dose is administered, the animals are sacrificed by decapitation and trunk blood is collected into 0.5 mL serum separator tubes containing 3.6 mg of a 1:1 weight/weight sodium fluoride: potassium oxalate mixture. The freshly collected samples are centrifuged for two minutes at 10,000×g at room temperature, and the serum supernatant is transferred and diluted 1:1 volume/volume with a 1TIU/mL aprotinin solution in 0.1% saline without pH adjustment.

The diluted serum samples are then stored at −80° C. until analysis. The thawed, diluted serum samples are analyzed for insulin, triglycerides, and cholesterol levels. Serum insulin concentration is determined using Equate® RIA INSULIN kits (double antibody method; as specified by the manufacturer) purchased from Binax, South Portland, Me. The inter assay coefficient of variation is $\leq 10\%$. Serum triglycerides are determined using the Abbott VP™ and VP Super System® Autoanalyzer (Abbott Laboratories, Irving, Tex.), using the A-Gent™ Triglycerides Test reagent system (Abbott Laboratories, Diagnostics Division,Irving, Tex.) (lipase-coupled enzyme method; a modification of the method of Sampson, et al., Clinical Chemistry 21, 1983 (1975)). Serum total cholesterol levels are determined using the Abbott VP™ and VP Super System® Autoanalyzer (Abbott Laboratories, Irving, Tex.), and A-Gent™ Cholesterol Test reagent system (cholesterol esterase-coupled enzyme method; a modification of the method of Allain, et al. Clinical Chemistry 20, 470 (1974)) using a 100 and 300 mg/dL standards. Serum insulin, triglycerides, and total cholesterol levels are then calculated by the equations, Serum insulin ($\mu$U/mL)=Sample value×2

Serum triglycerides (mg/dL)=Sample value×2

Serum total cholesterol (mg/dL)=Sample value×2 where 2 is the dilution factor.

The animals dosed with vehicle maintain substantially unchanged, elevated serum insulin (e.g. 225 $\mu$U/mL), serum triglycerides (e.g. 225 mg/dl), and serum total cholesterol (e.g. 160 mg/dL) levels, while animals treated with test compounds of this invention generally display reduced serum insulin, triglycerides, and total cholesterol levels. The serum insulin, triglycerides, and total cholesterol lowering activity of the test compounds are determined by statistical analysis (unpaired t-test) of the mean serum insulin, triglycerides, or total cholesterol concentration between the test compound group and the vehicle-treated control group.

Activity in providing protection from damage to heart tissue for the compounds of this invention can be demonstrated in vitro along the lines presented in Butwell et al., Am. J. Physiol., 264, H1884–H1889, 1993 and Allard et al., Am. J. Physio., 1994, 267, H66–H74. Experiments are performed using an isovolumic isolated rat heart preparation, essentially as described in the above-referenced article. Normal male Sprague-Dawley rats, male Sprague-Dawley rats treated to possess cardiac hypertrophy by an aortic banding operation, acutely diabetic male BB/W rats, or non-diabetic BB/W age matched control rats are pretreated with heparin (1000 u, i.p.), followed by pentobarbital (65 mg/kg, i.p.). After deep anesthesia is achieved as determined by the absence of a foot reflex, the heart is rapidly excised and placed into iced saline. The heart is retrogradely perfused through the aorta within 2 minutes. Heart rate and ventricular pressure are determined using a latex balloon in the left ventricle with high pressure tubing connected to a pressure transducer. The heart is perfused with a perfusate solution consisting of (mM) NaCl 118, KCl 4.7, $CaCl_2$ 1.2, $MgCl_2$ 1.2, $NaHCO_3$ 25, glucose 11. The perfusion apparatus is tightly temperature-controlled with heated baths used for the perfusate and for the water jacketing around the perfusion tubing to maintain heart temperature at 37° C. Oxygenation of the perfusate is provided by a pediatric hollow fiber oxygenator (Capiax, Terumo Corp., Tokyo, Japan) immediately proximal to the heart. Hearts are exposed to perfusion solution ±test compound for about 10 minutes or more, followed by 20 minutes of global ischemia and 60 minutes of reperfusion in the absence of the test compound. The heart beats of the control and test compound treated hearts are compared in the period following ischemia. The left ventricular pressure of the control and test compound treated hearts are compared in the period following ischemia. At the end of the experiment, hearts are also perfused and stained to determine the ratio of infarct area relative to the area at risk (%IA/AAR) as described below.

The therapeutic effects of the compounds of this invention in preventing heart tissue damage otherwise resulting from an ischemic insult can also be demonstrated in vivo along lines presented in Liu et al., Circulation, Vol. 84, No. 1, (July 1991), as described specifically herein. The in vivo assay tests the cardioprotection of the test compound relative to the control group which receives saline vehicle. As background information, it is noted that brief periods of myocardial ischemia followed by coronary artery reperfusion protects the heart from subsequent severe myocardial ischemia (Murry et al., Circulation 74:1124–1136, 1986). Cardioprotection, as indicated by a reduction in infarcted myocardium, can be induced pharmacologically using intravenously administered adenosine receptor agonists in intact, anesthetized rabbits studied as an in situ model of myocardial ischemic preconditioning (Liu et al., Circulation 84:350–356, 1991). The in vivo assay tests whether compounds can pharmacologically induce cardioprotection, i.e., reduced myocardial infarct size, when parenterally administered to intact, anesthetized rabbits. The effects of the compounds of this invention can be compared to ischemic preconditioning using the A1 adenosine agonist, $N^6$-1-(phenyl-2R-isopropyl) adenosine (PIA) that has been shown to pharmacologically induce cardioprotection in intact anesthetized rabbits studied in situ (Liu et al., Circulation 84:350–356,1991). The exact methodology is described below.

Surgery: New Zealand White male rabbits (3–4 kg) are anesthetized with sodium pentobarbital (30 mg/kg, i.v.). A tracheotomy is performed via a ventral midline cervical incision and the rabbits are ventilated with 100% oxygen using a positive pressure ventilator. Catheters are placed in the left jugular vein for drug administration and in the left carotid artery for blood pressure measurements. The hearts are then exposed through a left thoracotomy and a snare (00 silk) placed around a prominent branch of the left coronary artery. Ischemia is induced by pulling the snare tight and clamping it in place. Releasing the snare allowed the affected area to reperfuse. Myocardial ischemia is evidenced by regional cyanosis; reperfusion was evidenced by reactive hyperemia.

Protocol: Once arterial pressure and heart rate has been stable for at least 30 minutes the experiment is started. Ischemic preconditioning is induced by twice occluding the coronary artery for 5 min followed by a 10 min reperfusion. Pharmacological preconditioning is induced by twice infusing test compound over, for example 5 minutes and allowing 10 minutes before further intervention or by infusing the adenosine agonist, PIA (0.25 mg/kg). Following ischemic preconditioning, pharmacological preconditioning or no conditioning (unconditioned, vehicle control) the artery is occluded for 30 minutes and then reperfused for two hours to induce myocardial infarction. The test compound and PIA are dissolved in saline or other suitable vehicle and delivered at 1 to 5 ml/kg, respectively.

Staining (Liu et al., *Circulation* 84:350–356, 1991): At the end of the 2 hour reperfusion period, the hearts are quickly removed, hung on a Langendorff apparatus, and flushed for 1 minute with normal saline heated to body temperature (38° C.). The silk suture used as the snare is then tied tightly to reocclude the artery and a 0.5% suspension of fluorescent particles (1–10 $\mu$m) is infused with the perfusate to stain all of the myocardium except the area at risk (nonfluorescent ventricle). The hearts are then quickly frozen and stored overnight at −20° c. On the following day, the hearts are cut into 2 mm slices and stained with 1% triphenyl tetrazolium chloride (TTC). Since TTC reacts with living tissue, this stain differentiates between living (red stained) tissue, and dead tissue (unstained infarcted tissue). The infarcted area (no stain) and the area at risk (no fluorescent particles) are calculated for each slice of left ventricle using a pre-calibrated image analyzer. To normalize the ischemic injury for differences in the area at risk between hearts, the data is expressed as the ratio of infarct area vs. area at risk (%IA/AAR). All data is expressed as Mean ±SEM and compared statistically using single factor ANOVA or unpaired t-test. Significance is considered as p<0.05.

Administration of the compounds of this invention can be via any method which delivers a compound of this invention preferentially to the liver and/or cardiac tissues. These methods include oral routes, parenteral, intraduodenal routes, etc. Generally, the compounds of the present invention are administered in single (e.g., once daily) or multiple doses.

However, the amount and timing of compound(s) administered will, of course, be dependent on the particular disease/condition being treated, the subject being treated, on the severity of the affliction, on the manner of administration and on the judgment of the prescribing physician. Thus, because of patient to patient variability, the dosages given below are a guideline and the physician may titrate doses of the drug to achieve the activity (e.g., glucose lowering activity) that the physician considers appropriate for the patient. In considering the degree of activity desired, the physician must balance a variety of factors such as starting level, other risk (cardiovascular) factors, presence of preexisting disease, and age of the patient and the patient's motivation.

In general an effective dosage for the activities of this invention, for example the blood glucose, triglycerides, and cholesterol lowering activities and hyperinsulinemia reversing activities of the compounds of this invention is in the range of 0.005 to 50 mg/kg/day, preferably 0.01 to 25 mg/kg/day and most preferably 0.1 to 15 mg/kg/day.

Generally, the compounds of this invention are administered orally, but parenteral administration (e.g., intravenous, intramuscular, subcutaneous or intramedullary) may be utilized, for example, where oral administration is inappropriate for the instant target or where the patient is unable to ingest the drug. Topical administration may also be indicated, for example, where the patient is suffering from gastrointestinal disorders or whenever the medication is best applied to the surface of a tissue or organ as determined by the attending physician.

The compounds of the present invention are generally administered in the form of a pharmaceutical composition comprising at least one of the compounds of this invention together with a pharmaceutically acceptable vehicle or diluent. Thus, the compounds of this invention can be administered individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples, see *Remington's Pharmaceutical Sciences,* Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the disease/condition of the subject being treated, i.e., a glycogen phosphorylase dependent disease/condition.

Techniques

NMR spectra were recorded on a Varian XL-300 (Varian Co., Palo Alto, Calif.) or Bruker AM-300 spectrometer (Bruker Co., Billerica, Mass.) at about 23° C. at 300 MHz for proton and 75.4 mHz for carbon nuclei. Chemical shifts are expressed in parts per million downfield from trimethylsilane. Resonances designated as exchangeable did not appear in a separate NMR experiment where the sample was shaken with several drops of $D_2O$ in the same solvent. FAB-MS spectra were obtained on a VG70-2505 spectrometer (V4 analytical LTD., Wythanshaw, Manchester, U.K.) using a liquid matrix consisting of 3:1 dithiothreitol/dithioerythritol. Thermospray MS (TSPMS) were obtained on a Fisons Trio-1000 spectrometer (Fisons Co., Valencia, Calif.) using ammonia ionization. Chemical ionization mass spectra were obtained on a Hewlett-Packard 5989 instrument (Hewlett-Packard Co., Palo Alto, Calif.) (ammonia ionization, PBMS). Where the intensity of chlorine or bromine-containing ions are described the expected intensity ratio was observed (approximately 3:1 for $^{35}Cl/^{37}Cl$-containing ions) and 1:1 for $^{79}Br/^{81}Br$-containing ions) and the intensity of only the lower mass ion is given.

HPLC was performed with 214 nM detection on a 250× 4.6 mm Rainin Microsorb C-18 column (Rainin Co., Woburn, Mass.) eluted isocratically by a two-pump/mixer system supplying the indicated mixture of acetonitrile and aqueous pH 2.1 (with $H_3PO_4$) 0.1 M $KH_2PO_4$, respectively, at 1.5 mL/min. Samples were injected in a 1:1 mixture of acetonitrile and pH 7.0 phosphate buffer (0.025M in each $Na_2HPO_4$ and $KH_2PO_4$). Percent purities refer to percent of total integrated area usually over a 10 to 15 minute run. Melting points are uncorrected and were determined on a Buchi 510 melting point apparatus (Buchi Laboratorums-Technik Ag., Flawil, Switzerland) where melting points of 120.5–122° C. for benzoic acid and 237.5–240.5° C. for p-chlorobenzoic acid (Aldrich 99+% grades) were obtained. Column chromatography was performed with Amicon silica gel (30 uM, 60 A pore size) (Amicon D Vision, W. R. Grace & Co., Beverly, Mass.) in glass columns under low nitrogen pressure. Unless otherwise specified, reagents were used as obtained from commercial sources. Dimethylformamide, 2-propanol, tetrahydrofuran, and dichloromethane used as reaction solvents were the anhydrous grade supplied by Aldrich Chemical Company (Milwaukee, Wis.). Microanalyses were performed by Schwarzkopf Microanalytical Laboratory, Woodside, N.Y. The terms "concentrated" and coevaporated refer to removal of solvent at water aspirator pressure on a rotary evaporator with a bath temperature of less than 45° C.

Procedure A (Peptide Coupling Using DEC)

An 0.1–0.7 M solution of the primary amine (1.0 equiv, or a primary amine hydrochloride and 1.0 to 1.3 equivalents of triethylamine per equiv HCl) in dichloromethane (unless other solvent specified), is treated sequentially at 25° C. with 0.95 to 1.2 equivalent of the specified carboxylic acid, 1.2 to 1.8 equivalent hydroxybenzotriazole hydrate (usually 1.5 equivalent relative to the carboxylic acid), and 0.95–1.2 equivalent (corresponding in mole ratio to the carboxylic acid) 1-(3-dimethylaminopropyl)3-ethylcarbodiimide hydrochloride (DEC) and the mixture is stirred for 14 to 20 hours. (See Note 1 below). The mixture is diluted with ethyl acetate, washed 2 to 3 times with 1 or 2N NaOH, 2 to 3 times with 1 or 2N HCl (Note 2), the organic layer dried over $MgSO_4$, and concentrated giving crude product which is purified by chromatography on silica gel, trituration, or recrystallization, as specified using the specified solvents. Purified products were analyzed by RP-HPLC and found to be of greater than 95% purity unless otherwise noted. Exceptions in the use of Procedure A are noted individually where appropriate below. Reactions conducted at 0 to 25° C. were conducted with initial cooling of the vessel in an insulated ice bath which was allowed to warm to room temperature over several hours.

Note 1: On larger scale couplings (>50 mL solvent) the mixture was concentrated at this point and the residue dissolved in ethyl acetate. Note 2: If the product contained ionizable amine functionality the acid wash was omitted.

EXAMPLE 1

(3S)-[(5-Chloro-1H-indole-2-carbonyl)amino]-(2R)-hydroxy-4-phenylbutyric acid isopropyl ester 1-(3-dimethylaminopropyl)3-ethylcarbodiimide hydrochloride (DEC, 1.03 g, 5.38 mmol) was added in one portion to a solution of (3S)-Amino-4-phenyl-(2R)-hydroxy-butyric acid isopropyl ester (1.35 g, 4.93 mmol), 5-chloro-1H-indole-2-carboxylic acid (1.06 g, 5.4 mmol), and 1-hydroxybenzotriazole hydrate (1.15 g, 7.5 mmol) in dichloromethane (15 mL) at 25° C. The mixture was stirred at 25° C. for 18 hours, diluted with ethyl acetate, the resulting solution washed twice with 2N NaOH, twice with 2N HCl, dried over MgSO4, and concentrated. The residue was chromatographed on 112 g silica eluted with 1:4 ethyl acetate-hexanes (1.5 L) followed by 1:3 ethyl acetate-hexanes giving the title substance: Yield 91%; HPLC (70/30) 5.69 minutes (78%), 21.5 minutes (19%). TSPMS 415/417 (MH+, 100%);

$^1$H NMR (CDCl$_3$) δ9.7 (s, 1H), 7.57 (d, 1H, J=2 Hz), 7.38–7.18 (m, 7–8H), 6.73 (d, 1H, J=ca. 2 Hz), 6.57 (d, 1H, J=9.7 Hz), 5.04 (septet, 1H, J=6.3 Hz), 4.83 (m, 1H), 4.19 (dd, 1H, J=2 Hz), 3.51 (d, 1H, J=3.6 Hz), 3.05 (m, 2H), 1.17 (d, 3H, J=6.3 Hz), 1.11 (d, 3H, J=6.3 Hz). Approximately 15% of another substance, presumed to be the N, O-bis (5-chloro-1H-indole-2-carbonyl derivative) d (partial) 9.80 (s, 1H), 5.28 (dd, 1H, indole-CO$_2$CH) was present.

EXAMPLE 1A

3(S),2(R)-3-amino-2-hydroxy-4-phenylbutyric acid isopropyl ester

A solution of 3(S),2(R)-N-[(1,1-dimethylethoxy)carbonyl]-3-amino-2-hydroxy-4-phenylbutyronitrile (Parris et al., Biochemistry 1992, 31, 8125–8141 (252 g, 0.912 mol) in dry 2-propanol (6 L) was treated at 5–17° C. with anhydrous hydrogen chloride (374 g) and stirred at 25° C. for 20 hours (protected from atmosphere with a tube containing Drierite). Another 348 g anhydrous hydrogen chloride was added at less than 10° C. and the mixture stirred for 72 hours at 25° C. The mixture was concentrated, the residue dissolved in 0.1 N HCl. After standing 1 hour at 25° C., this solution was extracted with ether (3×1 L) and the aqueous layer brought to pH 12 with 6N NaOH (ca. 450 mL). The resulting suspension was extracted with ethyl acetate (4×1 L), the extracts washed with water (500 mL), brine (500 mL), dried and concentrated giving 177 g of a yellow solid. This solid was dissolved in boiling isopropyl ether (2 L), filtered hot, and concentrated by boiling to a volume of 1.4 L. The solid which formed on cooling was collected by filtering the chilled mixture, washed with cold isopropyl ether and dried (107 g). A second crop (12.2 g) was obtained from the mother liquors. A third crop was obtained by chromatographing the concentrated mother liquours on silica gel with a gradient of 2-propanol in dichloromethane (1% to 4%) and recrystallizing the purified product from isopropyl ether (4.4 g, total yield 123.6 g, 57%): mp 106–109° C.; 1H NMR (CDCl3) d 7.35–7.2 (m, 5H), 5.11 (septet, 1H, J=6.2 Hz), 4.01 (d, 1H, J=2.2 Hz), 3.30 (ddd, 1H), 2,91 (A of AB, 1H, J=6.3, 13.3 Hz), 2.71 (B of AB, 1H, J=8.5, 13.3 Hz), 1.8 (br, 2–3H), 1.25 (d, 6H, J=6.2 Hz); TSP-MS 238 (MH+).

EXAMPLE 2

5-Chloro-1H-indole-2-carboxylic acid [(1S)-benzyl-(2R)-hydroxy-3-(4-methyl-piperazin-1-yl)-3-oxo-propyl]-amide hydrochloride (3S)-Amino-(2R)-hydroxy-1-(4-methyl-piperazin-1-yl)-4-phenyl-butan-1-one dihydrochloride (0.25 mmol) and 5-chloro-1H-indole-2-carboxylic acid (0.30 mmol) were coupled according to Procedure A and the product purified by chromatography on silica gel eluting with 0.5–8% ethanol in dichloromethane giving the title substance in 42% yield, together with 13% of less polar material characterized by $^1$H NMR as the corresponding N, O-bis (5-chloro-1H-indole-2-carbonyl derivative. The more polar desired substance (48 mg) was dissolved in a mixture of methanol and 0.25 mL 1N HCl, the resulting solution concentrated, and the resulting solid triturated with ether giving the title substance (42 mg): HPLC (70/30) 80%, 2.53 minutes and 13%, 4.04 min, the latter corresponding in retention time to the N,O-bis O-acylated derivative isolated above.

$^1$H NMR (D$_2$O) δ7.70 (s, 1H), 7.5–7.2 (m, 7H), 7.05 (s, 1H), 4.57 (m, 1H), 4.47 (m, 1H), 4.04 (m, 1H), 3.58 (m 4H), 3.34 (m, 4–5H), 2.97 (s, 1.5H), 2.91 (s, 1.5H). PBMS 455/457 (MH+, 100%)

EXAMPLE 2A (3S)-Amino-(2R)-hydroxy-1-(4-methyl-piperazin-1-yl)-4-phenyl-butan-1-one dihydrochloride

[(1S)-Benzyl-(2R)-hydroxy-3-(4-methyl-piperazin-1-yl)-3-oxo-propyl]-carbamic acid tert-butyl ester (0.190 g, 0.5 mmol) was dissolved in 4 M HCl-dioxane at 25° C. for 0.5 hours. The mixture was concentrated and the residue triturated with ether and dried: Yield 212 mg; HPLC (15/85) 2.85 min; PBMS 278 (MH+, 100%).

EXAMPLE 2B

[(1S)-Benzyl-(2R)-hydroxy-3-(4-methyl-piperazin-1-yl)-3-oxo-propyl]-carbamic acid tert-butyl ester N-Methylpiperazine (75 mg, 0.75 mmol) and (2R,3S)-3-tert-butoxycarbonylamino-2-hydroxy-4-phenyl-butyric acid (0.200 g, 0.68 mmol) were coupled according to Procedure A giving a colorless foam which was used without purification: Yield 225 mg, 88%; PBMS 378 (MH+, 100%);

EXAMPLE 3

5-Chloro-1H-indole-2-carboxylic acid [(1S)-((R)-hydroxy-methylcarbamoyl-methyl)-2-phenyl-ethyl]-amide Methylamine hydrochloride (0.38 mmol) and (3S)-[(5-chloro-1H-indole-2-carbonyl)amino]-(2R)-hydroxy-4-phenylbutyric acid (0.35 mmol) were coupled according to procedure A (except in DMF at 0–25° C.), and the crude product was purified by chromatography on silica gel in 1–8% ethanol in dichloromethane containing 0.5% ammonium hydroxide, giving the title substance:

Yield 82%; HPLC (70/30) 98% at 3.09 min; PBMS 386/388 (MH+, 100%);

Anal. Calcd for C$_{20}$H$_{20}$ClN$_3$O$_3$+0.25 H$_2$O: C, 61.54; H, 5.29; N, 10.76. Found: C, 61.17; H, 5.63; N, 10.83.

EXAMPLE 4

(3S)-[(5-Fluoro-1H-indole-2-carbonyl)-amino]-(2R)-hydroxy-4-phenyl-butyric acid methyl ester (3S)-Amino-(2R)-hydroxy-4-phenyl-butyric acid methyl ester (0.8 mmol, WO 9325574 Example 1A) and 5-fluoro-1H-indole-2-carboxylic acid (0.8 mmol) were coupled according to Procedure A (except at 0–25° C., and with acid then base extraction), and the crude product purified by trituration with ether:

Yield, 71%; HPLC (60/40) 4.51 minutes (98%); mp 219.5–210° C.; PBMS 371 (MH+,100%);

Anal. Calcd for $C_{20}H_{19}FN_2O_4$+0.25 $H_2O$: C, 64.08; H, 5.27; N, 7.44. Found: C, 64.14; H, 5.30; N, 7.48.

EXAMPLE 5

(3S)-[(5-Bromo-1H-indole-2-carbonyl)-amino]-(2R)-hydroxy-4-phenyl-butyric acid methyl ester (3S)-Amino-(2R)-hydroxy-4-phenyl-butyric acid methyl ester (WO 93/25574, Example 1A) (0.7 mmol) and 5-bromo-1H-indole-2-carboxylic acid (0.7 mmol) were coupled according to Procedure A (except at 0–25° C.). The crude product contained 25% of the N,O-bis-acylated material (HPLC) and was used in subsequent transformations without further purification: Yield, 97%; HPLC (70/30) 4.03 minutes (73%), 11.8 minutes (25%). A sample was triturated with ether-hexanes for characterization and biological testing: HPLC (70/30) 4.03 minutes (94%) 11.7 minutes (4%). FABMS 431/433(MH+,35%), 307(100%);

$^1$H NMR (CDCl$_3$) δ9.31 (br, 1H), 7.75 (d, 1H, J=ca. 2 Hz), 7.35–7.20 (m, 7H), 6.73 (d, 1H, J=1.6 Hz), 6.47 (d, 1H, J=9.6 Hz), 4.80 (m, 1H), 4.21 (dd, 1H, J=2, 5 Hz), 3.72 (s, 3H), 3.33 (d, 1H, J=4 Hz), 3.06 (m, 2H).

Anal. Calcd for $C_{20}H_{19}BrN_2O_4$: C, 55.70; H, 4.44; N, 6.50. Found: C, 56.12; H, 4.62; N, 6.16.

EXAMPLE 6

5-Fluoro-1H-indole-2-carboxylic acid [(1S)-((R)-dimethylcarbamoyl-hydroxy-methyl)-2-phenyl-ethyl]-amide Dimethylamine hydrochloride (0.52 mmol) and (3R)-[(5-fluoro-1H-indole-2-carbonyl)-amino]-(2S)-hydroxy-4-phenyl-butyric acid (0.43 mmol) were coupled according to Procedure A (except at 0–25° C.). The crude product was dissolved in dichloromethane and the resulting solution stirred with approx 200 mg dimethylaminopyridine-polystyrene resin (Aldrich Chemical Co., Milwaukee, Wis.) for 1 hour, filtered, and concentrated giving the product as a colorless solid: Yield, 62%; HPLC (60/40) 4.15 minutes (97%); mp 213–214° C.; TSPMS 384 (MH+,100%);

Anal. Calcd for $C_{21}H_{22}FN_3O_3$: C, 65.78; H, 5.78; N, 10.96. Found: C, 65.89; H, 6.16; N, 11.00.

EXAMPLE 7

5-Bromo-1H-indole-2-carboxylic acid {(1S)-[(R)-hydroxy-(methoxy-methyl-carbamoyl)-methyl]-2-phenyl-ethyl}-amide (3S)-Amino-(2R)-hydroxy-N-methoxy-N-methyl-4-phenyl-butyramide hydrochloride (0.36 mmol) and 3-[(5-bromo-1H-indole-2-carbonyl)-amino]-2-hydroxy-4-phenyl-butyric acid (0.36 mmol) were coupled according to Procedure A and the crude product purified by chromatography on silica gel eluting with 30% and 40% ethyl acetate-hexanes followed by trituration with 1:1 ether-hexanes: Yield, 65%; HPLC (60/40) 5.77 minutes (100%); PBMS 460/462 (MH+,90%);

Anal. Calcd for $C_{21}H_{22}BrN_3O_4$: C, 54.79; H, 4.82; N, 9.13. Found: C, 54.88; H, 5.22; N, 8.83.

EXAMPLE 8

5-Chloro-3-methyl-1H-indole-2-carboxylic acid {(1S)-[(R)-hydroxy-(methoxy-methyl-carbamoyl)-methyl]-2-phenyl-ethyl}-amide (3S)-Amino-(2R)-hydroxy-N-methoxy-N-methyl-4-phenyl-butyramide hydrochloride (0.3 mmol) and 5-chloro-3-methyl-1H-indole-2-carboxylic acid (0.3 mmol) were coupled according to Procedure A and the crude product purified by trituration with ether: Yield, 59%, HPLC (60/40) 7.45 minutes (100%); PBMS 430/432 (MH+, 100/40%);

$^1$H NMR (CDCl$_3$) δ8.98 (br, 1H), 7.56 (d, 1H, J=2 Hz), 7.4–7.15 (m, 7H), 6.35 (d, 1H, J=9 Hz), 4.95 (m, 1H), 4.32 (d, 1H, J=5.1 Hz), 3.81 (d, 1H, J=5 Hz), 3.36 (s, 3H), 3.15 (s, 3H), 3.15 (dd, 1H), 3.03 (dd, 1H, J=13, 16 Hz), 2.51 (s, 3H).

Anal. Calcd for $C_{22}H_{24}ClN_3O_4$: C, 61.46; H, 5.63; N, 9.77. Found: C, 61.13; H, 5.53; N, 9.74.

EXAMPLE 8A

5-Chloro-3-methyl-1H-indole-2-carboxylic acid

2N NaOH (20 mL) was added to a suspension of 5-chloro-3-methyl-1H-indole-2-carboxylic acid ethyl ester (7.0 g, 29.4 mmol) in methanol (50 mL) and the resulting mixture stirred at 25° C. for 18 hours. Tetrahydrofuran (100 mL) was added and the resulting solution heated at reflux for 30 minutes and concentrated. The residue was dissolved in water and the resulting solution extracted twice with ethyl acetate. The aqueous layer was acidified and the precipitate collected by filtration and washed with water (5.24 g).

EXAMPLE 8B

5-Chloro-3-methyl-1H-indole-2-carboxylic acid ethyl ester

The p-chlorophenylhydrazone of ethyl 2-oxobutanoate was prepared by adaptation of the Japp-Klingemann reaction as described by lions and Hughes (J. Proc. Roy. Soc. N. S. Wales 1939, 71: 445) to p-chloroaniline and ethyl 2-ethylacetoacetate. This phenylhydrazone was treated with HCl-ethanol according to the procedure of lions and Hughes (J. Proc. Roy. Soc. N. S. Wales 1939, 71: 445) as applied therein to the corresponding bromophenylhydrazone. The title substance was collected by filtration as an orange solid after suspending the concentrated residue in water.

EXAMPLE 8C (3S)-Amino-(2R)-hydroxy-N-methoxy-N-methyl-4-phenyl-butyramide hydrochloride 31055-274-2 31055-85-1

{(1S)-[(R)-Hydroxy-(methoxy-methyl-carbamoyl)-methyl]-2-phenyl-ethyl}-carbamic acid tert-butyl ester (791 mg, 2.3 mmol) was dissolved in 4M HCl-dioxanes for 45 minutes at 25° C. for 45 min, the mixture concentrated, the residue coevaporated with ether, suspended in ether and filtered giving 583 mg (91%) of the title substance.

EXAMPLE 8D

{(1S)-[(R)-Hydroxy-(methoxy-methyl-carbamoyl)-methyl]-2-phenyl-ethyl}-carbamic acid tert-butyl ester (3S)-tert-Butoxycarbonylamino-(2R)-hydroxy-4-phenyl-butyric acid (10.06 g, 34.1 mmol, Schweizerhall, Inc.; S. Plainfield, N.J.) and N,O-dimethylhydroxylamine hydrochloride (3.49 g, 35.7 mmol) were coupled according to Procedure A and the crude product (10.7 g) purified by chromatography on silica gel eluted with 25–50% ethyl acetate-hexanes giving the title substance as a foam (9.5 g, 83%): MS 339 (MH+, 100%).

EXAMPLE 9

(3S)-[(5,6-Dichloro-1H-indole-2-carbonyl)-amino]-(2R)-hydroxy-4-phenyl-butyric acid methyl ester (3S)-Amino-(2R)-hydroxy-4-phenyl-butyric acid methyl ester (1.2 mmol) and 5,6-dichloro-1H-indole-2-carboxylic acid (1.2 mmol) were coupled according to Procedure A (reaction time 72 hours) and the product purified by chromatography on silica using 20–40% ethyl acetate-hexanes: Yield, 52%; 198–202° C.; TSPMS 421/423 (MH+,100%);

Anal. Calcd for $C_{20}H_{18}Cl_2N_2O_4$ +0.25 $H_2O$: C, 56.42; H, 4.38; N, 6.58. Found: C, 56.25; H, 4.17; N, 6.58.

EXAMPLE 9A 5,6-Dichloro-1H-indole-2-carboxylic acid

Zinc dust (3.52 g, 54 mmol) was added slowly to a warm solution of 3,4-dichloro-5-nitrophenylpyruvic acid (1.5 g, 5.4 mmol) in acetic acid (15 mL). After a few minutes a vigorous reaction occurred (exothermic). The resulting solution was heated to 80° C. and the reaction appeared complete (TLC). The mixture was filtered, the filtered solids washed with acetic acid and the filtrate concentrated. The residue was dissolved in 2N NaOH, the resulting solution washed with ether (3×), dichloromethane (2×) and acidified to pH 1 with 6N HCl and extracted with ethyl acetate. The extracts were dried and concentrated giving a light brown solid (458 mg, 34%): HPLC (60/40) 5.31 (93%).

EXAMPLE 9B 3,4-dichloro-5-nitrophenylpyruvic acid potassium salt

Absolute ethanol (25 mL) was added at 3–15° C. to a a stirred mixture of potassium metal (2.67 g, 68 mmol) in ether (100 mL). The resulting solution was treated at 3° C. with a solution of diethyl oxalate (10.0 g, 62 mmol) and 2-methyl-3,4-dichloro-1-nitrobenzene (10.0 g, 62 mmol) over 5–10 min, and the resulting solution stirred 30 minutes at 3° C. and 25° C. for 18 hours. The mixture was filtered and the resulting solid washed with ether and dried (13.7 g). This material (12.7 g) was dissolved in 400 mL hot water, the solution cooled and extracted with ether. The resulting aqueous layer was acidified to pH 2 with conc. HCl and the ether layer separated, dried and concentrated giving 7.5 g of a solid which was triturated with hexanes giving the title substance as a yellow solid (7.01 g, 41%).

EXAMPLE 10

5-Cyano-1H-indole-2-carboxylic acid {(1S)-[(R)-hydroxy-(methoxy-methyl-carbamoyl)-methyl]-2-phenyl-ethyl}-amide (3S)-Amino-(2R)-hydroxy-N-methoxy-N-methyl-4-phenyl-butyramide hydrochloride (0.3 mmol) and 5-cyano-1H-indole-2-carboxylic acid (0.3 mmol) were coupled according to Procedure A (reaction time 5 days). The crude product was dissolved in methanol containing 1.0 equiv 1N NaOH at 25° C. for 45 min, concentrated, the residue dissolved in ethyl acetate, the resulting solution washed with 2×2N HCl, 2×2N NaOH, dried, concentrated, and the residue chromatographed on silica gel eluted with 20–50% ethyl acetate-hexanes. The purified product was triturated with 1:1 ether-hexanes giving the title substance: 66% yield; HPLC (60/40) 3.9 minutes (100%); 210–211° C.; PBMS 407 (MH+,100%);

$^1$H NMR (CDCl$_3$) δ9.83 (br, 1H), 7.97 (s, 1H), 7.46 (m, 2H), 7.36 (m, 4H), 6.99 (d, 1H, J=2 Hz), 6.56 (d, 1H, J=10 Hz), 4.95 (m, 1H), 4.32 (d, 1H, J=5.5 Hz), 3.83 (d, 1H, J=5.4 Hz), 3.36 (s, 3H), 3.13 (s, 3H), 3.10 (m, 2H).

Anal. Calcd for $C_{22}H_{22}N_4O_4$: C, 65.01; H, 5.46; N, 13.78. Found: C, 64.92; H, 5.60; N, 13.78.

EXAMPLE 10A

5-Cyano-1H-indole-2-carboxylic acid

5-Cyano-1H-indole-2-carboxylic acid ethyl ester (1.71 g, 8.0 mmol) was added to a solution of ethanol (10 mL) and potassium hydroxide (2 g) and the resulting mixture heated at reflux for 1 hour. Water was added to dissolve the precipitate, and 6N HCl was added to bring the pH to 1. A precipitate formed. The mixture was cooled in an ice bath, filtered, and the resulting colorless solid washed with cold water and dried (1.51 g). A portion (1.4 g) was suspended in hot acetic acid (40 mL) and cooled giving a solid which was filtered, washed with cold ethyl acetate and dried: Yield 980 mg 70%; HPLC (60/40) 3.09 minutes (97%).

EXAMPLE 10B

5-Cyano-1H-indole-2-carboxylic acid ethyl ester

Zinc dust (57.8 g, 887 mmol) was added to a hot suspension of 3-cyano-5-nitrophenylpyruvic acid ethyl ester (23.2 g, 88 mmol) in acetic acid (225 mL) and water (225 mL, Caution!, vigorous initial exotherm) at a rate to maintain reflux, and the reaction was held at reflux for 0.5 hours. The mixture was filtered, the filtered salts washed with hot acetic acid (150 mL), and the filtrate chilled overnight giving crystals which were filtered, washed with cold 1:1 acetic acid-water, water, and dried (10.11 g, 53%). The filtrate was concentrated, the residue dissolved in ethyl acetate, and the resulting solution washed with saturated aqueous sodium bicarbonate, brine, dried and concentrated giving a second batch (5.05 g).

The major lot was used in subsequent transformations.

EXAMPLE 10C

3-Cyano-5-nitrophenylpyruvic acid ethyl ester

A solution of sodium ethoxide in ethanol (from 2.2 g, 400 mmol sodium metal in 400 ml ethanol) was added at 0° C. to a mixture of distilled diethyl oxalate (120 g, 821 mmol) and 3-methyl-4-nitrobenzonitrile (32 g, 197 mmol). The resulting red solution was heated at 40° C. for 18 hours. The cooled mixture was diluted with water (600 mL) and acidified with conc. HCl to pH 2.1. The precipitate that formed was collected by filtration of the 13° C. mixture, dried and purified by chromatography on silica eluted with 15, 30 and 50% acetone-hexanes giving an orange solid which was used without purification (23.6 g, 31%).

EXAMPLE 11

5-Methyl-1H-indole-2-carboxylic acid {(1S)-[(R)-hydroxy-(methoxy-methyl-carbamoyl)-methyl]-2-phenyl-ethyl}-amide (3S)-Amino-(2R)-hydroxy-N-methoxy-N-methyl-4-phenyl-butyramide hydrochloride (0.5 mmol) and 5-methyl-1H-indole-2-carboxylic acid (0.5 mmol) were coupled according to Procedure A (reaction temperature 0–25° C., extraction with acid first, then base) and the product purified by chromatography on silica in 20–50% ethyl acetate-hexanes: Yield, 75%; HPLC (60/40) 5.06 minutes (99%); PBMS 396 (MH+, 100%);

$^1$H NMR (CDCl$_3$) δ9.14 (br, 1H), 7.4–7.2 (m, 6H), 7.07 (dd, 1H, J=2, ca 8 Hz), 6.76 (d,1H, J=2 Hz), 6.45 (d, 1H, J=9.7 Hz), 4.90 (m, 1H), 4.29 (d, 1H, J=5.5 Hz), 3.83 (d, 1H, J=5.5 Hz), 3.35 (s, 3H), 3.13 (s, 3H), 3.09 (dd, 1H, J=6, 13 Hz), 3.00 (dd, 1H, J=9, 13 Hz), 2.42 (s, 3H).

Anal. Calcd for C$_{22}$H$_{25}$N$_3$O$_4$: C, 66.82; H, 6.37; N, 10.18. Found: C, 66.97; H, 6.48; N, 10.33.

EXAMPLE 12

5-Fluoro-1H-indole-2-carboxylic acid {(1S)-[(R)-hydroxy-(methoxy-methyl-carbamoyl)-methyl]-2-phenyl-ethyl}-amide (3S)-Amino-(2R)-hydroxy-N-methoxy-N-methyl-4-phenyl-butyramide hydrochloride (0.5 mmol) and 5-fluoro-1H-indole-2-carboxylic acid (0.5 mmol) were coupled according to Procedure A (washing first with acid then base) and the product purified by chromatography on silica gel eluted with 20–50% ethyl acetate in hexanes: Yield, 69%; HPLC (60/40) 4.55 minutes (95%); PBMS 400 (MH+, 100%);

$^1$H NMR (CDCl$_3$) δ9.34 (br, 1H), 7.4–7.2 (m, 7H), 7.00 (dt, 1H, J=2.5, 9.1 Hz), 6.80 (d, 1H, J=1.6 Hz), 6.48 (d, 1H, J=9.5 Hz), 4.93 (m, 1H), 4.30 (d, 1H, J=5.3 Hz), 3.83 (d, 1H, J=5.3 Hz), 3.35 (s, 3H), 3.14 (s, 3H), 3.08 (dd, 1H, A of AB), 3.02 (dd, 1H, J=5, 11 Hz, B of AB).

Anal. Calcd for C$_{21}$H$_{22}$FN$_3$O$_4$: C, 63.15; H, 5.55; N, 10.52. Found: C, 64.19; H, 6.07; N, 10.91.

EXAMPLE 13

1H-indole-2-carboxylic acid {(1S)-[(R)-hydroxy-(methoxy-methyl-carbamoyl)-methyl]-2-phenyl-ethyl}-amide (3S)-Amino-(2R)-hydroxy-N-methoxy-N-methyl-4-phenyl-butyramide hydrochloride (0.26 mmol) and 1H-indole-2-carboxylic acid (0.28 mmol) were coupled according to Procedure A (0–25° C. reaction temperature) and the product purified by chromatography on silica gel eluted with 20–50% ethyl acetate in hexanes: Yield, 87%; HPLC (60/40) 4.26 minutes (96%); PBMS 382 (MH+, 100%);

$^1$H NMR (CDCl$_3$) δ9.24 (br, 1H), 7.63 (d, 1H, J=8.0 Hz), 7.4–7.15 (m, 8H), 7.11 (dt, 1H, J=8.0, 1.5 Hz), 6.85 (d, 1H, J=1.5 Hz), 6.48 (d, 1H, J=9.8 Hz), 4.94 (m, 1H), 4.30 (d, 1H, J=5.5 Hz), 3.84 (d, 1H, J=5.4 Hz), 3.36 (s, 3H), 3.14 (s, 3H), 3.09 (dd, 1H, J=6, 13 Hz, A of AB), 3.03 (dd, 1H, J=10, 13 Hz, B of AB).

Anal. Calcd for C$_{21}$H$_{23}$N$_3$O$_4$: C, 66.13; H, 6.08; N, 11.02. C, 66.19; H, 6.08; 11.02.

EXAMPLE 14

5-Chloro-1H-indole-2-carboxylic acid {(1S)[(methoxy-methyl-carbamoyl)-methyl]-2-phenyl-ethyl}-amide (3S)-[(5-Chloro-1H-indole-2-carbonyl)-amino]-4-phenyl-butyric acid (357 mg, 1.0 mmol) and N,O-dimethylhydroxylamine hydrochloride, 98% (98 mg, 1.0 mmol) were coupled according to procedure A (dimethylformamide solvent). The foam obtained was triturated with ether, the sticky solid dissolved in dichloromethane, concentrated and triturated with hexanes: yield 215 mg, 54%; HPLC (60/40) 6.38 minutes (98%) ;PBMS 400/402 (MH+, 100%);

Anal. Calcd for C$_{21}$H$_{22}$ClN$_3$O$_3$: C, 63.08; H, 5.55; N,10.51. Found: C, 62.91; H, 5.79; N, 10.21.

EXAMPLE 14A (3S)-[(5-Chloro-1H-indole-2-carbonyl)-amino]-4-phenyl-butyric acid 2N NaOH (3.0 mL) was added to a suspension of (3S)-[(5-chloro-1H-indole-2-carbonyl)-amino]-4-phenyl-butyric acid methyl ester (1.28 g, 3.45 mmol) in methanol (10 mL) at 25° C. After 18 hours the reaction mixture was diluted with tetrahydrofuran (10 mL), the solution heated to reflux for 10 minutes, and concentrated. The resulting solid was stirred with 6N HCl for 15 minutes, the suspension filtered, and the resulting solid washed with 2N HCl and dried: yield 1.15 g, 93%; HPLC (60/40) 5.18 minutes (100%);

EXAMPLE 15

(3S)-[(5-Chloro-1H-indole-2-carbonyl)-amino]-(2R)-hydroxy-4-phenylbutyric acid methyl ester 1-(3-dimethylaminopropyl)3-ethylcarbodiimide hydrochloride (DEC, 71 g, 370 mmol) was added to a mixture of (3S)-amino-(2R)-hydroxy-4-phenyl-butyric acid methyl ester (WO 93/25574, Example 1A, 77.5 g, 370 mmol), 5-chloro-1H-indole-2-carboxylic acid (72.45 g, 370 mmol) and 1-hydroxybenzotriazole hydrate in dichloromethane (640 mL) at 25° C. The resulting mixture was stirred for 18 hours, concentrated, the residue dissolved in ethyl acetate, the resulting solution washed twice with 2N NaOH, twice with 1N HCl, brine, dried, and concentrated giving the substance as a yellow foam (140.7 g, 98%) which was used in the subsequent hydrolysis described herein without purification (HPLC (70/30) 3.61 minutes (82%), 9.57 minutes (13%)). A pure sample was obtained by chromatography on silica in ethyl acetate-hexanes, mp 180–183° C.;

$^1$H NMR (CDCl$_3$) δ9.52 (br, 1H), 7.55 (d, 1H, J=2 Hz), 7.35–7.15 (m, 7H), 6.70 (d, 1H, J=2 Hz), 6.50 (d, 1H, J=10 Hz), 4.82 (m, 1H), 4.22 (s, 1H), 3.72 (s, 3H), 3.4 (br, 1H), 3.05 (m, 2H).

$^{13}$CNMR (CDCl$_3$, 75.5 mHz) δ174.2, 164.4, 137.1, 135.0, 131.1, 129.8, 128.8, 128.3, 127.0, 126.2, 125.0, 121.0, 113.2, 102.3, 70.4, 43.3, 43.1, 38.1. TSPMS 387/389 (MH+, 100/30%)

Anal. Calcd for C$_{20}$H$_{19}$ClN$_2$O$_4$+0.5H$_2$O: C, 60.69; H, 5.09; N, 7.08. Found: C, 60.38; H, 4.98; N, 6.86.

EXAMPLE 16

3-[(5-Chloro-1H-indole-2-carbonyl)-amino]-(2RS)-hydroxy-propionic acid (RS)-3-amino-2-hydroxypropionic acid methyl ester hydrochloride (6.6 mmol) and 5-chloro-1H-indole-2-carboxylic acid (6.6 mmol) were coupled according to Procedure A (except that acid, then base extraction was performed, and during the first acid wash a precipitate appeared so the mixture was filtered and the filtrate carried on in the usual manner of Procedure A). The crude product (920 mg) was dissolved in methanol and treated with 1N NaOH (6.6 mL) for 2 hours at 25° C. 1N NaOH was added (6.6 mL) and the mixture was concentrated, the residue dissolved in ethyl acetate, and the resulting solution washed with 2N HCl, brine, dried, and concentrated. The resulting colorless solid was stirred in chloroform and filtered giving the title substance: Yield 763 mg, 40%; HPLC (60/40) 2.86 minutes (89%); mp 214–215° C.; PBMS 283/285 (MH+, 100%); $^1$H NMR (DMSO-d$_6$) δ11.78 (s, 1H), 8.62 (t, 1H), 7.70 (d, 1H, J=2 Hz), 7.42 (d, 1H, J=8.7 Hz), 7.17 (dd, 1H, J=2, 8.7 Hz), 7.14 (d, 1H, J=2 Hz), 4.18 (dd, 1H, J=5, 8 Hz), 3.58 (m, 2H).

Anal. Calcd for $C_{12}H_{11}ClN_2O_4+0.1H_2O$: C, 50.66; H, 3.97; N, 9.85. Found: C, 50.80; H, 4.06; N, 9.48.

EXAMPLE 16A (RS)-3-amino-2-hydroxypropionic acid methyl ester hydrochloride

A mixture of D,L-isoserine (2.06 g, 19.6 mmol), methanol (20 mL) and chlorotrimethylsilane (9.5 g, 88 mmol) was heated at reflux for 5 hours, cooled and concentrated giving the title substance (3.20 g).

EXAMPLE 17

5-Chloro-1H-indole-2-carboxylic acid [(1S)-((R)-methoxy-methylcarbamoyl-methyl)-2-phenyl-ethyl]-amide (3S)-Amino-(2R)-methoxy-N,N-dimethyl-4-phenyl-butyramide hydrochloride (0.84 mmol) and 5-Chloro-1H-indole-2-carboxylic acid (0.80 mmol) were coupled according to Procedure A (0–25° C. reaction temperature, 2:1 dichloromethane-dimethylformamide solvent) and the product purified by chromatography on silica eluting with 1:1 ethyl acetate-hexanes: Yield, 81%; HPLC (60/40) 5.44 minutes (100%); TSPMS 414/416 (MH+, 100/30%);

$^1$H NMR (CDCl$_3$) δ9.38 (br, 1H), 7.60 (d, 1H, J=2 Hz), 7.4–7.2 (m, 6H), 7.20 (dd, 1H, J=2, 9 Hz), 7.03 (d, 1H, J=8 Hz), 6.92 (d, 1H, J=2 Hz), 4.50 (m, 1H), 4.00 (d, 1H, J=2 Hz), 3.40 (s, 3H), 3.22 (dd, A of AB, 1H, J=5, 13 Hz), 3.00 (dd, B of AB, 1H, J=10, 13 Hz), 2.86 (s, 3H), 2.65 (s, 3H).

Anal. Calcd for $C_{22}H_{24}ClN_3O_3$: C, 63.48; H, 5.84; N, 10.15. Found: C, 63.48; H, 5.97; N, 9.97.

EXAMPLE 17A (3S)-Amino-(2R)-methoxy-N,N-dimethyl-4-phenyl-butyramide hydrochloride (1S,2R)-(1-Benzyl-2-dimethylcarbamoyl-2-methoxy-ethyl)-carbamic acid tert-butyl ester (283 mg, 0.84 mmol) was dissolved in 4N HCl-dioxane (1 mL) for 1.5 hours at 25° C., concentrated and the residue coevaporated with ether and dried.

EXAMPLE 17B (1S,2R)-(1-Benzyl-2-dimethylcarbamoyl-2-methoxy-ethyl)-carbamic acid tert-butyl ester Sodium hydride-oil dispersion (53 mg of 50%) was added to a solution of (1S,2R)-(1-benzyl-2-dimethylcarbamoyl-2-hydroxy-ethyl)-carbamic acid tert-butyl ester (322 mg, 1.0 mmol) in tetrahydrofuran (4 mL) at 0° C. After effervescence ceased (several minutes), methyl iodide (155 mg) was added, and after 15 minutes another 11 mg NaH dispersion and 23 mg methyl iodide were added. After 15 more minutes aqueous ammonium chloride solution and ethyl acetate were added, and the organic layer was separated, washed with water, 2N NaOH, dried and concentrated giving a viscous oil which was used without further purification: Yield 283 mg, 84%.

EXAMPLE 17C (1S,2R)-(1-Benzyl-2-dimethylcarbamoyl-2-hydroxy-ethyl)-carbamic acid tert-butyl ester (3S)-tert-Butoxycarbonylamino-(2R)-hydroxy-4-phenyl-butyric acid (Schweizerhall, Inc., S. Plainfield, N.J., 1.02 g, 3.4 mmol) and dimethylamine hydrochloride (338 mg, 4.1 mmol) were coupled according to Procedure A (0–25° C., dimethylformamide-dichloromethane solvent, acid, then base extraction) giving crude product which was chromatographed on silica eluted with 1–8% ethanol in dichloromethane: Foam; Yield 995 mg, 91%;

EXAMPLE 18

5-Chloro-1H-indole-2-carboxylic acid (3-azetidin-1-yl-(1S)-benzyl-(2R)-hydroxy-3-oxo-propyl)-amide Azetidine (0.44 mmol) and (3S)-[(5-chloro-1H-indole-2-carbonyl)-amino]-(2R)-hydroxy-4-phenyl-butyric acid (0.4 mmol) were coupled according to Procedure A (1:1 dimethylformamide-dichloromethane solvent) giving the title substance: Yield 94%; HPLC (60/40) 4.55 minutes (>98%); PBMS 412/414 (MH+, 100%);

Anal. Calcd for $C_{22}H_{22}ClN_3O_3+0.25 H_2O$: C, 63.46; H, 5.45; N, 10.09. Found: C, 63.61; H, 5.66; N, 10.27.

EXAMPLE 19

5-Chloro-1H-indole-2-carboxylic acid [(1S)-benzyl-(2R)-methoxy-2-(methoxy-methyl-carbamoyl)-ethyl]-amide (3S,2R)-3-Amino-(2R),N-dimethoxy-N-methyl-4-phenyl-butyramide (0.31 mmol) and 5-chloro-1H-indole-2-carboxylic acid (0.31 mmol) were coupled according to Procedure A and the product purified by chromatography on silica gel in 20–40% ethyl acetate-hexanes: Yield 81%; HPLC (60/40) 7.39 minutes (98%); PBMS 430/432 (MH+, 100%);

$^1$H NMR (CDCl$_3$) δ9.44 (s, 1H), 7.58 (d, 1H, J=ca. 2 Hz), 7.4–7.22 (m, 6H), 7.19 (dd, 1H, J=2.0, 8.8 Hz), 6.89 (d, 1H, J=ca. 2Hz), 6.80 (d, 1H, J=8 Hz), 4.72 (m, 1H), 3.93 (s, 1H), 3.39 (s, 3H), 3.24 (s, 3H), 3.19 (dd, 1H, J=5.1, 13 Hz, A of AB), 3.06 (s, 3H), 2.95 (dd, 1H, J=10.9, 13 Hz, B of AB).

Anal. Calcd for $C_{22}H_{24}ClN_3O_4+0.33C_6H_{14}$: C, 62.85; H,6.30; N, 9.16. Found: C, 62.91; H, 6.29; N, 8.95.

EXAMPLE 19A (3S,2R)-3-Amino-(2R), N-dimethoxy-N-methyl-4-phenyl-butyramide (1S,2R)-(1-Benzyl-2-methoxy-methyl-carbamoyl-2-methoxy-ethyl)-carbamic acid tert-butyl ester (113 mg, 0.32 mmol) was dissolved in 4N HCl-dioxane (4 mL) at 25° C. for 1 hour, concentrated, and the residue triturated with ether giving the title product (93 mg, 100%).

EXAMPLE 19B (1S,2R)-(1-Benzyl-2-methoxy-methyl-carbamoyl-2-methoxy-ethyl)-carbamic acid tert-butyl ester Sodium hydride dispersion (30 mg of 50% in oil) was added to a solution of (1S,2R)-(1-Benzyl-2-methoxy-methyl-carbamoyl-2-hydroxy-ethyl)-carbamic acid tert-butyl ester in tetrahydrofuran (2 mL) at 0° C. After 5 minutes methyl iodide (175 mg) was added and the mixture was allowed to stand at 25° C. for 18 hour. Ethyl acetate and saturated aqueous ammonium chloride solution were added and the organic layer was separated, washed with water, dried, concentrated, and chromatographed on silica eluting with 10–20% ethyl acetate-hexanes: Yield 113 mg, 52%; HPLC (60/40) 6.45 minutes (>96%).

EXAMPLE 20

[(2S)-[(5-Chloro-1H-indole-2-carbonyl)-amino]-(1R)-(methoxy-methyl-carbamoyl)-3-phenyl-propoxy]-acetic acid benzyl ester (1R,2S)-[2-Amino-1-(methoxy-methyl-carbamoyl)-3-phenyl-propoxy]-acetic acid benzyl ester hydrochloride (162 mg, 0.38 mmol) was coupled with 5-chloro-1H-indole-2-carboxylic acid (71 mg, 0.36 mmol) according to Procedure A (0–25° C. reaction temperature) and the crude product purified by chromatography on silica gel eluting with 20–75% ethyl acetate in hexane giving the title substance as a glassy solid: Yield, 61%; TSPMS 564/566 (MH+, 90/60%), 581/583 (MH+NH3, 100/50%).

EXAMPLE 20A (1R,2S)-[2-Amino-1-(methoxy-methyl-carbamoyl)-3-phenyl-propoxy]-acetic acid benzyl ester hydrochloride (1R,2S)-[2-tert-Butoxycarbonylamino-1-(methoxy-methyl-carbamoyl)-3-phenyl-propoxy]-acetic acid benzyl ester (170 mg, 0.35 mmol) was dissolved in 4N HCl-dioxane (2 mL) for 1.5 hours at 25° C., concentrated, the residue coevaporated with ether and dried giving an oil (163 mg). MS 387 (MH+, 100%).

EXAMPLE 20B (1R,2S)-[2-tert-Butoxycarbonylamino-1-(methoxy-methyl-carbamoyl)-3-phenyl-propoxy]-acetic acid benzyl ester Sodium hydride dispersion (120 mg of 50% in oil, 2.8 mmol) was added to a solution of (1S,2R)-(1-benzyl-2-methoxy-methyl-carbamoyl-2-hydroxy-ethyl)-carbamic acid tert-butyl ester (858 mg, 2.5 mmol) in tetrahydrofuran (8 mL) at 0° C. After effervescence ceased benzyl bromoacetate (0.56 g, 2.5 mmol) was added and the mixture was brought to 25° C. After 2 hours more NaH dispersion was added (12 mg), and the mixture was stirred 1 hour, diluted with ethyl acetate and saturated ammonium chloride, the organic layer separated, washed with water, dried, and concentrated giving an oil which was chromatographed on silica gel eluted with 20–75% ethyl acetate-hexanes. The most pure fractions were combined giving an oil (175 mg, 15%): MS 487 (MH+), 387 (100%).

EXAMPLE 21

[(2S)-[(5-Chloro-1H-indole-2-carbonyl)-amino]-(1R)-(methoxy-methyl-carbamoyl)-3-phenyl-propoxy]-acetic acid A mixture of [(2S)-[(5-chloro-1H-indole-2-carbonyl)-amino]-(1R)-(methoxy-methyl-carbamoyl)-3-phenyl-propoxy]-acetic acid benzyl ester (120 mg, 0.2 mmol) and 50% moist palladium hydroxide on carbon catalyst in methanol (50 mL) was shaken at 40 p.s.i. hydrogen pressure and 25° C. for 1 hour. The mixture was allowed to stand for 30 min, then filtered through a filter aid and the filtrate concentrated giving 121 mg of a solid which was chromatographed on silica and eluted with 25–100% ethyl acetate-hexanes giving 84 mg of a solid, HPLC (60/40) 4.81 (37%) and 6.24 minutes (63%). $^1$H NMR and MS analysis showed these to be methyl esters of the 5-des-Cl and title product respectively. This solid was dissolved in THF and treated with 1N NaOH (170 uL) for 30 minutes at 25° C., the solution concentrated, and the residue partitioned between ethyl acetate and 1N HCl. The organic layer was separated, washed with water, dried, and concentrated giving a mixture of the title substance and the des-5-Cl analog: Yield 85 mg, 71%; HPLC (60/40) 3.49 minutes (37%), 4.23 minutes (61%); MS 338 (MH+, 100%); TSPMS 474/476 (MH+for title substance, 40%), 440 (MH+for des-Cl analog, 95%);

EXAMPLE 22

(3S)-[(1H-indole-2-carbonyl)amino]-(2R)-hydroxy-4-phenylbutyramide (2R,3S)-3-amino-2-hydroxy-4-phenylbutyramide (0.59 mmol, U.S. Pat. No. 4,599,198 Example 1D) and indole-2-carboxylic acid (0.71 mmol) were coupled according to Procedure A (washing with acid, then base) and the resulting product purified by chromatography on silica by eluting with 66–100% ethyl acetate-hexanes: Yield 89%; HPLC (60/40, Dupont Zorbax C-8 column) 99%; MS 338 (MH+, 100%). 1H 1H NMR (DMSO-d6) δ11.53 (s, 1H), 7.95 (d, 1H, J=9 Hz), 7.63 (d, 1H, J=8 Hz), 7.5–7.15 (m, 7–8 Hz), 7.12 (d, 1H, J=ca. 7 Hz), 7.09 (d, 1H, J=ca. 8 Hz), 5.95 (d, 1H, J=6 Hz), 4.55 (m, 1H), 3.93 (m, 1H), 2.98 (dd, 1H, A of AB, J=6, 13 Hz), 2.88 (dd, 1H, B of AB, J=8, 13 Hz).

EXAMPLE 23

(3S)-[(5-Chloro-1H-indole-2-carbonyl)amino]-(2S)-hydroxy-4-phenylbutyramide

5-Chloro-1H-indole-2-carbonyl fluoride (0.30 g, 1.29 mmol) was added to a solution of (2S,3S)-3-amino-2-hydroxy-4-phenyl-butyramide hydrochloride (0.319 g, 1.61 mmol) and triethylamine (145 mg, 1.42 mmol) in dichloromethane (2 mL) at 25° C. After 18 hours the mixture was diluted with ethyl acetate, the resulting solution washed twice with 1N HCl, twice with saturated aqueous NaHCO$_3$, once with brine, dried, concentrated, and the residue chromatographed on silica eluted with 50–100% ethyl acetate-hexanes giving a solid (0.31 g) which was recrystallized from isopropyl alcohol: Yield 0.020 g; FABMS 372/374 (MH+, 21%), 217 (100%). $^1$H NMR (DMSO-d$_6$, partial) δ8.5 (d, 1H, J=9 Hz), 7.48 (d, 1H, J=2 Hz), 7.4–7.1 (m, 9H), 5.95 (d, 1H, J=7 Hz), 4.56 (m, 1H), 4.08 (m, 1H), 2.92 (dd, 1H, J=11, 13 Hz), 2.68 (dd, J=3, 13 Hz).

EXAMPLE 23A

5-Chloro-1H-indole-2-carbonyl fluoride

A solution of 5-chloro-1H-indole-2-carboxylic acid (10.0 g, 51.1 mmol) and pyridine (33.1 mmol) in acetonitrile was added to a solution of cyanuric fluoride (2.76 g, 20.4 mmol) in acetonitrile (total 340 mL) at 25° C. The reaction was followed by TLC on aliquots quenched with butylamine and appeared nearly complete at 1 hour. The mixture was poured onto ice, extracted with ether, dried (Na$_2$SO$_4$), and concentrated giving a solid which was used without purification (10.0 g, 99%). TLC of a butylamine-quenched aliquot showed some 5-chloroindole-2-carboxylic acid and the less polar N-butylamide. A sample was purified by chromatography on silica gel eluting with ethyl acetate-hexanes (50–100%) for characterization (16368-130-1).

EXAMPLE 23B (2S,3S)-3-Amino-2-hydroxy-4-phenyl-butyramide hydrochloride

[(1S)-((S)-Carbamoyl-hydroxy-methyl)-2-phenyl-ethyl]-carbamic acid tert-butyl ester (0.50 g, 1.7 mmol) was dissolved in 4 M HCl-dioxane at 25° C. for 1 hour. The mixture was concentrated and the residue triturated with ether and dried giving a colorless solid (430 mg): HPLC (60/40) 2.68 min, 100%.

EXAMPLE 23C

[(1S)-((S)-Carbamoyl-hydroxy-methyl)-2-phenyl-ethyl]-carbamic acid tert-butyl ester Tetrabutylammonium fluoride (23 mL of 1M in tetrahydrofuran) was added to a solution of {(1S)-[(S)-(tert-butyl-dimethyl-silanyloxy)-carbamoyl-methyl]-2-phenyl-ethyl}-carbamic acid tert-butyl ester in tetrahydrofuran (6 mL) at 0° C. After 30 minutes the mixture was diluted with ethyl acetate and water, the organic layer separated, washed with water, 2×1N HCl, 2×1N NaHCO$_3$, and brine. An emulsion was obtained which was filtered through a filter acid, the filtrate dried, and concentrated giving a colorless solid (0.5 g, 20%). A portion (3.1 g) of the filtered solid (3.3 g) was recrystallized from hot ethyl acetate with hot filtration giving a colrless solid (1.33 g).

EXAMPLE 23D

{(1S)-[(S)-(tert-Butyl-dimethyl-silanyloxy)-carbamoyl-methyl]-2-phenyl-ethyl}-carbamic acid tert-butyl ester 30% hydrogen peroxide (7.2 mL, 64 mmol) was added over a period of 15 minutes to a solution of [1(S)-benzyl-(2S)-(tert-butyl-dimethyl-silanyloxy)-2-cyano-ethyl]-carbamic acid tert-butyl ester (Example 24D, 5.0 g, 12.8 mmol) and 1N NaOH (22 mL) in ethanol (110 mL) at 0° C. The mixture was stirred 1.5 hours, treated with aqueous 10% sodium thiosulfate solution (175 mL), concentrated, and extracted with ethyl acetate. The extracts were dried over Na$_2$SO$_4$ and concentrated. The residue was chromatographed on silica eluted with 20–33% ethyl acetate hexanes giving the title substance as a colorless solid (3.17 g, 61%).

EXAMPLE 24

5-Chloro-1H-indole-2-carboxylic acid {(1S)-[(S)-hydroxy-(methoxy-methyl-carbamoyl)-methyl]-2-phenyl-ethyl}-amide N,O-Dimethylhydroxylamine hydrochloride (0.4 mmol) and (3S)-[(5-Chloro-1H-indole-2-carbonyl)amino]-(2S)-hydroxy-4-phenylbutyric acid (0.38 mmol) were coupled according to Procedure A and the product purified by chromatography on silica eluted with 20–50% ethyl acetate-hexanes: Yield, 72%; HPLC (60/40) 5.05 min, 98%; PBMS 416/418 (MH+, 100%);

$^1$H NMR (CDCl$_3$) δ9.30 (br, 1H), 7.60 (d, 1H, J=2 Hz), 7.33 (d, 1H, J=8 Hz), 7.3–7.15 (m, 6–7H), 6.75 (m, 2H), 5.00 (m, 1H), 4.65 (d, 1H, J=4 Hz), 3.71 (s, 3H), 3.06 (s, 3H), 2.87 (m, 2H), 1.6 (br).

Anal. Calcd for C$_{21}$H$_{22}$ClN$_3$O$_4$+0.35H$_2$O: C, 59.74; H, 5.42; N, 9.95. Found: C, 60.14; H, 5.65; N, 9.55.

EXAMPLE 24A (3S)-[(5-Chloro-1H-indole-2-carbonyl)amino]-(2S)-hydroxy-4-phenylbutyric acid Aqueous 1N NaOH (2.6 mL) was added to a solution of (3S)-[(5-Chloro-1H-indole-2-carbonyl)amino]-(2S)-hydroxy-4-phenylbutyric acid methyl ester (500 mg, 1.29 mmol) in methanol at 25° C. After 18 hours the mixture was concentrated, the residue dissolved in ethyl acetate and water, and the resulting solution acidified to pH 1 with 6N HCl. The aqueous layer was separated, extracted three times with ethyl acetate, the organic layers combined, dried and concentrated giving a solid (417 mg, 87%): HPLC (60/40) 4.23 (>98%).

EXAMPLE 24B ((3S)-[(5-Chloro-1H-indole-2-carbonyl)-amino]-(2S)-hydroxy-4-phenyl-butyric acid methyl ester (3S)-Amino-(2S)-hydroxy-4-phenyl-butyric acid methyl ester (1.4 mmol) and 5-Chloro-1H-indole-2-carboxylic acid (1.37 mmol) were coupled according to Procedure A (0–25° C. reaction, 40 hour reaction time, 1:1 dichloromethane-dimethylformamide solvent) giving the title product: Yield, 94%; HPLC (60/40) 5.38 minutes (97%); mp 214–221 ° C.; PBMS 387/389 (MH+, 100%);

Anal. Calcd for C$_{20}$H$_{19}$ClN$_2$O$_4$: C, 62.10; H, 4.95; N, 7.24. Found: C, 62.16; H, 5.07; N, 7.11.

EXAMPLE 24C (3S)-Amino-(2S)-hydroxy-4-phenyl-butyric acid methyl ester

[1(S)-Benzyl-(2S)-(tert-butyl-dimethyl-silanyloxy)-2-cyano-ethyl]-carbamic acid tert-butyl ester (417 mg) was added to a solution of anhydrous HCl (3.2g) in methanol (20 mL) and the resulting solution capped and kept at 25° C. for 5 days. The mixture was concentrated to give 308 mg of colorless solid which was homogeneous by $^1$H NMR (D$_2$O). This material was combined with spectrally equivalent material prepared in the same manner from 400 mg of the same precursor, and together the mixture was dissolved in saturated aqueous NaHCO$_3$ which was extracted ten times with chloroform. The combined extracts were dried and concentrated giving the title substance (328 mg, 75%):

EXAMPLE 24D

[1(S)-Benzyl-(2S)-(tert-butyl-dimethyl-silanyloxy)-2-cyano-ethyl]-carbamic acid tert-butyl ester N-t-butoxycarbonyl-(3S)-amino-(2RS)-hydroxy-4-phenylbutyronitrile was converted to the corresponding O-tert-butyldimethylsilyl ethers by the procedure described in U.S. Pat. No. 4,599,198, Example 1B, and the isomers separated by silica gel chromatography (7%–8% ether-hexanes). The title substance was thereby separated from its slightly less polar 2R isomer (the latter Example 1B in U.S. Pat. No. 4,599,198).

EXAMPLE 24E

N-t-Butoxycarbonyl-(3S)-amino-(2RS)-hydroxy-4-phenylbutyronitrile

A 5° C. solution of sodium bisulfite (4.38 g) in water (100 mL) was added to a solution of N-t-butoxycarbonyl-L-phenylalaninal (J. Med. Chem 1985, vol. 28, 1779–1790, 10.0 g, 40.1 mmol) in dimethoxyethane (100 mL) at 0–5° C. The mixture was stirred for 2 hours at 0° C. and then at 25° C. overnight. The mixture was concentrated to 80 mL volume, diluting with ethyl acetate (250 mL), and the resulting solution treated with potassium cyanide (2.61 g, 40.1 mmol). After 4 hours at 25° C. the organic layer was separated, washed twice with water, once with brine, dried and concentrated. The resulting oil was crystallized from ether/hexanes giving a colorless solid (3.53 g): mp 95–98° C. A second crop was obtained by recrystallizing the mother liquor (5.0 g) with ether/hexanes (colorless solid, 2.44 g): mp 88–92° C. The latter, lower-melting material was used in the subsequent silylation transformation described herein.

EXAMPLE 25

(3S)-[(5-Chloro-1H-indole-2-carbonyl)amino]-(2R)-hydroxy-4-phenylbutyric acid

Aqueous 2N NaOH (375 mL) was added at 10–22° C. to a solution of crude (3S)-[(5-chloro-1H-indole-2-carbonyl)-amino]-(2R)-hydroxy-4-phenyl-butyric acid methyl ester (containing 13% of the N,O-bis-5-chloro-1H-indole-2-carbonyl impurity, 140.7 g, 363 mmol) in methanol (1900 mL) and the mixture was allowed to stir at 25° C. After 2 hours the solution was concentrated and the residue dissolved in ethyl acetate (2L) and 2N HCl (500 mL). The aqueous layer was separated and washed twice with 2N HCl, and the organic layers were combined, washed with brine, dried over $Na_2SO_4$ and concentrated. The residue (137.6 g) was consolidated in 100 mL hot ethyl acetate (suspension), chloroform (1300 mL) was added, and the resulting suspension heated at reflux with mechanical stirring for 5 min, filtered hot, and the filtered solid washed with near-boiling chloroform-ethyl acetate (3:1, 400 mL). The resulting solid was dried in vacuo to constant weight (101 g, 75%). The filtrate was concentrated and recrystallized by dissolving in hot tetrahydrofuran (70 mL), adding hot hexanes (200 mL), cooling overnight, and filtering and washing the resulting solid with THF-hexanes (1:5), giving 7.03 g (5%). The mother liquors from the latter operation were concentrated, and recrystallized according to the same procedure giving 11.07 g (8%). All three lots showed HPLC (60/40) 4.2 minutes (>98%). Analysis of 5-chloro-1H-indole-2-carboxylic acid content was accomplished by HPLC (C8 Zorbax 15 cm column, 600:400:2:1 water-acetonitrile-triethylamine-acetic acid) showing this substance present at 0.4%, 0.7%, and 21%, respectively in the three lots as sequentially described above. For the main lot: mp 209–212° C.; TSPMS 373/375 (MH+100%);

$^1$H NMR (DMSO-$d_6$) δ12.6 (br, 1H), 11.7 (s, 1H), 8.17 (d, 1H, J=9.1 Hz), 7.71 (d, 1H, J=2 Hz), 7.39 (d, 1H, J=8.7 Hz), 7.28 (m, 4H), 7.17 (m, 3H), 5.55 (br, 1H), 4.57 (m, 1H), 4.05 (d, 1H, J=3.6 Hz), 2.97 (dd, 1H, A of AB, J=6.5, 13.5 Hz), 2.87 (dd, 1H, B of AB, J=8.5, 13.5 Hz).

Anal. Calcd for $C_{19}H_{17}ClN_2O_4$: C, 61.21; H, 4.60; N, 7.51. Found: C, 61.09; H, 4.63; N, 7.59.

EXAMPLE 26

(3R)-[(5-Fluoro-1H-indole-2-carbonyl)-amino]-(2R)-hydroxy-4-phenyl-butyric acid

A solution of (3S)-[(5-fluoro-1H-indole-2-carbonyl)-amino]-(2R)-hydroxy-4-phenyl-butyric acid methyl ester (190 mg, 0.5 mmol), 1N NaOH (1 mL) and methanol (5 mL) was stirred at 25° C. for 18 hours. The pH was adjusted to 1–2 with 1N HCl, the solution concentrated, and the solids ground up under water at 25° C. and filtered. The resulting solid was washed with ether and dried giving a colorless glass (160 mg, 87%): HPLC (60/40) 3.49 minutes (99%); $^1$H NMR (partial, DMSO-$d_6$) δ8.15 (d, 1H, J=8 Hz), 7.42 (m, 2H), 7.3 (m, 4H), 7.15 (m, 2H), 7.03 (dt, 1H), 4.60 (m, 1H), 4.03 (d, 1H), 3.00 (dd, 1H, J=8, 13 Hz), 2.90 (dd, 1H, J=8, 13 Hz).

EXAMPLE 27

(3S)-[(5-Bromo-1H-indole-2-carbonyl)-amino]-(2R)-hydroxy-4-phenyl-butyric acid

Aqueous 1N NaOH (60 mL) was added to a solution of (3S)-[(5-bromo-1H-indole-2-carbonyl)-amino]-(2R)-hydroxy-4-phenyl-butyric acid methyl ester (2.45 g, 5.7 mmol) in methanol (60 mL) at 25° C. After 2 hours the mixture was concentrated and partitioned between ethyl acetate and 2N HCl. The aqueous layer was separated, extracted with ethyl acetate, the combined organic layers washed with 1N HCl, brine, dried, concentrated and the resulting solid triturated with chloroform at 25° C.: Yield 85%, HPLC (60/40) 4.24 minutes (100%); mp 213–216° C.; TSPMS 417/419 (MH+, 98%);

$^1$H NMR (partial, DMSO-$d_6$) δ11.72 (br, 1H), 8.20 (d, 1H, J=10 Hz), 7.86 (d, 1H, J=2 Hz), 7.4–7.1 (m, 8H), 4.60 (m, 1H), 4.04 (d, 1H, J=3.5 Hz), 3.00 (dd, 1H, A of AB, J=7, 13 Hz), 2.88 (dd, 1H, B of AB, J=8.5, 13 Hz).

Anal. Calcd for $C_{19}H_{17}BrN_2O_4+0.25H_2O$: C, 54.11; H, 4.18; N, 6.64. Found: C, 54.15; H, 4.15; N, 6.64.

EXAMPLE 28

(3S)-[(5,6-Dichloro-1H-indole-2-carbonyl)-amino]-(2R)-hydroxy-4-phenyl-butyric acid Aqueous 1N NaOH (1.18 mL) was added to a suspension of (3S)-[(5,6-dichloro-1H-indole-2-carbonyl)-amino]-(2R)-hydroxy-4-phenyl-butyric acid methyl ester (249 mg, 0.6 mmol) in methanol (5 mL) at 25° C. After 18 hours the mixture was concentrated, the residue partitioned between excess 2N HCl and ethyl acetate, the aqueous layer separated and washed with ethyl acetate, the combined organic layers washed with brine, dried and concentrated giving a yellow solid: Yield 259 mg; HPLC (60/40) 4.96 minutes (100%); TSPMS 407/409 (MH+, 100/40%);

$^1$H NMR (partial, DMSO-$d_6$) δ11.8 (br, 1H), 8.28 (d, 1H, J=9 Hz), 7.98 (s, 1H), 7.58 (s, 1H), 7.3–7.15 (m, 6H), 4.60 (m, 1H), 4.07 (d, 1H, J=3–4 Hz), 2.98 (dd, 1H, A of AB, J=6, 13 Hz), 2.88 (dd, 1H, J=9, 13 Hz).

Anal. Calcd for $C_{19}H_{16}Cl_2N_2O_4+0.5H_2O$: C, 54.82; H, 4.12; N, 6.73. Found: C, 54.86; H, 4.08; N, 6.76.

EXAMPLE 29

(3R)-[(5-Chloro-1H-indole-2-carbonyl)-amino]-(2R)-hydroxy-4-phenyl-butyric acid

Aqueous 1N NaOH (1.69 mL) was added to a suspension of (3R)-[(5-Chloro-1H-indole-2-carbonyl)-amino]-(2R)-hydroxy-4-phenyl-butyric acid methyl ester (326 mg, 0.8 mmol) in methanol at 25° C. After 2.5 hours the mixture was concentrated (starting material found) and redissolved in methanol and aqueous 1N NaOH (0.5 mL). After 1 hour the mixture was concentrated and the residue partitioned between excess 2N HCl and ethyl acetate, the organic layer separated, dried and concentrated: Yield 288 mg, 92%; HPLC (60/40) 3.89 minutes (93%); mp 215–223° C.; TSPMS 373/375 (MH+, 100%);

¹H NMR (DMSO-d₆) δ12.7 (br, 1H), 11.65 (s, 1H), 8.50 (d, 1H, J=8.8 Hz), 7.70 (d, 1H, J=2 Hz), 7.37 (d, 1H, J=8.7 Hz), 7.4–7.1 (m, 7H), 5.7 (br, 1H), 4.50 (m, 1H), 4.17 (d, 1H, J=4.8 Hz), 2.94 (dd, 1H, A of AB, J=10, 14 Hz), 2.78 (dd, 1H, B of AB, J=3, 14 Hz).

Anal. Calcd for $C_{19}H_{17}ClN_2O_4+0.1\ H_2O$: C, 60.92; H, 4.63; N, 7.48. Found: C, 60.72; H, 4.78; N, 7.53.

EXAMPLE 29A (3R)-[(5-Chloro-1H-indole-2-carbonyl)-amino]-(2R)-hydroxy-4-phenyl-butyric acid methyl ester (2R,3R)-3-Amino-2-hydroxy-4-phenylbutyric acid methyl ester hydrochloride (239 mg, 1.0 mmol) and 5-chloro-1H-indole-2-carboxylic acid (200 mg, 1.05 mmol) were coupled according to Procedure A (0–25° C., washed with acid, then base) giving crude product which was used without further purification: Yield 328 mg, 87%.

EXAMPLE 29B (2R,3R)-3-Amino-2-hydroxy-4-phenylbutyric acid methyl ester Hydrochloride A mixture of (2R,3R)-3-amino-2-hydroxy-4-phenylbutyric acid (200 mg, 1.0 mmol, Sigma Chemical Co. (St. Louis, Mo.), chlorotrimethylsilane (500 mg, 4.6 mmol) and methanol (2 mL) was heated at reflux for 5.5 hours and concentrated to a foam: Yield 244 mg, 100%.

EXAMPLE 30

5-Chloro-1H-indole-2-carboxylic acid [(2RS)-hydroxy-2-(methoxy-methyl-carbamoyl)-ethyl]-amide N,O-Dimethylhydroxylamine hydrochloride (1.0 mmol) and 3-[(5-chloro-1H-indole-2-carbonyl)-amino]-(2RS)-hydroxy-propionic acid (0.95 mmol) were coupled according to Procedure A (0–25° C., washed with acid, then base) and the crude product triturated with ether giving a colorless solid: Yield 69%; HPLC (60/40) 3.18 minutes (96%); mp 192–192.5° C.; PBMS 326/328 (MH+, 100%);

¹H NMR (DMSO-d₆) δ11.80 (s, 1H), 8.62 (t, 1H), 7.70 (d, 1H, J=2Hz), 7.41 (d, 1H, J=8.8 Hz), 7.17 (dd, 1H, J=2, 8.7 Hz), 7.13 (s, 1H), 5.35 (m, 1H), 4.65 (m, 1H), 3.69 (s, 3H), 3.47 (m, 2H), 3.34 (s, 3H).

Anal. Calcd for $C_{14}H_{16}ClN_3O_4$: C, 51.62; H, 4.95; N, 12.90. Found: C, 51.78; H, 5.07; N, 12.75.

EXAMPLE 31

(3S)-[(5-Chloro-1H-indole-2-carbonyl)amino]-(2R)-hydroxy-4-phenylbutyramide

A large excess of anhydrous ammonia was introduced into a solution of (3S)-[(5-chloro-1H-indole-2-carbonyl)-amino]-(2R)-hydroxy-4-phenyl-butyric acid methyl ester (100 mg, 0.27 mmol) in methanol (10 mL) and the mixture was heated in a stainless steel Parr reactor (<50 p.s.i.) for 48 hours at 70° C. The mixture was cooled, concentrated, and the resulting solid triturated with ether: Yield ca. 60%; HPLC 3.52 minutes (95%); PBMS 372/374 (MH+, 100%);;

¹H NMR (partial, DMSO-d₆) δ11.75 (s, 1H), 8.04 (d, 1H), 7.70 (d, 1H, J=2 Hz), 7.5–7.1 (m, 9H), 5.90 (br, 1H), 4.52 (br, 1H), 3.93 (br, 1H), 2.95 (dd, 1H), 2.88 (dd, 1H).

Anal. Calcd for $C_{19}H_{18}ClN_3O_3+0.5H_2O$: C, 59.92; H, 5.03; N, 11.03. Found: C, 59.66; H, 5.10; N, 11.40.

EXAMPLE 32

5,6-Dichloro-1H-indole-2-carboxylic acid {(1S)-[(R)-hydroxy-(methoxy-methyl-carbamoyl)-methyl]-2-phenyl-ethyl}-amide N,O-Dimethylhydroxylamine hydrochloride (0.24 mmol) and (3S)-[(5,6-dichloro-1H-indole-2-carbonyl)-amino]-(2R)-hydroxy-4-phenyl-butyric acid (0.22 mmol) were coupled according to Procedure A (96 hours reaction time, washed with acid, then base) and the product purified by chromatography on silica eluting with 20–40% ethyl acetate-hexanes: Yield 72%; HPLC (60/40) 7.2 minutes (99%); mp 210–211.5° C.; PBMS 450/452 (MH+, 100%);

¹H NMR (CDCl₃) δ10.41 (br, 1H), 7.73 (s, 1H), 7.68 (s, 1H), 7.4–7.2 (m, 6H), 6.78 (d, 1H, J=ca. 1 Hz), 6.58 (d, 1H, J=10 Hz), 5.03 (m, 1H), 4.34 (d, 1H, J=5 Hz), 3.85 (d, 1H, J=5 Hz), 3.37 (s, 3H), 3.2–3.0 (m, 2H), 3.10 (s, 3H).

Anal. Calcd for $C_{21}H_{21}Cl_2N_3O_4$: C, 56.01; H, 4.70; N, 9.33. Found: C, 55.61; H, 4.68; N, 9.22.

EXAMPLE 33

5-Chloro-1H-indole-2-carboxylic acid [(1S)-((R)-hydroxy-dimethylcarbamoyl-methyl)-2-phenyl-ethyl]-amid Dimethylamine hydrochloride (262 mg, 3.22 mmol) and (3S)-[(5-chloro-1H-indole-2-carbonyl)-amino]-(2R)-hydroxy-4-phenyl-butyric acid (1.0 g, 2.68 mmol) were coupled in DMF (4 mL) using triethylamine (530 mg, 3.22 mmol), 1-hydroxybenzotriazole hydrate (612 mg, 4 mmol), and 1-(3-dimethylaminopropyl)-3-ethylcarbodiimide hydrochloride at 25° C. for 18 hours. The mixture was diluted with chloroform (80 mL) and ethyl acetate (10 mL) and washed with 2N NaOH, 2N HCl, dried and concentrated giving 1.2 g of a colorless foam. This material was dissolved in ethyl acetate and the resulting solution washed twice with 2N NaOH, dried and concentrated giving 1.02 g of a colorless solid. This material was ground up in 10 mL cold ether and filtered, washing with 5 mL cold ether giving after drying a colorless solid: Yield 715 mg, 67%); mp 190–192° C.; HPLC (60/40) 4.53 minutes (100%); FABMS 400/402 (MH+, 80%), 178 (100%);

¹H NMR (CDCl₃) δ9.40 (s, 1H), 7.55 (s, 1H), 7.4–7.1 (m, 7H), 6.86 (d, 1H, J=2 Hz), 6.62 (d, 1H, J=9.6 Hz), 4.65 (m, 1H), 4.40 (m, 2H), 3.10 (m, 2H), 2.88 (s, 3H), 2.72 (s, 3H).

Anal. Calcd for $C_{21}H_{22}ClN_3O_3$: C, 63.08; H, 5.55; N, 10.51. Found: C, 63.03; H, 5.68; N, 10.25.

EXAMPLE 34

5-Chloro-1H-indole-2-carboxylic acid {(1S)-[(R)-hydroxy-(hydroxy-methyl-carbamoyl)-methyl]-2-phenyl-ethyl}-amide N-Methylhydroxylamine hydrochloride (167 mg, 2.0 mmol) and (3S)-[(5-chloro-1H-indole-2-carbonyl)-amino]-(2R)-hydroxy-4-phenyl-butyric acid (373 mg, 1.0 mmol) were coupled according to Procedure A (DMF solvent, base wash omitted) and the crude product purified by chromatography on silica eluting with 0.5–4% ethanol in dichloromethane containing 0.5% acetic acid. The purified product was triturated with ether-hexanes: Yield 13%, HPLC (60/40) 4.26 minutes (97%); mp 182–184.5° C.; TSPMS 402/404 (MH+, 100%);

¹H NMR (DMSO-d₆, partial) δ11.67 (br, 1H), 9.89 (br, 1H), 8.08 (d, 1H, J=10 Hz) 7.71 (d, 1H, J=1.9 Hz), 7.39 (d, 1H, J=8.8 Hz), 7.35–7.1 (m, 7H), 4.73 (m, 2H), 4.51 (m, 1H), 3.05 (s, 3H), 2.93 (m, 2H).

EXAMPLE 35

5-Chloro-1H-indole-2-carboxylic acid [(1S)-((R)-hydroxy-methoxycarbamoyl-methyl)-2-phenyl-ethyl]-amide N-Methoxylamine hydrochloride (0.77 mmol) and (3S)-[(5-chloro-1H-indole-2-carbonyl)-amino]-(2R)-hydroxy-4-phenyl-butyric acid (0.70 mmol) were coupled according to Procedure A (DMF solvent) and the product purified by chromatography on silica eluted with 1–10% ethanol in dichloromethane, followed by trituration with ether-hexanes: Yield 72%; HPLC (60/40) 3.35 minutes (>99%); mp 215–216.5° C. (dec); FABMS 402/404 (MH+, 100%);

Anal. Calcd for $C_{20}H_{20}ClN_3O_4+0.7H_2O$: C, 57.96; H, 5.20; N, 10.14. Found: C, 57.90; H, 5.15; N, 10.10.

EXAMPLE 36

5-Chloro-1H-indole-2-carboxylic acid {(1S)-[(R)-hydroxy-(methoxy-methyl-carbamoyl)-methyl]-2-phenyl-ethyl}-amide N,O-Dimethylhydroxylamine hydrochloride (7.4 mmol) and (3S)-[(5-chloro-1H-indole-2-carbonyl)-amino]-(2R)-hydroxy-4-phenyl-butyric acid (6.7 mmol) were coupled according to Procedure A (dimethylformamide solvent) giving crude product which was chromatographed on silica eluting with 40% then 50% ethyl acetate-hexanes giving crude product which was stirred under 1:1 ether-hexanes overnight, giving a solid which was collected by filtration and dried: Yield 70%; HPLC (60/40) 5.36 minutes (99%); mp 189–190° C.; $^1$H NMR: (CDCl$_3$) δ9.52 (br, 1H), 7.56 (d, 1H, J=2.0 Hz), 7.4–7.3 (m, 5H), 7.38 (m, 1H), 7.18 (dd, 1H, J=2.0, 8.8 Hz), 6.76 (d, 1H, J=1.4 Hz), 6.53 (d, 1H, J=9 Hz), 4.94 (m, 1H), 4.31 (d, 1H, J=5.2 Hz, collapses to s with D$_2$O), 3.86 (d, 1H, J=5.6 Hz, exchanges with D$_2$O), 3.35 (s, 3H), 3.13 (s, 3H), 3.13–2.98 (m, 2H). PBMS 593/595 (MH+, 65%), 200 (100%).

An analysis was obtained on material recrystallized from 1:3 ethyl acetate-hexanes (shrinks at 150° C., mp 189–190° C.): Calcd for: $C_{21}H_{22}ClN_3O_4$: C, 60.65; H, 5.33; N, 10.10. Found: C, 60.52; H, 5.34; N, 10.32.

EXAMPLE 37

5-Chloro-1H-indole-2-carboxylic acid (2S)-[(5-chloro-1H-indole-2-carbonyl)-amino]-(1R)-(methoxy-methyl-carbamoyl)-3-phenyl-propyl ester (3S)-Amino-(2R)-hydroxy-N-methoxy-N-methyl-4-phenyl-butyramide hydrochloride (4.2 mmol) and 5-chloro-1H-indole-2-carboxylic acid (4.2 mmol) were coupled according to Procedure A. The mixture was purified by chromatography on silica eluting with 33–50% ethyl acetate-hexanes giving the title substance (100 mg) and the more polar major substance 5-chloro-1H-indole-2-carboxylic acid {(1S)-[(R)-hydroxy-(methoxy-methyl-carbamoyl)-methyl]-2-phenyl-ethyl}-amide (970 mg), plus a mixture of the two substances (159 mg, mostly more polar product). For the title substance: PBMS 593/595 (MH+, 60%), 400(100%);

$^1$H NMR (CDCl$_3$) δ9.62 (br, 2H), 7.69 (d, 1H, J=2 Hz), 7.56 (d, 1H, J=2 Hz), 7.4–7.2 (m, 10H), 7.04 (d, 1H, J=8.8 Hz), 6.91 (d, 1H, J=1–2Hz), 5.50 (d, 1H, J=2 Hz), 5.09 (m, 1H), 3.47 (s, 3H), 3.26 (dd, 1H, J=6, 13 Hz), 3.14 (s, 3H), 2.99 (dd, 1H, J=10, 13 Hz).

EXAMPLE 38

5-Chloro-1H-indole-2-carboxylic acid ((1S)-benzyl-(2R)-hydroxy-3-oxo-3-pyrrolidin-1-yl-propyl)-amide Pyrrolidine (0.5 mmol) and (3S)-[(5-chloro-1H-indole-2-carbonyl)-amino]-(2R)-hydroxy-4-phenyl-butyric acid (0.5 mmol) were coupled according to Procedure A (dimethylformamide solvent) giving crude product which was triturated with ether: Yield 65%; HPLC (60/40) 6.3 minutes (98%); PBMS 426/428 (MH+, 100%);

Anal. Calcd for $C_{23}H_{24}ClN_3O_3+0.25H_2O$: C, 64.18; H, 5.74; N, 9.76. Found: C, 64.02; H, 5.71; N, 9.61.

EXAMPLE 39

5-Chloro-1H-indole-2-carboxylic acid [(1S)-benzyl-(2R)-hydroxy-3-(3-hydroxy-azetidin-1-yl)-3-oxo-propyl]-amide 3-Hydroxyazetidine hydrochloride (0.56 mmol) and (3S)-[(5-chloro-1H-indole-2-carbonyl)-amino]-(2R)-hydroxy-4-phenyl-butyric acid (0.5 mmol) were coupled according to Procedure A (0–25° C.,1:1 dichloromethane-dimethylformamide solvent) and the crude product purified by chromatography on silica using 2–10% ethanol-dichloromethane: Yield, 69%; HPLC (60/40) 3.38 minutes (96%); PBMS 428/430 (MH+, 100%);

Anal. Calcd for $C_{22}H_{22}ClN_3O_4+0.125H_2O$: C, 61.43; H, 5.21; N, 9.77. Found: C, 61.09; H, 5.57; N, 9.68.

EXAMPLE 40

5-Chloro-1H-indole-2-carboxylic acid ((1S)-benzyl-(2R)-hydroxy-3-isoxazolidin-2-yl-3-oxo-propyl)-amide Isoxazolidine hydrochloride (Cupps, T. L. et al, J. Org. Chem. 1985, 50, 3972–3979, 0.83 mmol) and (3S)-[(5-chloro-1H-indole-2-carbonyl)-amino]-(2R)-hydroxy-4-phenyl-butyric acid (0.79 mmol) were coupled according to Procedure A and the product purified by chromatography on silica gel eluted with 50% and 75% ethyl acetate-hexanes: Yield 75%, HPLC (60/40) 4.94 minutes (95%); TSPMS 428/430 (MH+, 100%);

$^1$H NMR (DMSO-d$_6$) δ11.70 (s, 1H), 8.17 (d, 1H, J=9.3 Hz), 7.71 (s, 1H, J=2 Hz), 7.38 (d, 1H, J=8.7 Hz), 7.27 (m, 4H), 7.15 (m, 3H), 5.02 (d, 1H), 4.61 (m 4.42 (dd, 1H), 4.10 (m, 1H), 3.93 (m, 1H), 3.55 (m, 1H), 2.95 (m 2H), 2.26 (m, 2H).

Anal. Calcd for $C_{22}H_{22}ClN_3O_4$: C, 61.75; H, 5.18; N, 9.82. Found: C, 61.59; H, 5.35; N, 9.44.

EXAMPLE 41

5-Chloro-1H-indole-2-carboxylic acid [(1S)-((R)-diethylcarbamoyl-hydroxy-methyl)-2-phenyl-ethyl]-amide Diethylamine (0.45 mmol) and (3S)-[(5-chloro-1H-indole-2-carbonyl)-amino]-(2R)-hydroxy-4-phenyl-butyric acid (0.4 mmol) were coupled according to Procedure A and the product purified by chromatography on silica eluted with 10–25% ethyl acetate-hexanes: Yield, 35%; HPLC (60/40) 7.06 minutes (96%); mp 218–222° C.; PBMS 428/430 (MH+, 100%);

$^1$H NMR (CDCl$_3$) δ9.14 (s, 1H), 7.61 (s, 1H), 7.4–7.15 (m, 7H), 6.81 (d, 1.3H), 6.55 (d, 1H, J=10 Hz), 4.55 (m, 1H), 4.37 (d, 1H, J=5.2Hz), 4.29 (d, 1H, J=5.3 Hz), 3.43 (m, 1H), 3.2–3.0 (m, 3H), 2.88 (q, 2H, J=7 Hz), 1.05 (t, 3H, J=7.1 Hz), 0.98 (t, 3H, J=7.1 Hz).

EXAMPLE 42

5-Chloro-1H-indole-2-carboxylic acid ((1S)-{(R)-hydroxy-[(2-hydroxy-ethyl)-methyl-carbamoyl]-methyl}-2-phenyl-ethyl)-amide N-(2-Hydroxyethyl)methylamine hydrochloride (0.77 mmol) and (3S)-[(5-chloro-1H-indole-2-carbonyl)-amino]-(2R)-hydroxy-4-phenyl-butyric acid (0.70 mmol) were coupled according to Procedure A (dimethylformamide solvent, acid, then base extraction) and the product purified by chromatography on silica eluted with 0.5–8% ethanol-dichloromethane followed by trituration with ether-hexanes: Yield, 65%; HPLC (60/40) 3.67 minutes (93%); mp 192.5–195° C.; TSPMS 430/432 (MH+, 100%);

1H NMR (CDCl$_3$) δ9.18 (br, 1H), 7.60 (d, 1H, J=2 Hz), 7.4–7.25 (m, 6H), 7.24 (dd, 1H, J=2, 9 Hz), 6.85 (d, 1H, J=2 Hz), 6.63 (d, 1H, J=9 Hz), 4.85 (m, 1H), 4.47 (m, 1H), 4.06 (m, 1H), 3.63 (m, 2H), 3.12 (m, 2H), 2.95 (s, 3H), 2.85 (m, 1H), 2.5 (br, 2H).

Anal. Calcd for $C_{22}H_{24}ClN_3O_4$: C, 61.46; H, 5.63; N, 9.77. Found: C, 61.45; H, 5.95; N, 9.85.

EXAMPLE 43

5-Chloro-1H-indole-2-carboxylic acid ((1S)-benzyl-(2R)-hydroxy-3-oxo-3-piperidin-1-yl-propyl)-amide Piperidine hydrochloride (0.42 mmol) and (3S)-[(5-chloro-1H-indole-2-carbonyl)-amino]-(2R)-hydroxy-4-phenyl-butyric acid (0.4 mmol) were coupled according to Procedure A (1:1 dichloromethane-dimethylformamide solvent) and the product purified by chromatography on silica eluted with 20–25% ethyl acetate-hexanes: Yield 97%; HPLC (60/40) 6.92 minutes (100%); PBMS 440/442 (MH+, 100%);

Anal. Calcd for $C_{24}H_{26}ClN_3O_3$: C, 65.52; H, 5.96; N, 9.55. Found: C, 65.27; H, 6.12; N, 9.29.

EXAMPLE 44

5-Chloro-1H-indole-2-carboxylic acid ((1S)-benzyl-2(R)-hydroxy-3-morpholin-4-yl-3-oxo-propyl)-amide Morpholine (0.55 mmol) and (3S)-[(5-chloro-1H-indole-2-carbonyl)-amino]-(2R)-hydroxy-4-phenyl-butyric acid (0.5 mmol) were coupled according to Procedure A (dimethylformamide solvent) and the product purified by trituration with ether: Yield 50%; HPLC (60/40) 5.37 minutes (>98%); TSPMS 442/444 (MH+, 100%);

$^1$H NMR (CDCl$_3$) δ9.13 (br, 1H), 7.59 (d, 1H, J=2 Hz), 7.35–7.1 (m, 7H), 6.79 (d, 1H, J=2 Hz), 6.51 (d, 1H, J=9 Hz), 4.55 (m, 1H), 4.30 (m, 1H), 4.27 (m, 1H), 3.77 (m, 1H), 3.62 (m, 2H), 3.50 (m, 3H), 3.05 (m, 3H), 2.94 (m, 1H).

Anal. Calcd for $C_{23}H_{24}ClN_3O_4$: C, 62.51; H, 5.47; N, 9.51. Found: C, 62.11; H, 5.39; N, 9.19.

EXAMPLE 45

5-Chloro-1H-indole-2-carboxylic acid ((1S)-benzyl-(2R)-hydroxy-3-[1,2]oxazinan-2-yl-3-oxo-propyl)-amide

[1,2]Oxazinane hydrochloride (0.42 mmol) and (3S)-[(5-chloro-1H-indole-2-carbonyl)-amino]-(2R)-hydroxy-4-phenyl-butyric acid (0.4 mmol) were coupled according to Procedure A (1:1 dichloromethane-dimethylformamide solvent) and the product purified by chromatography on silica eluted with 25% ethyl acetate-hexanes: Yield 76%; HPLC (60/40) 6.07 minutes (99%); PBMS 442/444 (MH+, 100%);

$^1$H NMR (CDCl$_3$) δ9.41 (br, 1H), 7.58 (d, 1H, J=2 Hz), 7.38–7.18 (m, 7H), 6.78 (d, 1H, J=2 Hz), 6.55 (d, 1H, J=9 Hz), 4.89 (m, 1H), 4.58 (s, 1H), 4.00 (m, 1H), 3.67 (m, 3H), 3.10 (m, 2H), 1.9 (br), 1.7 (m, 4H).

Anal. Calcd for $C_{23}H_{24}ClN_3O_4$: C, 62.51; H, 5.47; N, 9.51. Found: C, 62.18; H, 5.59; N, 9.29.

EXAMPLE 46

5-Chloro-1H-indole-2-carboxylic acid [(1S)-benzyl-(2R)-hydroxy-3-((3S)-hydroxy-pyrrolidin-1-yl)-3-oxo-propyl]-amide (R)-3-hydroxypyrrolidine (0.58 mmol) and (3S)-[(5-chloro-1H-indole-2-carbonyl)-amino]-(2R)-hydroxy-4-phenyl-butyric acid (0.56 mmol) were coupled according to Procedure A and the product purified by twice chromatographing on silica eluted with 25–100% ethyl acetate-hexanes: Yield 9%; HPLC (60/40) 3.87 minutes (96%); PBMS 442/444 (MH+, 100%).

EXAMPLE 47

5-Chloro-1H-indole-2-carboxylic acid [(1S)-((R)-tert-butoxycarbamoyl-hydroxy-methyl)-2-phenyl-ethyl]-amide O-Tert-butylhydroxylamine hydrochloride (2.0 mmol) and (3S)-[(5-chloro-1H-indole-2-carbonyl)-amino]-(2R)-hydroxy-4-phenyl-butyric acid (1.0 mmol) were coupled according to Procedure A (dimethylformamide solvent, omit acid washes) and the product purified by chromatography on silica eluted with 30–50% ethyl acetate-hexanes: Yield 77%; HPLC (60/40) 4.96 minutes (98%); FABMS 444 (MH+, 90%), 511 (100%);

$^1$H NMR (CDCl$_3$) δ9.38 (br, 1H), 9.18 (br, 1H), 7.85 (br, 1H), 7.53 (s, 1H), 7.3–7.0 (m, 7H), 6.87 (s, 1H), 4.40 (d, 1H, J=4 Hz), 4.30 (m, 1H), 3.20 (m, 2H), 1.12 (s, 9H).

EXAMPLE 48

5-Chloro-1H-indole-2-carboxylic acid ((1S)-benzyl-(2R)-hydroxy-3-oxo-3-thiazolidin-3-yl-propyl)-amide Thiazolidine (0.70 mmol) and (3S)-[(5-chloro-1H-indole-2-carbonyl)-amino]-(2R)-hydroxy-4-phenyl-butyric acid (0.67 mmol) were coupled according to Procedure A (1:1-dichloromethane-dimethylformamide solvent) giving product which was used without purification: Yield 93%; HPLC (60/40) 5.78 minutes (96%); PBMS 444/446 (MH+, 100%);

Anal. Calcd for $C_{22}H_{22}ClN_3O_3S$: C, 59.52; H, 5.00; N, 9.47. Found: C, 59.29; H, 5.22; N, 9.22.

EXAMPLE 49

5-Bromo-1H-indole-2-carboxylic acid [(1S)-((R)-dimethylcarbamoyl-hydroxy-methyl)-2-phenyl-ethyl]-amide Dimethylamine hydrochloride (0.39 mmol) and (3S)-[(5-bromo-1H-indole-2-carbonyl)-amino]-(2R)-hydroxy-4-phenyl-butyric acid (0.32 mmol) were coupled according to Procedure A (0–25° C.) The crude product (159 mg) was stirred with 200 mg polystyrene-DMAP resin (Aldrich Chemical Co., Milwaukee, Wis.) in dichloromethane for 1 hour at 25° C., filtered and the filtrate concentrated: Yield 68%; HPLC (60/40) 5.4 minutes (>98%); mp 171–176° C.; TSPMS 444/446 (MH+, 85%);

Anal. Calcd for $C_{21}H_{22}N_3O_3Br$: C, 56.77; H, 4.99; N, 9.46. Found: C, 56.42; H, 5.33; N, 9.08.

EXAMPLE 50

5-Chloro-1H-indole-2-carboxylic acid {(1S)-[(R)-hydroxy-(pyridin-3-ylcarbamoyl)-methyl]-2-phenyl-ethyl}-amide 3-Aminopyridine (0.7 mmol) and (3S)-[(5-chloro-1H-indole-2-carbonyl)-amino]-(2R)-hydroxy-4-phenyl-butyric acid (0.70 mmol) were coupled according to Procedure A (dimethylformamide solvent) and the product purified by chromatography on silica eluted with 0.5–8% ethanol in dichloromethane containing 0.5% ammonium hydroxide followed by trituration with ether: Yield 45%; HPLC (60/40) 3.08 minutes (>99%); TSPMS 449/451 (MH+, 100%);

Anal. Calcd for $C_{24}H_{21}ClN_4O_3+0.3H_2O$: C, 63.45; H, 4.79; N, 12.33. Found: C, 63.35; H, 5.03; N, 12.37.

EXAMPLE 51

5-Chloro-1H-indole-2-carboxylic acid {(1S)-[(R)-hydroxy-(2,2,2-trifluoro-ethylcarbamoyl)-methyl]-2-phenyl-ethyl}-amide 2,2,2-Trifluoroethylamine (0.28 mmol) and (3S)-[(5-chloro-1H-indole-2-carbonyl)-amino]-(2R)-hydroxy-4-phenyl-butyric acid (0.28 mmol) were coupled according to Procedure A (dimethylformamide solvent) and the product purified by trituration with ether: mp 228–229.5° C.; Yield 81%; PBMS 454/456 (100%, MH+); 471/473 (MH+NH3, 80%);

Anal. Calcd for $C_{21}H_{19}ClF_3N_3O_3$: C, 55.58; H, 4.22; N, 9.26. Found: C, 55.29; H, 4.25; N, 9.04.

EXAMPLE 52

(S)-5-Chloro-1H-indole-2-carboxylic acid [1-(methoxy-methyl-carbamoanecarbonyl)-2-phenyl-ethyl]-amide 1-(3-Dimethylaminopropyl)-3-ethylcarbodiimide hydrochloride (DEC, 790 mg, 4.12 mmol), dichloroacetic acid (136 mg, 1.06 mmol) and 5-chloro-1H-indole-2-carboxylic acid {(1S)-[(R)-hydroxy-(methoxy-methyl-carbamoyl)-methyl]-2-phenyl-ethyl}-amide (287 mg, 0.69 mmol) were added, in this order, to a solution of anhydrous dimethyl-sulfoxide (4 mL) and toluene (anhydrous, 4 mL) at 0° C. After 18 hours at 25° C., the reaction mixture was diluted with ethyl acetate, and the resulting solution washed with 2N HCl, and saturated aqueous $NaHCO_3$. The organic layer was dried, concentrated and the resulting foam recrystallized from ether. Yield, 100 mg, 35%; HPLC (60/40) 10.72 minutes (87%), starting material eluted at 6.68 minutes in this run and was present at less than 0.5%; PBMS 414/416 (MH+, 70%), 384/386 (100%);

1H NMR ($CDCl_3$ containing 10–20% DMSO-$d_6$) δ9.90 (br, 1H), 7.54 (d, 1H, J=1.7 Hz), 7.3–7.1 (m, ca. 7H), 7.04 (m, 1H), 6.77 (s, 1H), 5.40 (m, 1H), 3.58 (s, 3H), 3.2 (m, 2H), 3.08 (s, 3H).

EXAMPLE 53

5-Chloro-1H-indole-2-carboxylic acid [(1S)-benzyl-(2R)-hydroxy-3-(4-hydroxy-Piperidin-1-yl)-3-oxo-propyl]-amide 4-Hydroxypiperidine hydrochloride (0.51 mmol) and (3S)-[(5-chloro-1H-indole-2-carbonyl)-amino]-(2R)-hydroxy-4-phenyl-butyric acid (0.48 mmol) were coupled according to Procedure A (0–25° C.) and the product purified by trituration with ether, followed by trituration in boiling ethyl acetate, followed by chromatography on silica eluted with 50–100% ethyl acetate-hexanes: Yield 57%; HPLC (60/40) 3.92 minutes (96%); mp 230–232° C.; TSPMS 456/458 MH+, 100%).

$^1$H NMR (DMSO-$d_6$) δ11.65 (br, 0.5H) 11.60 (br, 0.5H), 8.24 (m, 1H), 7.70 (d, 1H, J=2 Hz), 7.38 (d, 0.5H, J=9 Hz), 7.37 (d, 0.5H, J=9 Hz), 7.3–7.1 (m, 7H), 4.8–4.7 (m, 2H), 4.5 (m, 2H), 3.8–3.65 (m, 3H), 3.2 (m, 1H), 3.1 (dd, 1H), 3.0 (dd, 1H), 1.95 (m, 0.5H), 1.7–1.65 (m, 2H), 1.4–1.25 (m, 1.5H).

EXAMPLE 54

5-Chloro-1H-indole-2-carboxylic acid [(1S)-benzyl-(2R)-hydroxy-3-((3R,S)-hydroxy-piperidin-1-yl)-3-oxo-propyl]-amide 3-Hydroxypiperidine (0.56 mmol) and (3S)-[(5-chloro-1H-indole-2-carbonyl)-amino]-(2R)-hydroxy-4-phenyl-butyric acid (0.54 mmol) were coupled according to Procedure A and the product purified by chromatography on silica eluted with 20–40% ethyl acetate-hexanes followed by trituration with 1:1 ether-hexanes: Yield 47%; HPLC (60/40) 4.44 minutes (92%); PBMS 456/458 (MH+, 100%);

Anal. Calcd for $C_{24}H_{26}ClN_3O_4$: C, 63.22; H, 5.75; N, 9.22. Found: C, 62.93; H, 5.90; N, 8.92.

EXAMPLE 55

5-Chloro-1H-indole-2-carboxylic acid [(1S)-benzyl-(2R)-hydroxy-3-((2R)-hydroxymethyl-pyrrolidin-1-yl)-3-oxo-propyl]-amide R-2-pyrrolidinemethanol (1.1 mmol) and (3S)-[(5-chloro-1H-indole-2-carbonyl)-amino]-(2R)-hydroxy-4-phenyl-butyric acid (1.1 mmol) were coupled according to Procedure A and the product purified by chromatography on silica eluted with 1–8% ethanol/dichloromethane followed by chromatography on silica eluted with 50% ethyl acetate-hexanes: Yield 9%; HPLC (60/40) 5.17 minutes (84%); mp 236–239° C.; TSPMS 456/458 (MH+, 100%);

Anal. Calcd for $C_{24}H_{26}ClN_3O_4$: C, 63.22; H, 5.75; N, 9.22. Found: C, 63.23; H, 6.11; N, 8.52.

EXAMPLE 56

5-Chloro-1H-indole-2-carboxylic acid ((1S)-{(R)-[(2-dimethylaminoethyl)-methyl-carbamoyl]-hydroxy-methyl}-2-phenyl-ethyl)-amide N-(2-dimethylaminoethyl)methylamine (0.77 mmol) and (3S)-[(5-chloro-1H-indole-2-carbonyl)-amino]-(2R)-hydroxy-4-phenyl-butyric acid (0.70 mmol) were coupled according to Procedure A (dimethylformamide solvent) and the product purified by chromatography on silica eluted with 1–8% ethanol-dichloromethane containing 0.5% $NH_4OH$, followed by trituration with ether-hexanes: Yield 87%; HPLC (60/40) 2.89 minutes (96%); TSPMS 457/459 (MH+, 100%);

Anal. Calcd for $C_{24}H_{29}ClN_4O_3+0.2H_2O$: C, 62.59; H, 6.43; N, 12.16. Found: C, 62.85; H, 6.82; N, 12.06.

EXAMPLE 57

5-Chloro-1H-indole-2-carboxylic acid [(1S)-benzyl-3-((3R,4R)-dihydroxy-pyrrolidin-1-yl)-2R-hydroxy-3-oxo-propyl]-amide (3R,4R)-3,4-dihydroxypyrrolidine (from 2S,3S-(−)-tartaric acid (unnatural isomer) by the procedure described in U.S. Pat. No. 4,634,775) (1.0 mmol) and (3S)-[(5-chloro-1H-indole-2-carbonyl)-amino]-(2R)-hydroxy-4-phenyl-butyric acid (1.0 mmol) were coupled according to Procedure A (dimethylformamide solvent) and the product purified by chromatography on silica eluted with ethyl acetate followed by trituration with ether: Yield 72%; HPLC (60/40) 3.21 minutes (97%); TSPMS 458/460 (MH+, 100%);

Anal. Calcd for $C_{23}H_{24}ClN_3O_5$: C, 60.33; H, 5.28; N, 9.18. Found: C, 60.09; H, 5.21; N, 9.08.

EXAMPLE 58

5-Chloro-1H-indole-2-carboxylic acid [(1S)-benzyl-3-((3S,4S)-dihydroxy-pyrrolidin-1-yl)-(2R)-hydroxy-3-oxo-propyl]-amide From 2R,3R-(+)tartaric acid, (3S,4S)-Dihydroxypyrrolidine (U.S. Pat. No. 4,634,775 1.0 mmol) and (3S)-[(5-chloro-1H-indole-2-carbonyl)-amino]-(2R)-hydroxy-4-phenyl-butyric acid (1.0 mmol) were coupled according to Procedure A (dimethylformamide solvent) and the product purified by chromatography on silica eluted with ethyl acetate followed by trituration with ether: Yield 60%; HPLC (60/40) 3.02 minutes (98%); TSPMS 458/460 (MH+, 100%);

$^1$H NMR (DMSO-$d_6$) δ11.7 (br, 1H), 8.18 (d, 1H, J=9 Hz), 7.70 (d, 1H, J=2 Hz), 7.38 (d, 1H, J=8.6 Hz), 7.26 (m, 4H), 7.15 (m, 3H), 5.18 (d, 1H, J=4.0 Hz, exchanges), 5.11 (d, 1H), 5.08 (d, 1H), 4.47 (m, 1H), 4.27 (dd, 1H, J=5, 9 Hz, collapses to d in D2O,3.95 (m, 1H), 3.89 (m, 1H), 3.64 (dd, 1H, J=4, 9 Hz), 3.34 (m, 3H), 2.92 (m, 2H).

Anal. Calcd for $C_{23}H_{24}ClN_3O_5+0.5H_2O$: C, 59.16; H, 5.40; N, 9.00. Found: C, 59.44; H, 5.29; N, 8.95.

EXAMPLE 59

5-Chloro-1H-indole-2-carboxylic acid [(1S)-benzyl-3-((3R,4S)-dihydroxy-pyrrolidin-1-yl)-(2R)-hydroxy-3-oxo-propyl]-amide (3R,4S)-Dihydroxypyrrolidine hydrochloride (cis, or meso-isomer 0.86 mmol) and (3S)-[(5-chloro-1H-indole-2-carbonyl)-amino]-(2R)-hydroxy-4-phenyl-butyric acid (0.82 mmol) were coupled according to Procedure A (dimethylformamide solvent) and the product purified by chromatography on silica eluted with 1–10% ethanol in dichloromethane: Yield 39%; HPLC (60/40) 2.92 minutes (96%); PBMS 458/460 (MH+, 100%);

Anal. Calcd for $C_{23}H_{24}ClN_3O_5+0.75H_2O$: C, 58.60; H, 5.45; N, 8.91. Found: C, 59.22; H, 5.52; N, 8.59.

EXAMPLE 59A

Cis-3,4-Dihydroxypyrrolidine hydrochloride (Cis, or meso isomer)

Cis-3,4-dihydroxypyrrolidine-2,5-Dihydro-pyrrole-1-carboxylic acid tert-butyl ester (1.99 g, 9.8 mmol) was dissolved in 4M HCl-dioxane at 5° C. and the resulting suspension stirred at 25° C. for 1 hour. The mixture was concentrated and the residue triturated with ether giving a light purple powder (1.30 g, 95%).

EXAMPLE 59B

Cis-3,4-Dihydroxy-pyrrolidine-1-carboxylic acid tert-butyl ester

A solution of crude 2,5-dihydro-pyrrole-1-carboxylic acid tert-butyl ester was treated sequentially with osmium tetroxide (2.5% in t-butanol, 6 mL) and N-methylmorpholine-N-oxide at 25° C. After 48 hours aqueous 10% sodium thiosulfate solution was added and the mixture was stirred for 30 minutes, partially concentrated to remove tetrahydrofuran, and the resulting aqueous mixture extracted twice with ether. The ether extracts were washed with 10% sodium thiosulfate, 0.1M HCl, dried and concentrated giving a dark orange oil which was chromatographed on silica eluted with 1%, 2%, 4%, 8%, and 10% ethanol-dichloromethane giving an amber syrup (4.09 g).

EXAMPLE 59C 2,5-Dihydro-pyrrole-1-carboxylic acid tert-butyl ester

Di-t-butyldicarbonate (83 g, 380 mmol) was added to a solution of 3-pyrroline (containing 35% pyrrolidine, 25 g, 362 mmol) in tetrahydrofuran (500 mL) at 0° C. The mixture was stirred at 25° C. for 1 hour and concentrated giving 76.2 g of a yellow oil which was used without purification.

EXAMPLE 60

5-Chloro-1H-indole-2-carboxylic acid ((1S)-benzyl-(2R)-hydroxy-3-oxo-3-thiomorpholin-4-yl-propyl)-amide Thiomorpholine (0.52 mmol) and (3S)-[(5-chloro-1H-indole-2-carbonyl)-amino]-(2R)-hydroxy-4-phenyl-butyric acid (0.49 mmol) were coupled according to Procedure A (0–25° C.) and the product purified by chromatography on silica eluted with ethyl acetate-hexanes: Yield 75%; HPLC (60/40) 7.12 minutes (97%); PBMS 458/460 (MH+, 100%).

$^1$H NMR (CDCl$_3$, partial) δ9.15 (br, 1H), 7.60 (d, 1H, J=2 Hz), 7.4–7.2 (m, 7H), 6.80 (d, 1H, J=2 Hz), 6.52 (d, 1H, J=9 Hz), 4.55 (m, 1H), 4.29 (s, 1H), 4.10 (m, 1H), 3.48 (m, 1H), 3.30 (m, 1H), 3.2–2.85 (m, 4H), 2.62 (m, 1H), 2.5 (m, 1H), 2.4 (m, 1H).

EXAMPLE 61

5-Chloro-1H-indole-2-carboxylic acid {(1S)-[(R)-hydroxy-(methyl-pyridin-2-yl-carbamoyl)-methyl]-2-phenyl-ethyl}-amide 2-Methylaminopyridine (3.4 mmol) and (3S)-[(5-chloro-1H-indole-2-carbonyl)-amino]-(2R)-hydroxy-4-phenyl-butyric acid (3.4 mmol) were coupled according to Procedure A (dimethylformamide solvent, 1-hydroxy-7-azabenzotriazole substituted for 1-hydroxybenzotriazole, 18 hour reaction time, no acid wash) and the product purified by chromatography on silica eluted with 0.5–4% ethanol in dichloromethane, followed by four triturations with ether: Yield 5%; HPLC (60/40) 5.57 minutes (95%); TSPMS 463/465 (MH+, 100%);

$^1$H NMR (DMSO-$d_6$) δ11.73 (br, 1H), 8.24 (m, 1H), 8.18 (d, 1H, J=9 Hz), 7.78 (dt, 1H, J=2, 9 Hz), 7.72 (d, 1H, J=2 Hz), 7.43 (s, 1H), 7.41 (s, 1H), 7.28 (m, 1H), 7.25–7.1 (m, 5H), 7.02 (m, 2H), 5.05 (d, 1H, J=9 Hz), 4.60 (m, 1H), 4.35 (m, 1H), 3.22 (s, 3H), 2.70 (m, 2H).

Anal. Calcd for $C_{25}H_{23}ClN_4O_3+1.3H_2O$: C, 61.74; H, 5.31; N, 11.52. Found: C, 61.84; H, 5.00; N, 11.52.

EXAMPLE 62

5-Chloro-1H-indole-2-carboxylic acid [(1S)-benzyl-3-(4-formylpiperazin-1-yl)-(2R)-hydroxy-3-oxo-propyl]-amide 1-Formylpiperazine (0.77 mmol) and (3S)-[(5-chloro-1H-indole-2-carbonyl)-amino]-(2R)-hydroxy-4-phenyl-butyric acid (0.70 mmol) were coupled according to Procedure A (dimethylformamide solvent, acid then base washes) and the product purified by chromatography on silica eluted with 0.5–8% ethanol-dichloromethane, followed by trituration with ether-hexanes: Yield 78%; HPLC (60/40) 3.45 minutes (96%); PBMS 469/471 (MH+,100%);

Anal. Calcd for $C_{24}H_{25}ClN_4O_4+0.3H_2O$: C, 60.77; H, 5.44; N, 11.81. Found: C, 60.65; H, 5.70; N, 11.85.

EXAMPLE 63

5-Chloro-1H-indole-2-carboxylic acid [(1S)-benzyl-(2R)-hydroxy-3-(4-hydroxymethyl-piperidin-1-yl)-3-oxo-propyl]-amide 4-(Hydroxymethyl)piperidine (1.5 mmol) (J. Med. Chem 1991, 34, 1073) and (3S)-[(5-chloro-1H-indole-2-carbonyl)-amino]-(2R)-hydroxy-4-phenyl-butyric acid (1.4 mmol) were coupled according to Procedure A and the product purified by chromatography on silica eluted with 50–100% ethyl acetate-hexanes: Yield 70%; HPLC (60/40) 4.09 minutes (97%); TSPMS 470/472 (MH+, 100%);

Anal. Calcd for $C_{25}H_{28}ClN_3O_4+0.25H_2O$: C, 63.29; H, 6.05; N, 8.86. Found: C, 63.39; H, 6.00; N, 8.63.

EXAMPLE 64

5-Chloro-1H-indole-2-carboxylic acid ((1S)-{(R)-hydroxy-[methyl-(2-pyridin-2-yl-ethyl)-carbamoyl]-methyl}-2-phenyl-ethyl)-amide Methyl-(2-pyridin-2-yl-ethyl)-amine (0.77 mmol) and (3S)-[(5-chloro-1H-indole-2-carbonyl)-amino]-(2R)-hydroxy-4-phenyl-butyric acid (0.70 mmol) were coupled according to Procedure A (dimethylformamide solvent) and the product purified by chromatography on silica eluted with 0.5–8% ethanol-dichloromethane: Yield 82%; HPLC (60/40) 3.33 minutes (97%); TSPMS 491/493 (MH+,100);

$^1$H NMR (CDCl$_3$) δ9.84 (br, 0.7H), 9.35 (br, 0.3H), 8.49 (m, 1H), 7.7–7.5 (m, 2H), 7.4–7.1 (m, 9H), 6.92 (d, 0.3H, J=8 Hz), 6.8 (m, 1.4H), 6.65 (d, 0.3H, J=9 Hz), 4.62 (m, 1.5H), 4.5 (m, 0.5H), 4.34 (s, 0.7H), 4.29 (s, 0.3H), 3.82 (m, 1H), 3.48 (m, 2H), 3.05 (m, 3H), 2.86 (s, 1H), 2.70 (s, 2H).

Anal. Calcd for $C_{27}H_{27}ClN_4O_3+0.2H_2O$: C, 65.57; H, 5.58; N, 11.33. Found: C, 65.56; H, 5.84; N, 11.36.

EXAMPLE 65

1-{(3S)-[(5-Chloro-1H-indole-2-carbonyl)-amino]-(2R)-hydroxy-4-phenyl-butyryl}-piperidine-4-carboxylic acid ethyl ester Ethyl isonipecotate and (3S)-[(5-chloro-1H-indole-2-carbonyl)-amino]-(2R)-hydroxy-4-phenyl-butyric acid (0.75 mmol) were coupled according to Procedure A and the product purified by chromatography on silica eluted with 20–40% ethyl acetate-hexanes: Yield 95%; HPLC (60/40) 7.96 minutes (95%); PBMS 512/514 (MH+, 100%).

EXAMPLE 66

1-{(3S)-[(5-Chloro-1H-indole-2-carbonyl)-amino]-(2R)-hydroxy-4-phenyl-butyryl}-pyrrolidine-2(S)-carboxylic acid tert-butyl ester (S)-pyrrolidine-2-carboxylic acid tert-butyl ester and (3S)-[(5-chloro-1H-indole-2-carbonyl)-amino]-(2R)-hydroxy-4-phenyl-butyric acid (2.1 mmol) were coupled according to Procedure A (60 hour reaction time) and the product purified by chromatography on silica eluted with 25–50% ethyl acetate-hexanes: Yield 74%; HPLC (60/40) 8.27 minutes (99%); TSPMS 526/528 (MH+, 100%);

Anal. Calcd for $C_{28}H_{32}ClN_3O_5$: C, 63.93; H, 6.13; N, 7.99. Found: C, 64.05; H, 6.32; N, 7.79.

EXAMPLE 67

5-Chloro-1H-indole-2-carboxylic acid {(1R)-[(S)-hydroxy-(methoxy-methyl-carbamoyl)-methyl]-2-phenyl-ethyl}-amide 5-Chloro-1H-indole-2-carboxylic acid (0.25 mmol) and (2S,3R)-3-amino-2-hydroxy-N-methoxy-N-methyl-4-phenyl-butyramide hydrochloride (0.25 mmol) were coupled according to Procedure A (0–25° C. acid then base wash). The crude product was dissolved in methanol containing 0.25 equivalent 1N NaOH for 2 hours at 25° C. and another hour with a second 0.25 equivalent portion of 1N NaOH (to hydrolyze the less polar N,O-bis-5-chloro-1H-indolecarbonyl derivative), the solution concentrated, the residue dissolved in ethyl acetate, the resulting solution washed with 2N HCl, brine, dried, and concentrated. The residue was purified by chromatography on silica eluted with 30–50% ethyl acetate-hexane. The chromatographed material (containing a polar impurity) was dissolved in ethyl acetate and the resulting solution washed twice with 2N NaOH, dried, and concentrated: Yield 57%; HPLC (60/40) 5.36 minutes (98%); mp 165–167° C.; PBMS 416/418 (MH+,100%);

$^1$H NMR (CDCl$_3$) δ9.45 (br, 1H), 7.58 (d, 1H, J=2 Hz), 7.4–7.1 (m, 7H), 6.77 (d, 1H, J=2 Hz), 6.51 (d, 1H, J=10 Hz), 4.91 (m, 1H), 4.30 (d, 1H, J=5 Hz), 3.83 (d, 1H, J=5 Hz), 3.35 (s, 3H), 3.13 (s, 3H), 3.09 (m, 2H).

Anal. Calcd for $C_{21}H_{22}ClN_3O_4+1.0H_2O$: C, 58.13; H, 5.58; N, 9.68; Found: C, 58.05; H, 5.24; N, 9.54.

EXAMPLE 67A (2S,3R)-3-amino-2-hydroxy-N-methoxy-N-methyl-4-phenyl-butyramide hydrochloride {1(R)-[Hydroxy-((S)-methoxy-methyl-carbamoyl)-methyl]-2-phenyl-ethyl}-carbamic acid (285 mg, 0.8 mmol) was dissolved in cold 4N HCl-dioxane and the resulting solution stirred for 1 hour at 0° C. The mixture was concentrated and the residue triturated with ether and dried giving 207 mg (90%) of a solid.

EXAMPLE 67B

{(1S)-[Hydroxy-((R)-methoxy-methyl-carbamoyl)-methyl]-2-phenyl-ethyl}-carbamic acid (2S,3R)-3-(t-Butoxycarbonylamino)-2-hydroxy-4-phenylbutyric acid (300 mg, 1.0 mmol, Sigma Chemical Co., St. Louis, Mo.)) and N,O-dimethylhydroxylamine hydrochloride (104 mg, 1.1 mmol) were coupled according to Procedure A (0–25° C. reaction temperature): Yield 88%; HPLC (60/40) 4.90 minutes (95%);

EXAMPLE 68

5-Chloro-1H-indole-2-carboxylic acid {(1 R)-[hydroxy-((R)-methoxy-methyl-carbamoyl)-methyl]-2-phenyl-ethyl}-amide N,O-Dimethylhydroxylamine dihydrochloride (0.32 mmol) and (3R)-[(5-Chloro-1H-indole-2-carbonyl)-amino]-

(2R)-hydroxy-4-phenyl-butyric acid (0.3 mmol) were coupled according to Procedure A (0–25° C., acid then base washing) and the product purified by chromatography on silica eluted with 20–50% ethyl acetate-hexanes: Yield 73%; HPLC (60/40) 4.86 minutes (95%); PBMS 416/418 (MH+, 100%);

$^1$H NMR (CDCl$_3$) δ9.47 (br, 1H), 7.58 (d, 1H, J=1.7 Hz), 7.31 (d, 1H, J=8.7 Hz), 7.30–7.10 (m, 6H), 6.78 (d, 1H, J=10 Hz), 6.74 (s, 1H), 5.00 (m, 1H), 4.63 (m, 1H), 3.80 (br, ca. 1H), 3.70 (s, 3H), 3.04 (s, 3H), 2.87 (m, 2H).

Anal. Calcd for $C_{21}H_{22}ClN_3O_4$+0.1H$_2$O: C, 60.39; H, 5.36; N, 10.06. Found: C, 60.76; H, 5.74; N, 9.78.

EXAMPLE 69

5-Chloro-1H-indole-2-carboxylic acid [(1S)-benzyl-(2R)-hydroxy-3-oxo-3-(1-oxo-1-thiazolidin-3-yl)-propyl]-amide m-Chloroperoxybenzoic acid (62 mg of 50%, 0.18 mmol) was added at 25° C. to a solution of 5-chloro-1H-indole-2-carboxylic acid ((1S)-benzyl-(2R)-hydroxy-3-oxo-3-thiazolidin-3-yl-propyl)-amide (80 mg, 0.18 mmol) in dichloromethane (2 mL). After 1 hour the mixture was poured into a mixture of saturated aqueous sodium bicarbonate (12 mL) and 10% aqueous sodium thiosulfate (12 mL) and ethyl acetate. The aqueous layer was separated and extracted twice with ethyl acetate. The organic layers were combined, washed with saturated aqueous sodium bicarbonate, dried, and concentrated giving a yellow solid (80 mg, 96%): HPLC (60/40) 3.37 (97%); PBMS 460/462 (MH+, 100%).

EXAMPLE 70 AND 71

5-Chloro-1H-indole-2-carboxylic acid [(1S)-benzyl-(2R)-hydroxy-3-oxo-3-(1-oxo-1-thiomorpholin-4-yl)-propyl]-amide (Example 70)

AND

5-Chloro-1H-indole-2-carboxylic acid [(1S)-benzyl-3-(1,1-dioxo-1-thiomorpholin-4-yl)-(2R)-hydroxy-3-oxo-propyl]-amide (Example 71)

m-Chloroperoxybenzoic acid (45 mg of 50%, 0.13 mmol) was added at 25° C. to a solution of 5-chloro-1H-indole-2-carboxylic acid ((1S)-benzyl-(2R)-hydroxy-3-oxo-3-thiomorpholin-4-yl-propyl)-amide (60 mg, 0.13 mmol) in dichloromethane (1.5 mL). After 1 hour the mixture was poured into a mixture of saturated aqueous sodium bicarbonate (12 mL) and 10% aqueous sodium thiosulfate (12 mL) and ethyl acetate. The aqueous layer was separated and extracted twice with ethyl acetate. The organic layers were combined, washed with saturated aqueous sodium bicarbonate, dried, and concentrated giving the title sulfoxide (Example 70) as a yellow solid which was chromatographed on silica gel eluting with 1% ethanol-dichloromethane: Yield 44 mg, 72%; HPLC (60/40) 6.14 minutes (98%). PBMS 474/476 (MH+, 100%). A less polar product (8 mg) identified as the title sulfone (Example 71) was also isolated: HPLC (60/40) 6.44 minutes (96%). PBMS 490/492 (MH+, 100%).

EXAMPLE 72

1-{(3S)-[(5-Chloro-1H-indole-2-carbonyl)-amino]-(2R)-hydroxy-4-phenyl-butyryl}-piperidine-4-carboxylic acid Lithium hydroxide solution (0.2 mL of 1N in water) was added to a solution of 1-{(3S)-[(5-Chloro-1H-indole-2-carbonyl)-amino]-(2R)-hydroxy-4-phenyl-butyryl}-piperidine-4-carboxylic acid ethyl ester (111 mg, 0.22 mmol) in tetrahydrofuran (2 mL) at 25° C. After 18 hours the mixture was concentrated and the residue triturated with ether. The resulting solid was partitioned between water and ethyl acetate and 6N HCl was added to attain a pH of 1. The organic layer was separated, dried and concentrated giving 109 mg (100%) of a solid: HPLC (60/40) 3.79 minutes (99%);

TSPMS 484/486 (MH+, 100%);

$^1$H NMR (DMSO-d$_6$) δ12.25 (br, 1H), 11.65 (br, 1H), 8.17 (d, 0.5H, J=9 Hz), 8.14 (d, 0.5H, J=9 Hz), 7.70 (d, 1H, J=2 Hz), 7.38 (d, 1H, J=8.8 Hz), 7.35–7.1 (m, 7H), 4.78 (m, 1H, exchanges with D$_2$O), 4.5 (m, 2H), 4.1 (m, 1H), 3.8 (m, 0.5H), 3.7 (m, 0.5H), 3.15 (m, 0.5H), 3.0 (m, 2–2.5H), 2.75 (m, 1H), 1.5 (possible m, 1H), 1.8 (m, 2–2.5H), 1.5 (m, ca. 1.5H).

Anal. Calcd for $C_{25}H_{26}ClN_3O_5$+0.55H$_2$O: C, 60.80; H, 5.53; N, 8.51. Found: C, 61.15; H, 5.68; N, 8.11.

EXAMPLE 73

5-Chloro-1H-indole-2-carboxylic acid [(1S)-((R)-hydroxy-hydroxycarbamoyl-methyl)-2-phenyl-ethyl]-amide Trifluoroacetic acid (2 mL) was added to a solution of 5-chloro-1H-indole-2-carboxylic acid [(1S)-((R)-tert-butoxycarbamoyl-hydroxy-methyl)-2-phenyl-ethyl]-amide (256 mg, 0.58 mmol) in dichloromethane (2 mL) and the resulting solution was stirred for 18 hours at 25° C. More trifluoroacetic acid (2 mL) was added and the mixture was allowed to stand for 72 hours, concentrated, and the residue chromatographed on silica gel eluting with 2.5%, 5%, 10% ethanol-dichloromethane containing 1% acetic acid. The purified product was triturated with ether-hexanes and dried: Yield 70 mg, 31%; HPLC (60/40) 3.11 (96%);

Anal. Calcd for $C_{19}H_{18}ClN_3O_4$+1.0H$_2$O: C, 56.23; H, 4.97; N, 10.35. Found: C, 56.63; H, 4.94; N, 9.95.

EXAMPLE 74

5-Chloro-1H-indole-2-carboxylic acid ((1S)-{[(benzyl-piperidin-4-yl)-methyl-carbamoyl]-(R)-hydroxy-methyl}-2-phenyl-ethyl)-amide (3S)-[(5-Chloro-1H-indole-2-carbonyl)amino]-(2R)-hydroxy-4-phenylbutyric acid (310 mg, 0.8 mmol) and (1-benzyl-piperidin4-yl)-methyl-amine hydrochloride (EPO publication 0 457 686, example 1A therein, 200 mg, 0.8 mmol) were coupled according to Procedure A (dimethylformamide solvent). The crude product was purified by chromatography on silica gel eluted with 0.5–4% ethanol in dichloromethane containing 0.5% ammonium hydroxide giving a colorless foam: yield 140 mg, 30%; HPLC (60/40) 4.15 minutes (95%); TSPMS 559/562 (MH+, 100%);

Anal. Calcd for $C_{32}H_{35}ClN_4O_3$+HCL+1.5H$_2$O: C, 61.73; H, 6.31; N, 9.00. Found: C, 61.61; H, 6.29; N, 8.71.

EXAMPLE 75

4-({(3S)-[(5-Chloro-1H-indole-2-carbonyl)-amino]-(2R)-hydroxy-4-phenyl-butyryl}-methyl-amino)-piperidine-1-carboxylic acid tert-butyl ester (3S)-[(5-Chloro-1H-indole-2-carbonyl)-amino]-(2R)-hydroxy-4-phenyl-butyric acid (1.0 g, 2.6 mmol) and 4-methylamino-piperidine-1-carboxylic acid tert-butyl ester (575 mg, 2.6 mmol) were coupled according to Procedure A (dimethylformamide solvent). The crude product was purified by chromatography on silica gel eluted with 20, 30, 40, 50, and 75% ethyl acetate-hexanes: yield 319 mg, 21%; HPLC (60/40) 10.31 minutes (94%); 569/571 (MH+, 100%).

EXAMPLE 75A

4-Methylamino-piperidine-1-carboxylic acid tert-butyl ester

Powdered molecular seives (3 Å, 5.2 g), methylamine hydrochloride (16.96 g, 251 mmol), anhydrous sodium acetate (41.21 g, 502 mmol), and 95% sodium cyanoborohydride (3.99 g, 60 mmol) were added sequentially to a solution of 4-oxo-piperidine-1-carboxylic acid tert-butyl ester in methanol (400 mL) at 0° C., and the mixture was allowed to warm to 25° C. over several hours. After 18 hours at 25°C., the reaction mixture was filtered thru Celite®, the solids washed with methanol and ethyl acetate, and the filtrate concentrated. The residue was dissolved in ethyl acetate and the resulting solution washed twice with 2N NaOH, once with brine, dried and concentrated to an oil (12.79 g, 119%).

EXAMPLE 76

5-Chloro-1H-indole-2-carboxylic acid {(1-S)[(R)-hydroxy-(methyl-piperidin-4-yl-carbamoyl)-methyl]-2-phenyl-ethyl}-amide hydrochloride 4-({(3S)-[(5-Chloro-1H-indole-2-carbonyl)-amino]-(2R)-hydroxy-4-phenyl-butyryl}-methyl-amino)-piperidine-1-carboxylic acid tert-butyl ester (292 mg, 0.5 mmol) was dissolved in 4M HCl-dioxane at 0° C. and stirred for 1 hour at room temperature. The mixture was concentrated and the residue triturated with ether and dried: yield 249 mg, 96%; HPLC (60/40) 2.59 minutes (96%). PBMS 469/471 (MH+, 100%);

$^1$H NMR (DMSO-$d_6$) δ11.7 (s, 0.3H), 11.6 (s, 0.7H), 8.75 (br, 2H, exchanges with $D_2O$), 7.70 (d, 1H, J=2 Hz), 7.4–7.1 (m, 8H), 4.94 (d, 0.3H, J=7.8 Hz, exchanges with $D_2O$), 4.77 (d, 0.7H, J=7.7 Hz, exchanges with $D_2O$), 4.6 (m, 1H), 4.47 (dd, 1H, J=3, 8Hz), 4.4 (m, 0.7H), 3.9 (m, 0.3H), 3.4–3.2 (m, ca. 1.5H), 2.95 (m, 2H), 2.15–1.8 (m, ca. 2.5H), 1.75–1.50 (m, 2H).

Anal. Calcd for $C_{25}H_{29}ClN_4O_3$+HCl+0.7$H_2O$: C, 57.96; H, 6.11; N, 10.82. Found: C, 58.22; H, 6.23; N, 10.46.

EXAMPLE 77

5-Chloro-1H-indole-2-carboxylic acid ((1S)-{(R)-hydroxy-[methyl-(1-methyl-piperidin-4-yl)-carbamoyl]-methyl}-2-phenyl-ethyl)-amide hydrochloride Molecular seives (3 Å powdered, 100 mg), triethylamine (22 mg, 0.2 mmol), glacial acetic acid (64 mg, 1.1 mmol), sodium cyanoborohydride (95%,18 mg, 0.3 mmol), and aqueous formaldehyde (37 weight % in water, 22 mg, 0.3 mmol) were added sequentially to a solution of 5-chloro-1H-indole-2-carboxylic acid {(1S)-[(R)-hydroxy-(methyl-piperidin4-yl-carbamoyl)-methyl]-2-phenyl-ethyl}-amide hydrochloride (100 mg, 0.2 mmol) in methanol (2 mL) at 25° C. After 18 hours the reaction mixture was filtered thru Celite®, the solids washed with methanol and concentrated. The residue was dissolved in ethyl acetate and the resulting solution washed twice with 2N NaOH, brine, dried and concentrated. The colorless solid residue was purified by chromatography on silica gel eluted with 1–8% ethanol in dichloromethane giving a colorless solid (93 mg, 91%). This material was dissolved in methanol at 0° C., the resulting solution treated with 1.01 N HCl (0.21 mL), and the resulting solution immediately concentrated. The residue was triturated with ether and dried: yield 87 mg, 79%; HPLC (60/40) 2.86 minutes (95%); TSPMS 483/485 (MH+, 100%);

EXAMPLE 78

(3S)-[(5-Chloro-1H-indole-2-carbonyl)-amino]-4-phenyl-butyric acid methyl ester (3S)-3-Amino4-phenyl-butyric acid methyl ester hydrochloride (1.15 g, 5 mmol) and 5-chloro-1H-indole-2-carboxylic acid were coupled according to procedure A. The product was purified by trituration with ether: yield 1.46 g (79%); HPLC (60/40) 8.85 minutes (100%); PBMS 371/373 (MH+, 100/35%);

Anal. Calcd for $C_{20}H_{19}ClN_2O_3$: C, 64.78; H, 5.16; N, 7.55. Found: C, 64.81; H, 5.34; N, 7.46.

EXAMPLE 78A (3S)-Amino4-phenyl-butyric acid methyl ester hydrochloride (3S)-tert-Butoxycarbonylamino-4-phenyl-butyric acid methyl ester (ref. Heterocycles, p. 1835 (1989) and J. Med. Chem. 1975, p. 761, 3.49 g, 12.1 mmol) was dissolved in 4M HCl-dioxane at 0° C. and stirred for 0.5 hours at 225° C. The mixture was concentrated and the residue triturated with ether and dried: Yield 2.56 g (92%).

It should be understood that the invention is not limited to the particular embodiments described herein, but that various changes and modifications may be made without departing from the spirit and scope of this novel concept as defined by the following claims.

What is claimed is:
1. A compound of Formula I

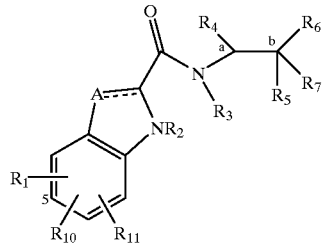

Formula I and the pharmaceutically acceptable salts and prodrugs thereof wherein the dotted line (---) is an optional bond;

A is —C(H)=, —C(($C_1$–$C_4$)alkyl)= or —C(halo)= when the dotted line (---) is a bond, or A is methylene or —CH(($C_1$–$C_4$)alkyl)— when the dotted line (---) is not a bond;

$R_1$, $R_{10}$ or $R_{11}$ are each independently H, halo, 4-, 6- or 7-nitro, cyano, ($C_1$–$C_4$)alkyl, ($C_1$–$C_4$)alkoxy, fluoromethyl, difluoromethyl or trifluoromethyl;

$R_2$ is H;

$R_3$ is H or ($C_1$–$C_5$)alkyl;

$R_4$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, phenyl($C_1$–$C_4$)alkoxy($C_1$–$C_4$)alkyl, thien-2- or -3-yl($C_1$–$C_4$)alkyl or fur-2- or -3-yl($C_1$–$C_4$)alkyl wherein said $R_4$ rings are mono-,di- or tri-substituted independently on carbon with H, halo, ($C_1$–$C_4$)alkyl, ($C_1$–$C_4$)alkoxy, trifluoromethyl, hydroxy, amino or cyano;

$R_5$ is hydroxy, fluoro, ($C_1$–$C_5$)alkoxy, ($C_1$–$C_6$)alkanoyl, amino($C_1$–$C_4$)alkoxy, mono-N- or di-N, N-($C_1$–$C_4$) alkylamino($C_1$–$C_4$)alkoxy, carboxy($C_1$–$C_4$)alkoxy, ($C_1$–$C_5$)alkoxy-carbonyl($C_1$–$C_4$)alkoxy, benzyloxycarbonyl($C_1$–$C_4$)alkoxy, or carbonyloxy wherein said carbonyloxy is carbon-carbon linked with phenyl or furyl and wherein said preceding $R_5$ rings are optionally mono-substituted with halo, ($C_1$–$C_4$)alkyl, ($C_1$–$C_4$)alkoxy, hydroxy, amino or trifluoromethyl and said mono-substituents are bonded to carbon;

$R_7$ is H, fluoro or ($C_1$–$C_5$)alkyl; or $R_5$ and $R_7$ can be taken together to be oxo;

$R_6$ is carboxy, ($C_1$–$C_8$)alkoxycarbonyl, $C(O)NR_8R_9$ or $C(O)R_{12}$, wherein $R_8$ is H, ($C_1$–$C_3$)alkyl, hydroxy or ($C_1$–$C_3$)alkoxy; and $R_9$ is H, ($C_1$–$C_8$)alkyl, hydroxy, ($C_1$–$C_8$)alkoxy, methyleneperfluorinated($C_1$–$C_8$)alkyl, phenyl, thienyl, furyl or pyrrolidinyl wherein said preceding $R_9$ rings are carbon-nitrogen linked; or $R_9$ is mono-, di- or tri-substituted ($C_1$–$C_5$)alkyl, wherein said substituents are independently H, hydroxy, amino, mono-N- or di-N,N-($C_1$–$C_5$)alkylamino; or $R_9$ is mono- or di-substituted ($C_1$–$C_5$)alkyl, wherein said substituents are independently phenyl, furyl or pyrrolidinyl wherein the nonaromatic nitrogen-containing $R_9$ rings are optionally mono-substituted on nitrogen with ($C_1$–$C_6$) alkyl, benzyl, benzoyl or ($C_1$–$C_6$)alkoxycarbonyl and wherein the $R_9$ rings are optionally mono-substituted on carbon with halo, ($C_1$–$C_4$)alkyl, ($C_1$–$C_4$)alkoxy, hydroxy, amino, or mono-N- and di-N,N ($C_1$–$C_5$) alkylamino provided that no quaternized nitrogen is included and there are no nitrogen-oxygen, nitrogen-nitrogen or nitrogen-halo bonds;

$R_{12}$ is 2-($C_1$–$C_6$)alkoxycarbonylpyrrolidin-1-yl or 2(R)-hydroxymethylpyrrolidin-1-yl; or $R_{12}$ is 3- and/or 4-, mono- or di-substituted pyrrolidin-1-yl wherein said $R_{12}$ substituents are independently H, halo, ($C_1$–$C_5$)-alkyl, hydroxy, amino, mono-N- or di-N,N-($C_1$–$C_5$)alkylamino, formyl, oxo, hydroxyimino, ($C_1$–$C_5$)alkoxy, carboxy, carbamoyl, mono-N-or di-N, N-($C_1$–$C_4$)alkylcarbamoyl, ($C_1$–$C_4$)alkoxyimino, ($C_1$–$C_4$)alkoxymethoxy, ($C_1$–$C_6$)alkoxycarbonyl, carboxy($C_1$–$C_5$)alkyl or hydroxy($C_1$–$C_5$)alkyl;

with the proviso that if $R_4$ is H, methyl, ethyl or n-propyl, $R_5$ is OH; with the proviso that if $R_5$ and $R_7$ are H, then $R_4$ is not H, methyl, ethyl, n-propyl, hydroxy($C_1$–$C_3$) alkyl or ($C_1$–$C_3$)alkoxy($C_1$–$C_3$)alkyl and $R_6$ is C(O) $NR_8R_9$, $C(O)R_{12}$ or ($C_1$–$C_4$)alkoxycarbonyl.

2. A compound as recited in claim 1 wherein $R_1$ is 5-H, 5-halo, 5-methyl, 5-trifluoromethyl or 5-cyano;

$R_{10}$ and $R_{11}$ are each independently H or halo;

A is —C(H)=;

$R_2$ and $R_3$ are H;

$R_4$ is phenyl($C_1$–$C_2$)alkyl wherein said phenyl groups are mono-, di- or tri-substituted independently with H or halo or mono- or di-substituted independently with H, halo, ($C_1$–$C_4$)alkyl, ($C_1$–$C_4$)alkoxy, trifluoromethyl, hydroxy, amino or cyano; or $R_4$ is thien-2- or -3-yl ($C_1$–$C_2$)alkyl or fur-2- or -3-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is hydroxy;

$R_6$ is $C(O)NR_8R_9$ or $C(O)R_{12}$; and $R_7$ is H.

3. A compound as recited in claim 2 wherein the carbon atom a has (S) stereochemistry;

the carbon atom b has (R) stereochemistry;

$R_4$ is phenyl($C_1$–$C_2$)alkyl, thien-2-yl-($C_1$–$C_2$)alkyl, thien-3-yl-($C_1$–$C_2$)alkyl, fur-2-yl-($C_1$–$C_2$)alkyl or fur-3-yl-($C_1$–$C_2$)alkyl wherein said rings are mono- or di-substituted independently with H or fluoro;

$R_6$ is $C(O)NR_8R_9$;

$R_8$ is ($C_1$–$C_3$)alkyl, hydroxy or ($C_1$–$C_3$)alkoxy; and $R_9$ is H, ($C_1$–$C_8$)alkyl, hydroxy, hydroxy($C_1$–$C_6$)alkyl, ($C_1$–$C_8$)alkoxy, pyrrolidinyl or ($C_1$–$C_4$)alkyl mono-substituted with pyrrolidinyl.

4. A compound as recited in claim 3 selected from

5-Chloro-1H-indole-2-carboxylic acid [(1S)-((R)-hydroxy-dimethylcarbamoyl-methyl)-2-phenyl-ethyl]-amide, 5,6-Dichloro-1H-indole-2-carboxylic acid {(1S)-[(R)-hydroxy-(methoxy-methyl-carbamoyl)-methyl]-2-phenyl-ethyl}-amide, 5-Chloro- 1H-indole-2-carboxylic acid {(1S)-[(R)-hydroxy-(methoxy-methyl-carbamoyl)-methyl]-2-phenyl-ethyl}-amide or 5-Chloro-1H-indole-2-carboxylic acid ((1S)-{(R)-hydroxy-[(2-hydroxy-ethyl)-methyl-carbamoyl]-methyl}-2-phenyl-ethyl)-amide.

5. The compound as recited in claim 3 wherein $R_1$ is 5-chloro;

$R_{10}$ and $R_{11}$ are H;

$R_4$ is benzyl;

$R_8$ is methyl; and $R_9$ is methyl.

6. The compound as recited in claim 3 wherein $R_1$ is 5-chloro;

$R_{11}$ is H;

$R_{10}$ is 6-chloro;

$R_4$ is benzyl;

$R_8$ is methyl; and $R_9$ is methoxy.

7. The compound as recited in claim 3 wherein $R_1$ is 5-chloro;

$R_{10}$ and $R_{11}$ are H;

$R_4$ is benzyl;

$R_8$ is methyl; and $R_9$ is methoxy.

8. The compound as recited in claim 3 wherein $R_1$ is 5-chloro;

$R_{10}$ and $R_1$ are H;

$R_4$ is benzyl;

$R_8$ is methyl; and $R_9$ is 2-(hydroxy)ethyl.

9. A compound as recited in claim 2 wherein
the carbon atom a is (S) stereochemistry;
the carbon atom b is (R) stereochemistry;
$R_4$ is phenyl($C_1$–$C_2$)alkyl, thien-2-yl-($C_1$–$C_2$)alkyl, thien-3-yl-($C_1$–$C_2$)alkyl, fur-2-yl-($C_1$–$C_2$)alkyl or fur-3-yl-($C_1$–$C_2$)alkyl wherein said rings are mono- or di-substituted independently with H or fluoro;
$R_6$ is C(O)$R_{12}$; and
$R_{12}$ is 3- and/or 4-, mono- or di-substituted pyrrolidin-1-yl wherein said substituents are each independently H, halo, hydroxy, amino, mono-N- or di-N,N—($C_1$–$C_6$)alkylamino, oxo, hydroxyimino or alkoxy.

10. A compound as recited in claim 1 selected from

5-Chloro-1H-indole-2-carboxylic acid [(1S)-benzyl-(2R)-hydroxy-3-((3S)-hydroxy-pyrrolidin-1-yl)-3-oxo-propyl]-amide,
5-Chloro-1H-indole-2-carboxylic acid [(1S)-benzyl-3-((3S,4S)-dihydroxy-pyrrolidin-1-yl)-(2R)-hydroxy-3-oxo-propyl]-amide or
5-Chloro-1H-indole-2-carboxylic acid [(1S)-benzyl-3-((3R,4S)-dihydroxy-pyrrolidin-1-yl)-(2R)-hydroxy-3-oxo-propyl]-amide.

11. The compound as recited in claim 9 wherein
$R_1$ is 5-chloro;
$R_{10}$ and $R_{11}$ are H;
$R_4$ is benzyl; and
$R_{12}$ is 3(S)-hydroxypyrrolidin-1-yl.

12. The compound as recited in claim 9 wherein
$R_1$ is 5-chloro;
$R_{10}$ and $R_{11}$ are H;
$R_4$ is benzyl; and
$R_{12}$ is (3S,4S)-dihydroxypyrrolidin-1-yl.

13. The compound as recited in claim 9 wherein
$R_1$ is 5-chloro;
$R_{10}$ and $R_{11}$ are H;
$R_4$ is benzyl; and
$R_{12}$ is (3R,4S)-dihydroxypyrrolidin-1-yl.

14. A compound as recited in claim 1 wherein
$R_1$ is H, halo, methyl or cyano;
$R_{10}$ and $R_{11}$ are each independently H or halo;
A is —C(H)=;
$R_2$ and $R_3$ are H;
$R_4$ is phenyl($C_1$–$C_2$)alkyl wherein said phenyl groups are mono-, di- or tri-substituted independently with H or halo or mono- or di-substituted independently with H, halo, ($C_1$–$C_4$)alkyl, ($C_1$–$C_4$)alkoxy, trifluoromethyl, hydroxy, amino or cyano; or
$R_4$ is thien-2- or -3-yl($C_1$–$C_2$)alkyl or fur-2- or -3-yl ($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;
$R_5$ is hydroxy;
$R_6$ is carboxy or ($C_1$–$C_8$)alkoxycarbonyl; and
$R_7$ is H, fluoro or ($C_1$–$C_6$)alkyl.

15. A compound as recited in claim 14 wherein
the carbon atom a is (S) stereochemistry;
the carbon atom b is (R) stereochemistry;
$R_4$ is phenyl($C_1$–$C_2$)alkyl, thien-2-yl-($C_1$–$C_2$)alkyl, thien-3-yl-($C_1$–$C_2$)alkyl, fur-2-yl-($C_1$–$C_2$)alkyl or fur-3-yl-($C_1$–$C_2$)alkyl wherein said rings are mono- or di-substituted independently with H or fluoro;
$R_{10}$ and $R_{11}$ are H;
$R_6$ is carboxy; and
$R_7$ is H.

16. The compound as recited in claim 15 wherein
$R_1$ is 5-chloro;
$R_{10}$ and $R_{11}$ are H; and
$R_4$ is benzyl.

17. A compound as recited in claim 1 wherein
$R_1$ is H, halo, methyl or cyano;
$R_{10}$ and $R_{11}$ are each independently H or halo;
A is —C(H)=;
$R_2$ and $R_3$ are H;
$R_4$ is phenyl($C_1$–$C_2$)alkyl wherein said phenyl groups are mono-, di- or tri-substituted independently with H or halo or mono- or di-substituted independently with H, halo, ($C_1$–$C_4$)alkyl, ($C_1$–$C_4$)alkoxy, trifluoromethyl, hydroxy, amino or cyano; or
$R_4$ is thien-2- or -3-yl($C_1$–$C_2$)alkyl or fur-2- or -3-yl ($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$) alkoxy, amino or hydroxy and said mono- or di-substituents are bonded to carbon;
$R_5$ is fluoro, ($C_1$–$C_5$)alkoxy, amino($C_1$–$C_4$)alkoxy, mono-N- or di-N,N-($C_1$–$C_4$)alkylamino($C_1$–$C_4$)alkoxy, carboxy($C_1$–$C_4$)alkoxy, ($C_1$$C_5$)alkoxy-carbonyl($C_1$$C_4$)alkoxy, benzyloxycarbonyl($C_1$–$C_4$)alkoxy;
$R_6$ is carboxy or ($C_1$–$C_8$)alkoxycarbonyl; and
$R_7$ is H, fluoro or ($C_1$–$C_6$)alkyl.

18. A compound as recited in claim 1 wherein
$R_1$ is H, halo, methyl or cyano;
$R_{10}$ and $R_{11}$ are each independently H or halo;
A is —C(H)=;
$R_2$ and $R_3$ are H;
$R_4$ is phenyl($C_1$–$C_2$)alkyl wherein said phenyl groups are mono-, di- or tri-substituted independently with H or halo or mono- or di-substituted independently with H, halo, ($C_1$–$C_4$)alkyl, ($C_1$–$C_4$)alkoxy, trifluoromethyl, hydroxy, amino or cyano; or
$R_4$ is thien-2- or -3-yl($C_1$–$C_2$)alkyl or fur-2- or -3-yl ($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$) alkoxy, amino or hydroxy and said mono- or di-substituents are bonded to carbon;
$R_5$ is fluoro, ($C_1$–$C_5$)alkoxy, amino($C_1$–$C_4$)alkoxy, mono-N- or di-N,N-($C_1$–$C_4$)alkylamino($C_1$–$C_4$)alkoxy, carboxy($C_1$–$C_4$)alkoxy, ($C_1$–$C_5$)alkoxy-carbonyl ($C_1$–$C_4$)alkoxy, benzyloxycarbonyl($C_1$–$C_4$)alkoxy;
$R_6$ is C(O)$NR_8R_9$ or C(O)$R_{12}$; and
$R_7$ is H, fluoro or ($C_1$–$C_6$)alkyl.

19. A method for treating a glycogen phosphorylase dependent disease or condition in a mammal which comprises administering to a mammal suffering from a glycogen phosphorylase dependent disease or condition a therapeutically effective amount of a compound of claim 1.

20. The method as recited in claim 19 for treating hyperglycemia in a mammal by administering to a mammal suffering from hyperglycemia a therapeutically effective amount of a compound of claim 1.

21. The method as recited in claim 19 for treating diabetes in a mammal by administering to a mammal suffering from diabetes a therapeutically effective amount of a compound of claim 1.

22. The method as recited in claim 19 for treating hypercholesterolemia in a mammal by administering to a mammal suffering from hypercholesterolemia a therapeutically effective amount of a compound of claim 1.

23. The method as recited in claim 19 for treating atherosclerosis in a mammal by administering to a mammal suffering from atherosclerosis a therapeutically effective amount of a compound of claim 1.

24. The method as recited in claim 19 for treating hyperinsulinemia in a mammal by administering to a mammal suffering from hyperinsulinemia a therapeutically effective amount of a compound of claim 1.

25. The method as recited in claim 19 for treating hypertension in a mammal by administering to a mammal suffering from hypertension a therapeutically effective amount of a compound of claim 1.

26. The method as recited in claim 19 for treating hyperlipidemia in a mammal by administering to a mammal suffering from hyperlipidemia a therapeutically effective amount of a compound of claim 1.

27. The method as recited in claim 19 for preventing a myocardial ischemic injury in a mammal by administering to a mammal at risk for perioperative myocardial ischemic injury a therapeutically effective amount of a compound of claim 1.

28. A pharmaceutical composition which comprises a therapeutically effective amount of a compound of claim 1 and a pharmaceutically acceptable carrier.

29. A pharmaceutical composition for the treatment of glycogen phosphorylase dependent diseases or conditions in mammals which comprises a therapeutically effective amount of a compound of claim 1 and a pharmaceutically acceptable carrier.

30. A compound of Formula I

Formula I and the pharmaceutically acceptable salts and prodrugs thereof wherein the dotted line (---) is an optional bond;

A is —C(H)=, —C(($C_1$–$C_4$)alkyl)= or —C(halo)= when the dotted line (---) is a bond, or A is methylene or —CH(($C_1$–$C_4$)alkyl)— when the dotted line (---) is not a bond;

$R_1$, $R_{10}$ or $R_{11}$ are each independently H, halo, 4-, 6- or 7-nitro, cyano, ($C_1$–$C_4$)alkyl, ($C_1$–$C_4$)alkoxy, fluoromethyl, difluoromethyl or trifluoromethyl;

$R_2$ is H;

$R_3$ is H or ($C_1$–$C_5$)alkyl;

$R_4$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, phenyl($C_1$–$C_4$)alkoxy ($C_1C_4$)alkyl, thien-2- or -3-yl($C_1$–$C_4$)alkyl or fur-2- or -3-yl($C_1$–$C_4$)alkyl wherein said $R_4$ rings are mono-, di- or tri-substituted independently on carbon with H, halo, ($C_1$–$C_4$)alkyl, ($C_1$–$C_4$)alkoxy, trifluoromethyl, hydroxy, amino or cyano;

$R_5$ is H, hydroxy, fluoro, ($C_1$–$C_5$)alkyl, ($C_1$–$C_5$)alkoxy, ($C_1$–$C_6$)alkanoyl, amino($C_1$–$C_4$)alkoxy, mono-N- or di-N,N-($C_1$–$C_4$)alkylamino($C_1$–$C_4$)alkoxy, carboxy ($C_1$–$C_4$)alkoxy, ($C_1$–$C_5$)alkoxy-carbonyl($C_1$–$C_4$) alkoxy, benzyloxycarbonyl($C_1$–$C_4$)alkoxy, or carbonyloxy wherein said carbonyloxy is carbon-carbon linked with phenyl or furyl and wherein said preceding $R_5$ rings are optionally mono-substituted with halo, ($C_1$–$C_4$)alkyl, ($C_1$–$C_4$)alkoxy, hydroxy, amino or trifluoromethyl and said mono-substituents are bonded to carbon;

$R_7$ is H, fluoro or ($C_1$–$C_5$)alkyl; or $R_5$ and $R_7$ can be taken together to be oxo;

$R_6$ is carboxy, ($C_1$–$C_8$)alkoxycarbonyl, C(O)$NR_8R_9$ or C(O)$R_{12}$, wherein $R_8$ is H, ($C_1$–$C_3$)alkyl, hydroxy or ($C_1$–$C_3$)alkoxy; and $R_9$ is H, ($C_1$–$C_8$)alkyl, hydroxy, ($C_1$–$C_8$)alkoxy, methylene-perfluorinated($C_1$–$C_8$)alkyl, phenyl, thienyl, furyl or pyrrolidinyl wherein said preceding $R_9$ rings are carbon-nitrogen linked; or $R_9$ is mono-, di- or tri-substituted ($C_1$–$C_5$)alkyl, wherein said substituents are independently H, hydroxy, amino, mono-N- or di-N,N-($C_1$–$C_5$)alkylamino; or $R_9$ is mono- or di-substituted ($C_1$–$C_5$)alkyl, wherein said substituents are independently phenyl, furyl or pyrrolidinyl wherein the nonaromatic nitrogen-containing $R_9$ rings are optionally mono-substituted on nitrogen with ($C_1$–$C_6$) alkyl, benzyl, benzoyl or ($C_1$–$C_6$)alkoxycarbonyl and wherein the $R_9$ rings are optionally mono-substituted on carbon with halo, ($C_1$–$C_4$)alkyl, ($C_1$–$C_4$)alkoxy, hydroxy, amino, or mono-N- and di-N,N ($C_1$–$C_5$) alkylamino provided that no quaternized nitrogen is included and there are no nitrogen-oxygen, nitrogen-nitrogen or nitrogen-halo bonds;

$R_{12}$ is 2-($C_1$–$C_6$)alkoxycarbonylpyrrolidin-1-yl or 2(R)-hydroxymethylpyrrolidin-1-yl; or $R_{12}$ is 3- and/or 4-, mono- or di-substituted pyrrolidin-1-yl wherein said $R_{12}$ substituents are independently H, halo, ($C_1$–$C_5$)-alkyl, hydroxy, amino, mono-N- or di-N, N-($C_1$–$C_5$)alkylamino, formyl, oxo, hydroxyimino, ($C_1$–$C_5$)alkoxy, carboxy, carbamoyl, mono-N- or di-N, N-($C_1$–$C_4$)alkylcarbamoyl, ($C_1$–$C_4$)alkoxyimino, ($C_1$–$C_4$)alkoxymethoxy, ($C_1$–$C_6$)alkoxycarbonyl, carboxy($C_1$–$C_5$)alkyl or hydroxy($C_1$–$C_5$)alkyl;

with the proviso that if $R_4$ is H, methyl, ethyl or n-propyl, $R_5$ is OH;

with the proviso that if $R_5$ and $R_7$ are H, then $R_4$ is not H, methyl, ethyl, n-propyl, hydroxy($C_1$–$C_3$)alkyl or ($C_1$–$C_3$)alkoxy($C_1$–$C_3$)alkyl and $R_6$ is C(O)$NR_8R_9$, C(O)$R_{12}$ or ($C_1$–$C_4$)alkoxycarbonyl.

31. A compound of Formula I

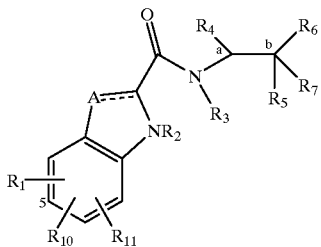

Formula I and the pharmaceutically acceptable salts and prodrugs thereof wherein the dotted line (---) is an optional bond;

A is —C(H)=, —C(($C_1$–$C_4$)alkyl)= or —C(halo)= when the dotted line (---) is a bond, or A is methylene or —CH(($C_1$–$C_4$)alkyl)— when the dotted line (---) is not a bond;

$R_1$, $R_{10}$ or $R_{11}$ are each independently H, halo, 4-, 6- or 7-nitro, cyano, ($C_1$–$C_4$)alkyl, ($C_1$–$C_4$)alkoxy, fluoromethyl, difluoromethyl or trifluoromethyl;

$R_2$ is H;

$R_3$ is H or ($C_1$–$C_5$)alkyl;

$R_4$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, phenyl($C_1$–$C_4$)alkoxy ($C_1$–$C_4$)alkyl, thien-2- or -3-yl($C_1$–$C_4$)alkyl or fur-2- or -3-yl($C_1$–$C_4$)alkyl wherein said $R_4$ rings are mono-, di- or tri-substituted independently on carbon with H, halo, ($C_1$–$C_4$)alkyl, ($C_1$–$C_4$)alkoxy, trifluoromethyl, hydroxy, amino or cyano;

$R_5$ is hydroxy;

$R_7$ is H, fluoro or ($C_1$–$C_5$)alkyl; or $R_6$ is carboxy, ($C_1$–$C_8$)alkoxycarbonyl, C(O)$NR_8R_9$ or C(O)$R_{12}$, wherein $R_8$ is H, ($C_1$–$C_3$)alkyl, hydroxy or ($C_1$–$C_3$)alkoxy; and $R_9$ is H, ($C_1$–$C_8$)alkyl, hydroxy, ($C_1$–$C_8$)alkoxy, methylene-perfluorinated($C_1$–$C_8$)alkyl, phenyl, thienyl, furyl or pyrrolidinyl wherein said preceding $R_9$ rings are carbon-nitrogen linked; or $R_9$ is mono-, di- or tri-substituted ($C_1$–$C_5$)alkyl, wherein said substituents are independently H, hydroxy, amino, mono-N- or di-N,N-($C_1$–$C_5$)alkylamino; or $R_9$ is mono- or di-substituted ($C_1$–$C_5$)alkyl, wherein said substituents are independently phenyl, furyl or pyrrolidinyl wherein the nonaromatic nitrogen-containing $R_9$ rings are optionally mono-substituted on nitrogen with ($C_1$–$C_6$) alkyl, benzyl, benzoyl or ($C_1$–$C_6$)alkoxycarbonyl and wherein the $R_9$ rings are optionally mono-substituted on carbon with halo, ($C_1$–$C_4$)alkyl, ($C_1$–$C_4$)alkoxy, hydroxy, amino, or mono-N- and di-N,N ($C_1$–$C_5$) alkylamino provided that no quaternized nitrogen is included and there are no nitrogen-oxygen, nitrogen-nitrogen or nitrogen-halo bonds;

$R_{12}$ is 2-($C_1$–$C_6$)alkoxycarbonylpyrrolidin-1-yl or 2(R)-hydroxymethylpyrrolidin-1-yl; or $R_{12}$ is 3- and/or 4-, mono- or di-substituted pyrrolidin-1-yl wherein said $R_{12}$ substituents are independently H, halo, ($C_1$–$C_5$)-alkyl, hydroxy, amino, mono-N- or di-N, N-($C_1$–$C_5$)alkylamino, formyl, oxo, hydroxyimino, ($C_1$–$C_5$)alkoxy, carboxy, carbamoyl, mono-N- or di-N, N-($C_1$–$C_4$)alkylcarbamoyl, ($C_1$–$C_4$)alkoxyimino, ($C_1$–$C_4$)alkoxymethoxy, ($C_1$–$C_6$)alkoxycarbonyl, carboxy($C_1$–$C_5$)alkyl or hydroxy($C_1$–$C_5$)alkyl;

with the proviso that if $R_4$ is H, methyl, ethyl or n-propyl, $R_5$ is OH;

with the proviso that if $R_5$ and $R_7$ are H, then $R_4$ is not H, methyl, ethyl, n-propyl, hydroxy($C_1$–$C_3$)alkyl or ($C_1$–$C_3$)alkoxy($C_1$–$C_3$)alkyl and $R_6$ is C(O)$NR_8R_9$, C(O)$R_{12}$ or ($C_1$–$C_4$)alkoxycarbonyl.

32. A compound of Formula I

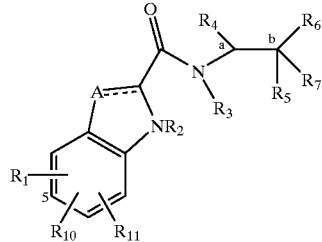

Formula I and the pharmaceutically acceptable salts and prodrugs thereof wherein the dotted line (---) is an optional bond;

A is —C(H)=, —C(($C_1$–$C_4$)alkyl)= or —C(halo)= when the dotted line (---) is a bond, or A is methylene or —CH(($C_1$–$C_4$)alkyl)— when the dotted line (---) is not a bond;

$R_1$, $R_{10}$ or $R_{11}$ are each independently H, halo, 4-, 6- or 7-nitro, cyano, ($C_1$–$C_4$)alkyl, ($C_1$–$C_4$)alkoxy, fluoromethyl, difluoromethyl or trifluoromethyl;

$R_2$ is H;

$R_3$ is H or ($C_1$–$C_5$)alkyl;

$R_4$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, phenyl($C_1$–$C_4$)alkoxy ($C_1$–$C_4$)alkyl, thien-2- or -3-yl($C_1$–$C_4$)alkyl or fur-2- or -3-yl($C_1$–$C_4$)alkyl wherein said $R_4$ rings are mono-, di- or tri-substituted independently on carbon with H, halo, ($C_1$–$C_4$)alkyl, ($C_1$–$C_4$)alkoxy, trifluoromethyl, hydroxy, amino or cyano;

$R_5$ is H, hydroxy, fluoro, ($C_1$–$C_5$)alkyl, ($C_1$–$C_5$)alkoxy, ($C_1$–$C_6$)alkanoyl, amino($C_1$–$C_4$)alkoxy, mono-N- or di-N,N-($C_1$–$C_4$)alkylamino($C_1$–$C_4$)alkoxy, carboxy ($C_1$–$C_4$)alkoxy, ($C_1$–$C_5$)alkoxy-carbonyl($C_1$–$C_4$) alkoxy, benzyloxycarbonyl($C_1$–$C_4$)alkoxy, or carbonyloxy wherein said carbonyloxy is carbon-carbon linked with phenyl or furyl and wherein said preceding $R_5$ rings are optionally mono-substituted with halo, ($C_1$–$C_4$)alkyl, ($C_1$–$C_4$)alkoxy, hydroxy, amino or trifluoromethyl and said mono-substituents are bonded to carbon;

$R_7$ is H, fluoro or ($C_1$–$C_5$)alkyl; or $R_5$ and $R_7$ can be taken together to be oxo;

$R_6$ is carboxy, ($C_1$–$C_8$)alkoxycarbonyl, C(O)$NR_8R_9$ or C(O)$R_{12}$, wherein $R_8$ is H, ($C_1$–$C_3$)alkyl, hydroxy or ($C_1$–$C_3$)alkoxy; and $R_9$ is hydroxy, ($C_1$–$C_8$)alkoxy, methylene-perfluorinated ($C_1$–$C_8$)alkyl, furyl or pyrrolidinyl wherein said preceding $R_9$ rings are carbon-nitrogen linked; or $R_9$ is di- or tri-substituted ($C_1$–$C_5$)alkyl, wherein said substituents are independently hydroxy, amino, mono-N- or di-N,N-($C_1$–$C_5$)alkylamino; or R$_9$ is mono- or di-substituted (C$_1$–C$_5$)alkyl, wherein said substituents are independently furyl or pyrrolidinyl wherein the nonaromatic nitrogen-containing R$_9$ rings are mono-substituted on nitrogen with (C$_1$–C$_6$)alkyl, benzyl, benzoyl or (C$_1$–C$_6$)alkoxycarbonyl and wherein the R$_9$ rings are optionally mono-substituted on carbon with halo, (C$_1$–C$_4$)alkyl, (C$_1$–C$_4$)alkoxy, hydroxy, amino, or mono-N- and di-N,N (C$_1$–C$_5$) alkylamino provided that no quaternized nitrogen is included and there are no nitrogen-oxygen, nitrogen-nitrogen or nitrogen-halo bonds;

R$_{12}$ is 2-(C$_1$–C$_6$)alkoxycarbonylpyrrolidin-1-yl or 2(R)-hydroxymethylpyrrolidin-1-yl; or R$_{12}$ is 3- and/or 4-, di-substituted pyrrolidin-1-yl with the proviso that if R$_4$ is H, methyl, ethyl or n-propyl, R$_5$ is OH;

with the proviso that if R$_5$ and R$_7$ are H, then R$_4$ is not H, methyl, ethyl, n-propyl, hydroxy(C$_1$–C$_3$)alkyl or (C$_1$–C$_3$)alkoxy(C$_1$–C$_3$)alkyl and R$_6$ is C(O)NR$_8$R$_9$, C(O)R$_{12}$ or (C$_1$–C$_4$)alkoxycarbonyl.

33. A pharmaceutical composition which comprises a therapeutically effective amount of
a) a glycogen phosphorylase inhibitor as recited in claim 30;
b) an antidiabetic agent selected from insulin and insulin analogs; insulinotropin; Sulfonylureas and analogs; Biguanides; α2-Antagonists and Imidazolines; insulin secretagogues; Glitazones; Fatty Acid Oxidation inhibitors; α-Glucosidase inhibitors; β-Agonists; Phosphodiesterase Inhibitors; Lipid-lowering Agents; Antiobesity Agents; Vanadate and vanadium complexes and peroxovanadium complexes; Amylin Antagonists; Glucagon Antagonists; Gluconeogenesis Inhibitors; Somatostatin Analogs; Antilipolytic Agents; and
c) optionally a pharmaceutically acceptable carrier.

34. A compound as recited in claim 32 wherein R$_5$ is hydroxy.

35. A method for treating a glycogen phosphorylase dependent disease or condition in a mammal which comprises administering to a mammal suffering from a glycogen phosphorylase dependent disease or condition a therapeutically effective amount of a compound of claim 30.

36. A method for treating hyperglycemia in a mammal by administering to a mammal suffering from hyperglycemia a therapeutically effective amount of a compound of claim 30.

37. A method for treating diabetes in a mammal by administering to a mammal suffering from diabetes a therapeutically effective amount of a compound of claim 30.

38. A method for treating hypercholesterolemia in a mammal by administering to a mammal suffering from hypercholesterolemia a therapeutically effective amount of a compound of claim 30.

39. A method for for treating atherosclerosis in a mammal by administering to a mammal suffering from atherosclerosis a therapeutically effective amount of a compound of claim 30.

40. A method for treating hyperinsulinemia in a mammal by administering to a mammal suffering from hyperinsulinemia a therapeutically effective amount of a compound of claim 30.

41. A method for treating hypertension in a mammal by administering to a mammal suffering from hypertension a therapeutically effective amount of a compound of claim 30.

42. A method for treating hyperlipidemia in a mammal by administering to a mammal suffering from hyperlipidemia a therapeutically effective amount of a compound of claim 30.

43. A method for preventing a myocardial ischemic injury in a mammal by administering to a mammal at risk for perioperative myocardial ischemic injury a therapeutically effective amount of a compound of claim 30.

44. A pharmaceutical composition for the treatment of glycogen phosphorylase dependent diseases or conditions in mammals which comprises a therapeutically effective amount of a compound of claim 30 and a pharmaceutically acceptable carrier.

45. A method for treating Type I diabetes in a mammal which comprises administering to a mammal a therapeutically effective amount of a compound of claim 30.

46. A method as recited in claim 45 wherein the compound is 5-chloro-1H-indole-2-carboxylic acid [(1S)-benzyl-3-((3R,4S)-dihydroxy-pyrrolidin-1-yl)-(2R)-hydroxy-3-oxo-propyl]-amide.

47. A method for treating Type II diabetes in a mammal which comprises administering to a mammal a therapeutically effective amount of a compound of claim 30.

48. A method as recited in claim 47 wherein the compound is 5-chloro-1H-indole-2-carboxylic acid [(1S)-benzyl-3-((3R,4S)-dihydroxy-pyrrolidin-1-yl)-(2R)-hydroxy-3-oxo-propyl]-amide.

49. A method for treating Type II diabetes in a mammal which comprises administering to a mammal a therapeutically effective amount of a compound of claim 30.

50. A method as recited in claim 49 wherein the compound is 5-chloro-1H-indole-2-carboxylic acid [(1S)-benzyl-3-((3R,4S)-dihydroxy-pyrrolidin-1-yl)-(2R)-hydroxy-3-oxo-propyl]-amide.

51. A method for treating neuropathy in a mammal which comprises administering to a mammal a therapeutically effective amount of a compound of claim 30.

52. A method as recited in claim 51 wherein the compound is 5-chloro-1H-indole-2-carboxylic acid [(1S)-benzyl-3-((3R,4S)-dihydroxy-pyrrolidin-1-yl)-(2R)-hydroxy-3-oxo-propyl]-amide.

53. A method for treating neuropathy in a mammal which comprises administering to a mammal a therapeutically effective amount of a compound of claim 30.

54. A method as recited in claim 53 wherein the compound is 5-chloro-1H-indole-2-carboxylic acid [(1S)-benzyl-3-((3R,4S)-dihydroxy-pyrrolidin-1-yl)-(2R)-hydroxy-3-oxo-propyl]-amide.

55. A method for treating nephropathy in a mammal which comprises administering to a mammal a therapeutically effective amount of a compound of claim 30.

56. A method as recited in claim 55 wherein the compound is 5-chloro-1H-indole-2-carboxylic acid [(1S)-benzyl-3-((3R,4S)-dihydroxy-pyrrolidin-1-yl)-(2R)-hydroxy-3-oxo-propyl]-amide.

57. A method for treating nephropathy in a mammal which comprises administering to a mammal a therapeutically effective amount of a compound of claim 30.

58. A method as recited in claim 57 wherein the compound is 5-chloro-1H-indole-2-carboxylic acid [(1S)-benzyl-3-((3R,4S)-dihydroxy-pyrrolidin-1-yl)-(2R)-hydroxy-3-oxo-propyl]-amide.

59. A method for treating retinopathy in a mammal which comprises administering to a mammal a therapeutically effective amount of a compound of claim 30.

60. A method as recited in claim 59 wherein the compound is 5-chloro-1H-indole-2-carboxylic acid [(1S)-benzyl-3-((3R,4S)-dihydroxy-pyrrolidin-1-yl)-(2R)-hydroxy-3-oxo-propyl]-amide.

61. A method for treating retinopathy in a mammal which comprises administering to a mammal a therapeutically effective amount of a compound of claim 30.

62. A method as recited in claim 61 wherein the compound is 5-chloro-1H-indole-2-carboxylic acid [(1S)-benzyl-3-((3R,4S)-dihydroxy-pyrrolidin-1-yl)-(2R)-hydroxy-3-oxo-propyl]-amide.

63. A method for treating cataracts in a mammal which comprises administering to a mammal a therapeutically effective amount of a compound of claim 30.

64. A method as recited in claim 63 wherein the compound is 5-chloro-1H-indole-2-carboxylic acid [(1S)-benzyl-3-((3R,4S)-dihydroxy-pyrrolidin-1-yl)-(2R)-hydroxy-3-oxo-propyl]-amide.

65. A method for treating cataracts in a mammal which comprises administering to a mammal a therapeutically effective amount of a compound of claim 30.

66. A method as recited in claim 65 wherein the compound is 5-chloro-1H-indole-2-carboxylic acid [(1S)-benzyl-3-((3R,4S)-dihydroxy-pyrrolidin-1-yl)-(2R)-hydroxy-3-oxo-propyl]-amide.

67. A pharmaceutical composition which comprises a therapeutically effective amount of a.) 5-chloro-1H-indole-2-carboxylic acid [(1S)-benzyl-3-((3R,4S)-dihydroxy-pyrrolidin-1-yl)-(2R)-hydroxy-3-oxo-propyl]-amide;

b.) an antidiabetic agent selected from glypizide, glimepiride, repaglinide, metformin, pioglitazone, troglitazone, BRL49653 (rosiglitazone), acarbose and miglitol; and c.) optionally a pharmaceutically acceptable carrier.

68. A pharmaceutical composition as recited in claim 67 wherein the antidiabetic agent is glypizide.

69. A pharmaceutical composition as recited in claim 67 wherein the antidiabetic agent is glimepiride.

70. A pharmaceutical composition as recited in claim 67 wherein the antidiabetic agent is repaglinide.

71. A pharmaceutical composition as recited in claim 67 wherein the antidiabetic agent is metformin.

72. A pharmaceutical composition as recited in claim 67 wherein the antidiabetic agent is pioglitazone.

73. A pharmaceutical composition as recited in claim 67 wherein the antidiabetic agent is troglitazone.

74. A pharmaceutical composition as recited in claim 67 wherein the antidiabetic agent is BRL49653 (rosiglitazone).

75. A pharmaceutical composition as recited in claim 67 wherein the antidiabetic agent is acarbose.

76. A pharmaceutical composition as recited in claim 67 wherein the antidiabetic agent is miglitol.

77. A pharmaceutical composition which comprises a therapeutically effective amount of a. 5-chloro-1H-indole-2-carboxylic acid[(1S)-benzyl-3-((3R,4S)-dihydroxy-pyrrolidin-1-yl)-(2R)-hydroxy-3-oxo-propyl]amide, b. insulin; and c. optionally a pharmaceutically acceptable carrier.

\* \* \* \* \*